(12) United States Patent
Hecht et al.

(10) Patent No.: US 11,390,605 B2
(45) Date of Patent: Jul. 19, 2022

(54) SUBSTITUTED PYRIMIDINE COMPOUNDS AS MULTIFUNCTIONAL RADICAL QUENCHERS AND THEIR USES

(71) Applicant: ARIZONA BOARD OF REGENTS ON BEHALF OF ARIZONA STATE UNIVERSITY, Scottsdale, AZ (US)

(72) Inventors: Sidney Hecht, Phoenix, AZ (US); Omar Khdour, Phoenix, AZ (US); Arnaud Chevalier, Bruere Allichamps (FR)

(73) Assignee: ARIZONA BOARD OF REGENTS ON BEHALF OF ARIZONA STATE UNIVERSITY, Scottsdale, AZ (US)

(*) Notice: Subject to any disclaimer, the term of this patent is extended or adjusted under 35 U.S.C. 154(b) by 585 days.

(21) Appl. No.: 16/327,287

(22) PCT Filed: Aug. 18, 2017

(86) PCT No.: PCT/US2017/047640
§ 371 (c)(1),
(2) Date: Feb. 21, 2019

(87) PCT Pub. No.: WO2018/039077
PCT Pub. Date: Mar. 1, 2018

(65) Prior Publication Data
US 2021/0276979 A1 Sep. 9, 2021

Related U.S. Application Data

(60) Provisional application No. 62/379,658, filed on Aug. 25, 2016.

(51) Int. Cl.
| | |
|---|---|
| C07D 243/04 | (2006.01) |
| A61K 31/505 | (2006.01) |
| A61P 39/06 | (2006.01) |
| C07D 403/04 | (2006.01) |
| C07D 239/60 | (2006.01) |
| C07D 403/14 | (2006.01) |

(52) U.S. Cl.
CPC ............ *C07D 403/04* (2013.01); *A61P 39/06* (2018.01); *C07D 239/60* (2013.01); *C07D 403/14* (2013.01)

(58) Field of Classification Search
CPC .. C07D 403/04; C07D 239/60; C07D 403/14; A61P 39/06; A61K 31/505
See application file for complete search history.

(56) References Cited

U.S. PATENT DOCUMENTS

| | | | |
|---|---|---|---|
| 3,476,722 A | 11/1969 | Schlatzer | |
| 4,054,580 A | 10/1977 | Ohi | |
| 4,338,180 A | 7/1982 | Nakamura | |
| 4,559,157 A | 12/1985 | Smith et al. | |
| 4,608,392 A | 8/1986 | Jacquet et al. | |
| 4,820,508 A | 4/1989 | Wortzman | |
| 4,938,949 A | 7/1990 | Borch et al. | |
| 4,992,478 A | 2/1991 | Geria | |
| 5,220,042 A | 6/1993 | Iwaki et al. | |
| 5,356,898 A | 10/1994 | Belliotti et al. | |
| 8,268,849 B2 | 9/2012 | Kador et al. | |
| 8,759,336 B2 | 6/2014 | Hurt et al. | |
| 8,952,025 B2* | 2/2015 | Hecht | A61P 39/06 514/269 |
| 9,102,626 B2 | 8/2015 | Hecht et al. | |
| 9,334,250 B2 | 5/2016 | Chowdhury et al. | |
| 9,388,163 B2 | 7/2016 | Hecht et al. | |
| 9,440,967 B2 | 9/2016 | Hecht et al. | |
| 9,957,214 B2 | 5/2018 | Madathil et al. | |
| 10,364,227 B2 | 7/2019 | Hecht et al. | |
| 10,472,340 B2 | 11/2019 | Hecht et al. | |
| 10,604,501 B2 | 3/2020 | Chevalier et al. | |
| 10,745,366 B2 | 8/2020 | Hecht et al. | |
| 2001/0027196 A1 | 10/2001 | Borroni et al. | |
| 2004/0166553 A1 | 8/2004 | Nguyen et al. | |

(Continued)

FOREIGN PATENT DOCUMENTS

| | | |
|---|---|---|
| DE | 2315349 A1 | 10/1974 |
| JP | 2001209176 A | 8/2001 |

(Continued)

OTHER PUBLICATIONS

Smith, P., et al., "Measurement of protein using bicinchoninic acid", Anal Biochem 150(1), 76-85 (1985).

(Continued)

*Primary Examiner* — Theodore R. Howell
(74) *Attorney, Agent, or Firm* — Viksnins Harris Padys Malen LLP

(57) ABSTRACT

The invention provides compounds having the general formula I: and pharmaceutically acceptable salts thereof, wherein the variables $R^1$, $R^2$, $R^3$ and $R^4$ have the meaning as described herein, and compositions containing such compounds and methods for using such compounds and compositions.

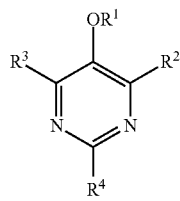

10 Claims, 5 Drawing Sheets

(56) References Cited

U.S. PATENT DOCUMENTS

| | | |
|---|---|---|
| 2008/0062838 A1 | 3/2008 | Selinfreund et al. |
| 2010/0016783 A1 | 1/2010 | Bourke, Jr. et al. |
| 2011/0319380 A1 | 12/2011 | Hardy et al. |
| 2013/0224634 A1 | 8/2013 | Berneth et al. |
| 2013/0267546 A1 | 10/2013 | Hecht et al. |
| 2013/0267548 A1 | 10/2013 | Follmann et al. |
| 2013/0317012 A1 | 11/2013 | Wischik et al. |
| 2014/0127737 A1 | 5/2014 | Kim |
| 2014/0275045 A1 | 9/2014 | Hinman et al. |
| 2018/0065941 A1 | 3/2018 | Hecht et al. |
| 2018/0319751 A1 | 11/2018 | Hecht et al. |
| 2020/0115355 A1 | 4/2020 | Hecht et al. |
| 2020/0247775 A1 | 8/2020 | Chevalier et al. |
| 2020/0407333 A1 | 12/2020 | Hecht et al. |

FOREIGN PATENT DOCUMENTS

| | | | |
|---|---|---|---|
| WO | 1996031217 | A1 | 10/1996 |
| WO | 2002000683 | A2 | 1/2002 |
| WO | 2003007950 | A1 | 1/2003 |
| WO | 2006089301 | A2 | 8/2006 |
| WO | 2006100212 | A1 | 9/2006 |
| WO | 2009142760 | A1 | 11/2009 |
| WO | 2011103536 | A1 | 8/2011 |
| WO | 2012022467 | A2 | 2/2012 |
| WO | 2012138713 | A2 | 10/2012 |
| WO | 2013120040 | A1 | 8/2013 |
| WO | 2013120081 | A1 | 8/2013 |
| WO | 2014055629 | A1 | 4/2014 |
| WO | 2014059158 | A1 | 4/2014 |
| WO | 2014145119 | A1 | 9/2014 |
| WO | 2016133959 | A1 | 8/2016 |
| WO | 2016133995 | A1 | 8/2016 |
| WO | 2017218537 | A1 | 12/2017 |
| WO | 2016133959 | A9 | 2/2018 |
| WO | 2018039077 | A1 | 3/2018 |
| WO | 2018039487 | A1 | 3/2018 |
| WO | 2018039077 | A8 | 9/2018 |

OTHER PUBLICATIONS

Smith, A , et al., "Preparation, properties, and conditions for assay of mitochondria: Slaughterhouse material, small-scale", Methods Enzymol. 10, 81-86 (1967).

Smith, R , et al., "Using mitochondria-targeted molecules to study mitochondrial radical production and its consequences", Biochem Soc Trans 31(6), 1295-1299 (2003).

Syper, L , "The Baeyer-Villiger Oxidation of Aromatic Aldehydes and Ketones with Hydrogen Peroxide Catalyzed by Selenium Compounds. A Convenient Method for the Preparation of Phenols", Synthesis 1989(3), 167-172 (1989).

Takano, S , et al., "An Efficient Stereoselective Preparation of Vitamin E (α-Tocopherol) from Phytol", Synlett 1990 (8), 451-452 (1990).

Takano, S , et al., "Asymmetric construction of optically active 3-hydroxyalkyne functionalities", J Chem Soc Chem Commun (18), 1344-1345 (1989).

Takenaka, Y , et al., "The effect of alpha-tocopherol as an antioxidant on the oxidation of membrane protein thiols induced by free radicals generated in different sites", Arch Biochem Biophys 285(2), 344-350 (1991).

Tallman, K, et al., "Kinetic Products of Linoleate Peroxidation: Rapid β-Fragmentation of Nonconjugated Peroxyls", J Am Chem Soc 123(47), 11827-11828 (2001).

Tirmenstein, M , et al., "Glutathione depletion and the production of reactive oxygen species in isolated hepatocyte suspensions", Chem Biol Interact 127(3), 201-217 (2000).

Traber, M , et al., "Human plasma vitamin E kinetics demonstrate rapid recycling of plasma RRR-alpha-tocopherol", Proc Natl Acad Sci USA 91(21), 10005-10008 (1994).

Traber, M , et al., "Preferential incorporation of alpha-tocopherol vs gamma-tocopherol in human lipoproteins", Am J Clin Nutr 49(3), 517-526 (1989).

Trnka, J , et al., "Antioxidant properties of MitoTEMPOL and its hydroxylamine", Free Radic Res 43(1), 4-12 (2009).

Trounce, I , et al., "Assessment of mitochondrial oxidative phosphorylation in patient muscle biopsies, lymphoblasts, and transmitochondrial cell lines", Methods Enzymol. 264, 484-509 (1996).

Turrens, J , "Mitochondrial formation of reactive oxygen species", J Physiol 552, 335-344 (2003).

USPTO , Final Office Action for U.S. Appl. No. 13/855,133, dated Jun. 17, 2014, 9 pages.

USPTO , Final Office Action for U.S. Appl. No. 14/009,437, dated Mar. 18, 2015, 8 pages.

USPTO , Final Office Action for U.S. Appl. No. 14/371,579, dated Sep. 2, 2015, 11 pages.

USPTO , Final Office Action for U.S. Appl. No. 14/434,725, notification dated Feb. 28, 2017, 10 pages.

USPTO , Non-Final Office Action for U.S. Appl. No. 13/855,133, dated Dec. 3, 2013, 10 pages.

USPTO , Non-Final Office Action for U.S. Appl. No. 14/009,437, dated Dec. 9, 2014, 8 pages.

USPTO , Non-Final Office Action for U.S. Appl. No. 14/371,579, dated Mar. 18, 2015, 17 pages.

USPTO , Non-Final Office Action for U.S. Appl. No. 14/432,885, dated Nov. 12, 2015, 6 pages.

USPTO , Non-Final Office Action for U.S. Appl. No. 14/434,725, notification dated Aug. 23, 2017, 12 pages.

USPTO , Non-Final Office Action for U.S. Appl. No. 14/434,725, notification dated Aug. 29, 2016, 17 pages.

USPTO , Non-Final Office Action for U.S. Appl. No. 14/731,950, dated Nov. 6, 2015, 7 pages.

Van Haaften, R , et al., "No reduction of alpha-tocopherol quinone by glutathione in rat liver microsomes", Biochem Pharmacol 61(6), 715-719 (2001).

Viehe, H , et al., "The captodative effect", Acc Chem Res 18(5), 148-154 (1985).

Vinod, K , et al., "Os(VIII) as an Efficient Homogeneous Catalyst for the Oxidative Decolorization of Methylene Blue Dye with Alkaline Chloramine-T: Kinetic, Mechanistic, and Platinum Metal Ions Reactivity Studies", Ind Eng Chem Res 49(7), 3137-3145 (2010).

Wallace, D , "Mouse models for mitochondrial disease", Am J Med Genet 106(1), 71-93 (2001).

Wijtmans, M , et al., "6-Amino-3-Pyridinols: Towards Diffusion-Controlled Chain-Breaking Antioxidants", Angew Chem Int Ed 42(36), 4370-4373 (2003).

Wijtmans , et al., "Synthesis and Reactivity of Some 6-Substituted-2,4-dimethyl-3-pyridinols, a Novel Class of Chain-Breaking Antioxidants", J. Org. Chem.69(26), 9215-9223 (2004).

Wilson , "Frataxin and frataxin deficiency in Friedreich's ataxia", J. Neurol. Sci. 207(1-2), 103-105 (2003).

Wilson , et al., "Respiratory deficiency due to loss of mitochondrial DNA in yeast lacking the frataxin homologue", Nature Genetics 16(4), 352-357 (1997).

Wright, A, et al., "Lifespan and mitochondrial control of neurodegeneration", Nat Genet 36(11), 1153-1158 (2004).

Wu , et al., "Autoxidation of phosphatidylcholine liposomes", Lipids 17(6), 403-413 (1982).

Yamada , et al., "Immunochemical detection of a lipofuscin-like fluorophore derived from malondialdehyde and lysine", J Lipid Res. 42(8), 1187-1196 (2001).

Yin , et al., "Biochemical basis of lipofuscin, ceroid, and age pigment-like fluorophores", Free Rad. Biol. Med. 21(6), 871-888 (1996).

Ying, W , et al., "Inhibition of mitochondrial calcium ion transport by an oxo-bridged dinuclear ruthenium ammine complex", Biochemistry 30(20), 4949-4952 (1991).

Yoon , et al., "Frataxin-mediated Iron Delivery to Ferrochelatase in the Final Step of Heme Biosynthesis", J. Biol. Chem. 279(25), 25943-25946 (2004).

(56) References Cited

OTHER PUBLICATIONS

Yoon, et al., "Iron-sulfur cluster biosynthesis. Characterization of frataxin as an iron donor for assembly of [2Fe-2S] clusters in ISU-type proteins", J. Am. Chern. Soc. 125(20), 6078-6084 (2003).
Yoshihara, K, et al., "Hydroxybenzoquinones from Myrsinaceae Plants. IV. Further Confirmation of the Structures of Ardisiaquinones and Some Observations on Alkylaminobenzoquinone Derivatives", Chem Pharm Bull 16(12), 2383-2389 (1968).
Zhang, D, et al., "Bax and the mitochondrial permeability transition cooperate in the release of cytochrome c during andoplasmic reticulum-stress-induced apoptosis", Cell Death Differ 14(4), 703-715 (2007, available online 2006).
Zhang, D, et al., "The mitochondrial permeability transition regulates cytochrome c release for apoptosis during endoplasmic reticulum stress by remodeling the cristae junction", J Biol Chem 283(6), 3476-3486 (2008, available online 2007).
Zierz, S, et al., "Exogenous coenzyme Q (coq) fails to increase coq in skeletal muscle of two patients with mitochondrial myopathies", J Neurol Sci 95(3), 283-290 (1990).
Zimmerman, M, et al., "Mitochondrial Dysfunction and Mitochondrial-Produced Reactive Oxygen Species: New Targets for Neurogenic Hypertension?", Hypertension 53(2), 112-114 (2008).
Korytnyk, W, et al., "On the Inhibitory Activity of 4-Vinyl Analogues of Pyridoxal: Enzyme and Cell Culture Studies", Biochemistry 15(25), 5458-5466 (1976).
Kowaltowski, A, et al., "Mitochondrial damage induced by conditions of oxidative stress", Free Radic Biol Med 26 (3-4), 463-471 (1999).
Kowaltowski, A, et al., "Mitochondrial permeability transition and oxidative stress", FEBS Lett 495(1-2), 12-15 (2001).
Kowaltowski, A, et al., "The Thiol-specific Antioxidant Enzyme Prevents Mitochondrial Permeability Transition", J Biol Chem 273(21), 12766-12769 (1998).
Kuypers, F, et al., "Parinaric acid as a sensitive fluorescent probe for the determination of lipid peroxidation", Biochim Biophys Acta 921(2), 266-274 (1987).
La Marche, J, et al., "The Cardiomyopathy of Friedreich's Ataxia Morphological Observations in 3 Cases", Can J Neurosci 7, 389-396 (1980).
Lebel, C, et al., "Evaluation of the probe 2',7'-dichlorofluorescin as an indicator of reactive oxygen species formation and oxidative stress", Chem Res Toxicol 5(2), 227-231 (1992).
Leonard, J, et al., "Mitochondrial respiratory chain disorders I: mitochondrial DNA defects", Lancet 355(9200), 299-304 (2000).
Lerman-Sagie, T, et al., "Dramatic improvement in mitochondrial cardiomyopathy following treatment with idebenone", J Inherit Metab Dis 24(1), 28-34 (2001).
Ley, S, et al., "Tetrapropylammonium Perruthenate, Pr4N+ RuO4—, TPAP: A Catalytic Oxidant for Organic Synthesis", Synthesis 1994(7), 639-666 (1994).
Lin, et al., "A nitrogen-containing 3-alkyl-1,4-benzoquinone and a gomphilactone derivative from Embelia ribes", J. Nat. Prod. 69(11), 1629-1632 (2006).
Lin, M, et al., "Mitochondrial dysfunction and oxidative stress in neurodegenerative diseases", Nature 443(7113), 787-795 (2006).
Lopez, L, et al., "Treatment of CoQ10 Deficient Fibroblasts with Ubiquinone, CoQ Analogs, and Vitamin C: Time- and Compound-Dependent Effects", PLoS ONE 5(7), e11897-1-e11897-9 (2010).
Lowes, D, et al., "The mitochondria-targeted antioxidant MitoQ protects against organ damage in a lipopolysaccharide-peptidoglycan model of sepsis", Free Radic Biol Med 45(11), 1559-1565 (2008).
Lu, J, et al., "Concise Synthesis of Bicyclic Pyridinol Antioxidants", Org Lett 12(22), 5189-5191 (2010).
Lu, J, et al., "Design, synthesis, and evaluation of an α-tocopherol analogue as a mitochondrial antioxidant", Bioorg Med Chem 18(21), 7628-7638 (2010).
Lu, C, et al., "Role of calcium and cyclophilin D in the regulation of mitochondrial permeabilization induced by glutathione depletion", Biochem Biophys Res Commun 363(3), 572-577 (2007).
Luly, J., et al., "Routes to Mitomycins, New Syntheses of the 2,3,5,8-Tetrahydro-5,8-dioxo-1H-pyrrolo[1,2a] indole Ring System. An Efficient Synthesis of 7-Methoxymitosene", J. Am. Chem. Soc. vol. 105, 2859-2866, (1983).
L'Vova, S, et al., "Heterodiene condensation of 4-methyl-5-propoxyoxazole with vinylethynyldimethylcarbinol", Zhurnal Organicheskoi Khimii 11(7), 1537-1540 (1975).
MacCoubrey, I, et al., "Quantitative fluorescence measurements of cell viability (cytotoxicity) with a multi-well plate scanner", J Cell Biol 111(5), 58a, (1990).
MacKenzie, J, et al., "The Biological Activity of Alpha-Tocopherylhydroquinone and Alpha-Tocopherylquinone", J Biol Chem 183(2), 655-662 (1950).
Manfredini, S, et al., "Novel antioxidant agents deriving from molecular combinations of vitamins C and E analogues: 3,4-dihydroxy-5(R)-[2(R,S)-(6-hydroxy-2,5,7,8-tetramethyl-chroman-2(R,S)-yl-methyl)-[1,3]dioxolan-4(S)-yl]-5H-furan-2-one and 3-O-octadecyl derivatives", Bioorg Med Chem 8(12), 2791-2801 (2000).
Manton, K, et al., "ROS effects on neurodegeneration in Alzheimer's disease and related disorders: on environmental stresses of ionizing radiation", Curr Alzheimer Res 1(4), 277-293 (2004).
Markesbery, et al., "Oxidative alterations in Alzheimer's disease", Brain Pathology 9(1), 133-146 (1999).
Markovits, J, et al., "Ethidium dimer: a new reagent for the fluorimetric determination of nucleic acids", Anal Biochem 94(2), 259-264 (1979).
Mates, J, et al., "Antioxidant enzymes and human diseases", Clin Biochem 32, 595-603 (1999).
Matlib, M, et al., "Oxygen-bridged dinuclear ruthenium amine complex specifically inhibits Ca2+ uptake into mitochondria in vitro and in situ in single cardiac myocytes", J Biol Chem 273(17), 10223-10231 (1998).
Matsuno-Yagi, et al., "Studies on the mechanism of oxidative phosphorylation: Catalytic site cooperativity in ATP synthesis", J. Biol. Chem. 260(27), 14424-14427 (1985).
Matthews, P, et al., "Coenzyme Q10 with multiple vitamins is generally ineffective in treatment of mitochondrial disease", Neurology 43(5), 884-890 (1993).
McBride, H, et al., "Mitochondria: more than just a powerhouse", Curr Biol 16, R551-R560 (2006).
McBride, L, et al., "Nucleotide chemistry. 16. Amidine protecting groups for oligonucleotide synthesis", J Am Chem Soc 108(8), 2040-2048 (1986).
McErlean, et al., "First Synthesis of N-(3-Carboxylpropyl)-5-amino-2-hydroxy-3-tridecyl-1,4-benzoquinone, an Unusual Quinone Isolated from Embelia ribes", Journal of Organic Chemistry, 72(26), 10298-10301 (2007).
Minta, A, et al., "Fluorescent indicators for cytosolic calcium based on rhodamine and fluorescein chromophores", J Biol Chem 264(14), 8171-8178 (1989).
Moore, P, et al., "A rapid pH insensitive, two color fluorescence viability (cytotoxicity) assay", J Cell Bio 111(5), 58a (1990).
Moore, A, et al., "Alpha-Tocopheryl Quinone is Converted into Vitamin E in Man", Free Radic Biol Med 22(5), 931-934 (1997).
Mossa, et al., "Alkylated benzoquinone derivatives from Maesa Ianceolata". Phytochemistry 50(6), 1063-1068 (1999).
Moubarak, et al., "Hepatic metabolism of ergot alkaloids in beef cattle by cytochrome P450", Biochem Biophys Res Commun 274, 746-749 (2000).
Murphy, M, "Development of lipophilic cations as therapies for disorders due to mitochondrial dysfunction", Expert Opin Biol Ther 1(5), 753-764 (2001).
Murphy, M, et al., "Drug delivery to mitochondria: the key to mitochondrial medicine", Adv. Drug Delivery Rev. 41(2), 235-250 (2000).
Murphy, M, "How mitochondria produce reactive oxygen species", Biochem J 417(1), 1-13 (2009).
Nam, T, et al., "New synthetic route to N-tocopherol derivatives: synthesis of pyrrolopyridinol analogue of α-tocopherol from pyridoxine", Org Biomol Chem 9(6), 1749-1755 (2011).
Nam, T, et al., "Pyridoxine-derived bicyclic aminopyridinol antioxidants: synthesis and their antioxidant activities", Org Biomol Chem 9(24), 8475-8482 (2011).

(56) References Cited

OTHER PUBLICATIONS

Nam, T., et al., "Tetrahydro-1,8-naphthyridinol analogues of alpha-tocopherol as antioxidants in lipid membranes and low-density lipoproteins", J Am Chem Soc 129(33), 10211-10219 (2007).
Newmeyer, D., et al., "Erratum for Mitochondria: releasing power for life and unleashing the machineries of death", Cell 112(6), 873 (2003).
Newmeyer, D., et al., "Mitochondria: releasing power for life and unleashing the machineries of death", Cell 112(4), 481-490 (2003).
Niki, E., et al., "Dynamics of antioxidant action of vitamin E", Acc Chem Res 37(1), 45-51 (2004, available online 2003).
Ogasahara, S., et al., "Improvement of abnormal pyruvate metabolism and cardiac conduction defect with coenzyme Q10 in Kearns-Sayre syndrome", Neurology 35(3), 372-377 (1985).
Ogawa, "Hydroxybenzoquinones from myrsinaceae plants-II.: Distribution among myrsinaceae plants in Japan., Phytochemistry", Phytochemistry 7(5), 773-782 (1968).
Omura, K., et al., "Oxidation of alcohols by "activated" dimethyl sulfoxide, a preparative, steric and mechanistic study", Tetrahedron 34(11), 1651-1660 (1978).
Osakada, F., et al., "Alpha-tocotrienol provides the most potent neuroprotection among vitamin E analogs on cultured striatal neurons", Neuropharmacology 47(6), 904-915 (2004).
Osakada, F., et al., "Neuroprotective effects of alpha-tocopherol on oxidative stress in rat striatal cultures", Eur J Pharmacol 465(1-2), 15-22 (2003).
Ouahchi, K., et al., "Ataxia with isolated vitamin E deficiency is caused by mutations in the alpha-tocopherol transfer protein", Nat Genet 9(2), 141-145 (1995).
Palozza, P., et al., "Retracted: Design, synthesis, and antioxidant potency of novel α-tocopherol analogues in isolated membranes and intact cells", Free Redic Biol Med 44(7), 1452-1464 (2008).
Palozza, P., et al., "Retraction notice to: "Design, synthesis, and antioxidant potency of novel α-tocopherol analogues in isolated membranes and intact cells", [Free Radical Biology & Medicine 44 (2008) 1452-1464]", Free Redic Biol Med 75, 252 (2014).
Pap, E., et al., "Ratio-£uorescence microscopy of lipid oxidation in living cells usingC11-BODIPY581=591", FEBS Lett 453, 278-282 (1999).
Park, et al., "Yeast frataxin sequentially chaperones and stores iron by coupling protein assembly with iron oxidation", J. Biol. Chem. 278(33), 31340-31351 (2003).
Patent Cooperation Treaty, International Searching Authority, International Preliminary Report on Patentability and Written Opinion for PCT/US2011/025613, 8 pages, report dated Aug. 21, 2012.
Patent Cooperation Treaty, International Searching Authority, International Preliminary Report on Patentability and Written Opinion for PCT/US2012/032108, 9 pages, report dated Oct. 8, 2013.
Patent Cooperation Treaty, International Searching Authority, International Preliminary Report on Patentability and Written Opinion for PCT/US2013/025590, 8 pages, report dated Aug. 12, 2014.
Patent Cooperation Treaty, International Searching Authority, International Preliminary Report on Patentability and Written Opinion for PCT/US2013/063034, 5 pages, report dated Apr. 7, 2015.
Patent Cooperation Treaty, International Searching Authority, International Preliminary Report on Patentability and Written Opinion for PCT/US2013/064359, 6 pages, report dated Apr. 14, 2015, opinion dated Feb. 10, 2014.
Patent Cooperation Treaty, International Searching Authority, International Preliminary Report on Patentability and Written Opinion for PCT/US2016/018233, 12 pages, report dated Aug. 22, 2017, opinion dated Apr. 29, 2016.
Patent Cooperation Treaty, International Searching Authority, International Preliminary Report on Patentability for PCT/US2017/047640, 5 pages, report dated Feb. 26, 2019, opinion dated Oct. 3, 2017.
Patent Cooperation Treaty, International Searching Authority, International Search Report for PCT/US2011/025613, 5 pages, dated Jul. 25, 2011.
Patent Cooperation Treaty, International Searching Authority, International Search Report for PCT/US2012/032108, 6 pages, dated Jan. 23, 2013.
Patent Cooperation Treaty, International Searching Authority, International Search Report for PCT/US2013/025590, 5 pages, dated May 6, 2013.
Patent Cooperation Treaty, International Searching Authority, International Search Report for PCT/US2013/063034, 3 pages, dated Nov. 15, 2013.
Patent Cooperation Treaty, International Searching Authority, International Search Report for PCT/US2013/064359, 3 pages, dated Feb. 10, 2014.
Patent Cooperation Treaty, International Searching Authority, International Search Report for PCT/US2016/018233, 4 pages, dated Apr. 29, 2016.
Patent Cooperation Treaty, International Searching Authority, International Search Report for PCT/US2017/037253, 2 pages, dated Aug. 16, 2017.
Patent Cooperation Treaty, International Searching Authority, International Search Report for PCT/US2017/047640, 3 pages, dated Oct. 30, 2017.
Patent Cooperation Treaty, International Searching Authority, International Search Report for PCT/US2017/048482, 4 pages, dated Dec. 7, 2017.
Patent Cooperation Treaty, International Searching Authority, Search Report and Written Opinion for PCT/2017/047640, 8 pages dated Oct. 3, 2017.
Patent Cooperation Treaty, International Searching Authority, Search Report and Written Opinion for PCT/US2016/18166, 10 pages, dated Apr. 29, 2016.
Patent Cooperation Treaty, International Searching Authority, Written Opinion for PCT/US2017/037253, 5 pages, dated Aug. 16, 2017.
Patent Cooperation Treaty, International Searching Authority, Written Opinion for PCT/US2017/047640, 4 pages, dated Oct. 30, 2017.
Patent Cooperation Treaty, International Searching Authority, Written Opinion for PCT/US2017/048482, 5 pages, dated Dec. 7, 2017.
Piancatelli, G., et al., "Pyridinium Chlorochromate: A Versatile Oxidant in Organic Synthesis", Synthesis 1982(4), 245-258 (1982).
Pisano, P., et al., "Plasma concentrations and pharmacokinetics of idebenone and its metabolites following single and repeated doses in young patients with mitochondrial encephalomyopathy", Eur J Clin 51(2), 167-169 (1996).
Pratt, D., et al., "5-Pyrimidinols: novel chain-breaking antioxidants more effective than phenols", J Am Chem Soc 123(19), 4625-4626 (2001).
Pubchem, "3H-Phenothiazin-3-one", CID 68485, 17 pages (Create Date Mar. 26, 2005).
Pubchem, "7-((4-nitrobenzyl)oxy)-2H-chromen-2-one", SID 164870287, create date Nov. 14, 2013, Version 1 (modified Nov. 14, 2013), retrieved Dec. 4, 2018, <https://pubchem.ncbi.nlm.nih.gov/substance/164870287/version/1>.
Pubchem, "7-((4-nitrobenzyl)oxy)-2H-chromen-2-one", SID 164870287, create date Nov. 14, 2013, Version 6 (modified Nov. 28, 2015), retrieved Dec. 4, 2018, <https://pubchem.ncbi.nlm.nih.gov/substance/164870287/version/6>.
Pubchem, "7-(dimethylamino)-3H-phenothiazin-3-one", SID 224730291, create date Feb. 2, 2015, Version 1 (modified Feb. 2, 2015), retrieved Dec. 4, 2018, <https://pubchem.ncbi.nlm.nih.gov/substance/224730291/version/1>.
Pubchem, "7-(dimethylamino)-3H-phenothiazin-3-one", SID 224730291, create date Feb. 2, 2015, Version 2 (modified Nov. 15, 2017), retrieved Dec. 4, 2018, <https://pubchem.ncbi.nlm.nih.gov/substance/224730291/version/2>.
Pubchem, "MLS002699551", SID 92763509, create date May 10, 2010, Version 1 (modified May 10, 2010), retrieved Dec. 4, 2018, <https://pubchem.ncbi.nlm.nih.gov/substance/92763509/version/1>.
Pubchem, "MLS002699551", SID 92763509, create date May 10, 2010, Version 3 (modified Mar. 1, 2012), retrieved Dec. 4, 2018, <https://pubchem.ncbi.nlm.nih.gov/substance/92763509/version/3>.

(56) References Cited

OTHER PUBLICATIONS

Quinzii, C , et al., "Respiratory chain dysfunction and oxidative stress correlate with severity of primary CoQ10 deficiency", FASEB J. 22(6), 1874-1885 (2008).
Ramasarma, T , et al., "Studies on the Electron Transport System", J Biol Chem 235(11), 3309-3314 (1960).
Ranen, N , et al., "A controlled trial of idebenone in Huntington's disease", Movement Disorders 11(5), 549-554 (1996).
Reddy, P , "Amyloid precursor protein-mediated free radicals and oxidative damage: implications for the development and progression of Alzheimer's disease", J Neurochem 96(1), 1-13 (2006, available online 2005).
Reddy, P , et al., "Are mitochondria critical in the pathogenesis of Alzheimer's disease", Brain Res Brain Res Rev 49(3), 618-632 (2005).
Robinson, B , et al., "Nonviability of cells with oxidative defects in galactose medium: A screening test for affected patient fibroblasts", Biochem. Med. Metab. Biol. 48(2), 122-126 (1992).
Robuschi, L , et al., "The Action of Light and of Photodynamic Substances on Carbohydrate Metabolism", Sperimentale 94, 99-124 (1940).
Rotig, A , et al., "Molecular insights into Friedreich's ataxia and antioxidant-based therapies", Trends Mol Med 8(5), 221-224 (2002).
Rustin, P , et al., "Idebenone treatment in Friedreich patients: one-year-long randomized placebo-controlled trial", Neurology 62(3), 524-525 (2004).
Saraste, M , "Oxidative phosphorylation at the fin de siècle", Science 283, 1488-1493 (1999).
Scavo, F , et al., "Preparation of alpha,beta-dehydro-beta-amino acid derivatives by tin-promoted addition of malonates to simple nitriles", Tetrahedron Lett 26(22), 2603-2606 (1985).
Shue, S , et al., "Targeting antioxidants to mitochondria: a new therapeutic direction", Biochim Biophys Acta 1762(2), 256-265 (2006, available online 2005).
Smith, R. , et al., "Delivery of Bioactive Molecules to Mitochondria in vivo", PNAS, vol. 100, No. 9, 5407-5412 (2003).
Drummen, G , et al., "C11-BODIPY(581/591), an oxidation-sensitive fluorescent lipid peroxidation probe: (micro) spectroscopic characterization and validation of methodology", Free Radic. Biol. Med 33(4), 473-490 (2002).
Durr, M , et al., "Clinical and genetic abnormalities in patients with Friedreich's ataxia", N Engl J Med 335(16), 1169-1175 (1996).
Ehrenberg , et al., "Membrane potential can be determined in individual cells from the nemstian distribution of cationic dyes", Biophy J 53, 785-794 (1988).
Esposti, M , et al., "The Interaction of Q Analogs, Particularly Hydroxydecyl Benzoquinone (Idebenone), with the Respiratory Complexes of Heart Mitochondria", Archives of Biochemistry and Biophysics 330(2), 395-400 (1996).
Fash, D , "Effects of alkyl side chain modification of coenzyme Q10 on mitochondrial respiratory chain function and cytoprotection", Bioorg Med Chem 21(8), 2346-2354 (2013).
Finkel, T , "Oxidant signals and oxidative stress", Curr Opin Cell Biol 15(2), 247-254 (2003).
Fiore, C , et al., "The mitochondrial ADP/ATP carrier: Structural, physiological and pathological aspects", Biochimie 80(2), 137-150 (1998).
Fisher, B , et al., "The Structure of Isomaltol", J Org Chem 29(4), 776-781 (1964).
Fridovich, I , "Fundamental aspects of reactive oxygen species, or what's the matter with oxygen?", Ann N Y Acad Sci 893(1), 13-18 (1999).
Frigerio, M , et al., "A User-Friendly Entry to 2-Iodoxybenzoic Acid (IBX)", J Org Chem 64(12), 4537-4538 (1999).
Gaetani, "Catalase and glutathione peroxidase are equally active in detoxification of hydrogen peroxide in human arythrocytes", Blood 73, 334-339 (1989).
Garcia-Rivas, D , "Ru360, a specific mitochondrial calcium uptake inhibitor, improves cardiac post-ischaemic functional recovery in rats in vivo", Br J Pharmacol 149(7), 829-837 (2006).

Genova, M , et al., "Mitochondrial production of oxygen radical species and the role of Coenzyme Q as an antioxidant", Exp Biol Med 228(5), 506-513 (2003).
Gille, L , et al., "Redox-interaction of alpha-tocopheryl quinone with isolated mitochondrial cytochrome bc1 complex", Biochem Pharmacol 68(2), 373-381 (2004).
Gillis, J , et al., "Idebenone. A review of its pharmacodynamic and pharmacokinetic properties, and therapeutic use in age-related cognitive disorders", Drugs Aging 5(2), 133-152 (1994).
Goda, S , et al., "Clinical improvement after administration of coenzyme Q10 in a patient with mitochondrial encephalomyopathy", J Neurol 234(2), 62-63 (1987).
Gold, R , et al., "Phosphorus magnetic resonance spectroscopy in the evaluation of mitochondrial myopathies: results of a 6-month therapy study with coenzyme Q", Eur Neurol 36(4), 191-196 (1996).
Goldschmidt, R , et al., "Effects of cytoprotective antioxidants on lymphocytes from representative mitochondrial neurodegenerative diseases", Bioorg. Med. Chem. 21, 969-978 (2013).
Gonzalez-Cabo , et al., "Frataxin interacts functionally with mitochondrial electron transport chain proteins", Hum. Mol. Genet. 14(15), 2091-2098 (2005).
Graier, W , et al., "Mitochondria and Ca(2+) signaling: old guests, new functions", Eur J Physiol 455, 375-396 (2007).
Green, D , et al., "Mitochondria and Apoptosis", Science 281(5381), 1309-1312 (1998).
Gregor, W , et al., "Distribution of tocopheryl quinone in mitochondrial membranes and interference with ubiquinone-mediated electron transfer", Biochem Pharmacol 71(11), 1589-1601 (2006).
Griffith, O , et al., "Potent and specific inhibition of glutathione synthesis by buthionine sulfoximine (S-n-butyl homocysteine sulfoximine)", J. Biol. Chem. 254(16), 7558-7560 (1979).
Harris, S , et al., "Structure of Vitamin B6. II", J Am Chem Soc 61(5), 1242-1244 (1939).
Hart, P , et al., "Antioxidant treatment of patients with Friedreich ataxia: four-year follow-up", Arch Neurol 62(4), 621-626 (2005).
Henze, K , et al., "Essence of mitochondria", Nature 426, 127-128 (2003).
Ihara, Y , et al., "Mitochondrial encephalomyopathy (MELAS): pathological study and successful therapy with coenzyme Q10 and idebenone", J Neurol Sci 90(3), 263-271 (1989).
Ikejiri, M , et al., "Idebenone improves cerebral mitochondrial oxidative metabolism in a patient with MELAS", Neurology 47(2), 583-585 (1996).
Infante, J , et al., "A function for the vitamin E metabolite alpha-tocopherol quinone as an essential enzyme cofactor for the mitochondrial fatty acid desaturases", FEBS Lett 446(1), 1-4 (1999).
Ingold, K , et al., "A new vitamin E analogue more active than alpha-tocopherol in the rat curative myopathy bioassay", FEBS Lett 205(1), 117-120 (1986).
Inoue, S , et al., "Improved general method of ortho alkylation of phenols using alkyl isopropyl sulfide, sulfuryl chloride, and triethylamine. An expedient synthesis of representative oxygen heterocycles and (2R,4'R,8'R)-.alpha.-tocopherol", J Org Chem 52(24), 5495-5497 (1987).
Itoh , et al., "The substitution of 5-halo-1,2,3-triazines with electrolytically generated superoxide", Tetrahedron 47(25), 4317-4324 (1991).
Iuliano, L , et al., "Protection of low density lipoprotein oxidation by the antioxidant agent IRFI005, a new synthetic hydrophilic vitamin E analogue", Free Radic Biol Med 26(7-8), 858-868 (1999).
James , et al., "Interactions of Mitochondria-targeted and Untargeted Ubiquinones with the Mitochondrial Respiratory Chain and Reactive Oxygen Species: Implications for the use of exogenous ubiquinones as therapies and experimental tools", J. Biol. Chem. 280(22), 21295-21312 (2005).
Jauslin, M , et al., "A cellular model for Friedreich Ataxia reveals small-molecule glutathione peroxidase mimetics as novel treatment strategy", Hum. Mol. Genet. 11(24), 3055-3063 (2002).
Jefferson, E , et al., "Biaryl guanidine inhibitors of in vitro HCV-IRES activity", Bioorganic Med Chem Lett 14(20), 5139-5143 (2004).

(56) References Cited

OTHER PUBLICATIONS

Jenner, P., et al., "Oxidative stress in Parkinson's disease", Ann Neurol 53(Suppl. 3), S26-S38 (2003).
Joshi, B., et al., "Benzoquinoa Derivatives. Part I. Reactions of Primary Aliphatic Amines with Embelin (2,5-Dihydroxy-3-undecyl-1,4-benzoquinone) and Di-O-methylembelin", Journal of the Chemical Society, Perkins Transactions 1: Organic and Bio-Organic Chemistry, vol. 4, p. 327-332 (1975).
Jurma, O, et al., "Decreased glutathione results in calcium-mediated cell death in PC12", Free Radic Biol Med 23(7), 1055-1066 (1997).
Kamal-Eldin, A, et al., "The chemistry and antioxidant properties of tocopherols and tocotrienols", Lipids 31(7), 671-710 (1996).
Kao, J, et al., "Chapter 5—Practical Aspects of Measuring Intracellular Calcium Signals with Fluorescent Indicators", Methods Cell Biol 40, 155-181 (1994).
Katafias, A, et al., "Oxidation of phenothiazine dyes by manganese(III) in sulfuric acid solution", Transition Met Chem 36(8), 801-809 (2011).
Katsuki, T, et al., "The first practical method for asymmetric epoxidation", J Am Chem Soc 102(18), 5974-5976 (1980).
Kelso, G, et al., "Selective targeting of a redox-active ubiquinone to mitochondria within cells: antioxidant and antiapoptotic properties", J Biol Chem 276(7), 4588-4596 (2001, available online 2000).
Khdour, O, et al., "An acetate prodrug of a pyridinol-based vitamin E analogue", Pharm. Res 28(11), 2896-2909 (2011).
Khdour, O, et al., "An Optimized Pyrimidinol Multifunctional Radical Quencher", ACS Med Chem Lett 4(8), 724-729 (2013).
Kim, B, et al., "Efficient Synthesis of 4,5,6-Trisubstituted-2-aminopyrimidines", Bull Korean Chem Soc 30(9), 2107-2110 (2009).
Kim, H, et al., "Lipid-Soluble 3-Pyridinol Antioxidants Spare α-Tocopherol and Do Not Efficiently Mediate Peroxidation of Cholesterol Esters in Human Low-Density Lipoprotein", J Med Chem 48(22), 6787-6789 (2005).
Kohar, I, et al., "Is α-tocopherol a reservoir for α-tocopheryl hydroquinone?", Free Radic Biol Med 19(2), 197-207 (1995).
Abe, K, et al., "Marked Reduction in CSF Lactate and Pyruvate Levels After CoQ Therapy in a Patient with Mitochondrial Myopathy, Encephalopathy, Lactic Acidosis and Stroke-like Episodes (MELAS)", Acta Neural Scand 83 (6), 356-359 (1991).
Acre, P, et al., "A Strategy for Suppressing Redox Stress within Mitochondria", ACS Medicinal Chemistry Letters 2 (8), 608-613 (2011).
Acre, P, et al., "Analysis of the structural and mechanistic factors in antioxidants that preserve mitochondrial function and confer cytoprotection", Bioorganic & Medicinal Chemistry 20(17), 5188-5201 (2012).
Adkins, J, et al., "Idebenone: A Review of its Use in Mild to Moderate Alzheimer's Disease", CNS Drugs 9(5), 403-419 (1998).
Aguer, C, et al., "Galactose enhances oxidative metabolism and reveals mitochondrial dysfunction in human primary muscle cells", PLoS One 6(12), e28536 (2011).
Alam, M, et al., "Cytoprotective pyridinol antioxidants as potential therapeutic agents for neurodegenerative and mitochondrial diseases", Bioorganic & Medicinal Chemistry 22(17), 4935-4947 (2014).
Armstrong, J, et al., "Cysteine starvation activates the redox-dependent mitochondrial permeability transition in retinal pigment epithelial cells", Invest Ophthalmol Vis Sci 45(11), 4183-4189 (2004).
Armstrong, J, et al., "Does oxidative stress contribute to the pathology of Friedreich's ataxia? A radical question", The FASEB Journal 24(7), 2152-2163 (2010).
Armstrong, J, et al., "Glutathione depletion enforces the mitochondrial permeability transition and causes cell death in Bcl-2 overexpressing HL60 cells", FASEB J 16(10), 1263-1265 (2002).
Armstrong, J, et al., "The coenzyme Q10 analog decylubiquinone inhibits the redox-activated mitochondrial permeability transition: role of mitochondrial respiratory chain complex III", J Biol Chem 278(49), 49079-49084 (2003).

Asin-Cayuela, J, et al., "Fine-tuning the hydrophobicity of a mitochondria-targeted antioxidant", FEBS Lett 571 (1-3), 9-16 (2004).
Atamna, H, et al., "Methylene blue delays cellular senescence and enhances key mitochondrial biochemical pathways", FASEB J 22(3), 703-712 (2008, available online 2007).
Barbiroli, B, et al., "Coenzyme Q10 improves mitochondrial respiration in patients with mitochondrial cytopathies. An in vivo study on brain and skeletal muscle by phosphorous magnetic resonance spectroscopy", Cell Mol Biol 43(5), 741-749 (1997).
Barnham, K, et al., "Neurodegenerative diseases and oxidative stress", Nat Rev Drug Discov 3(3), 205-214 (2004).
Benard, G, et al., "Ultrastructure of the mitochondrion and its bearing on function and bioenergetics", Antioxid Redox Signal 10(8), 1313-1342 (2008).
Bencze, et al., "Human frataxin: iron and ferrochelatase binding surface", J.C.S. Chem. Commun. 14(18), 1798-1800 (2007).
Bendahan, D, et al., "31P NMR spectroscopy and ergometer exercise test as evidence for muscle oxidative performance improvement with coenzyme Q in mitochondrial myopathies", Neurology 42(6), 1203-1208 (1992).
Boduszek, et al., "A New Method for the Preparation of Pyridine-4-phosphonic Acids", Synthesis 1979(6), 452-453 (1979).
Bradley, et al., "Clinical, biochemical and molecular genetic correlations in Friedreich's ataxia", Hum. Mol. Genet. 9(2), 275-282 (2000).
Bras, M, et al., "Programmed cell death via mitochondria: different modes of dying", Biochemistry (Mosc) 70(2), 231-239 (2005).
Bresolin, N, et al., "Clinical and biochemical correlations in mitochondrial myopathies treated with coenzyme Q10", Neurology 38(6), 892-898 (1988).
Bresolin, N, et al., "Ubidecarenone in the treatment of mitochondrial myopathies: a multi-center double-blind trial", J Neuro Sci 100(1-2), 70-78 (1990).
Briere, J-J, et al., "Quinone analogues regulate mitochondrial substrate competitive oxidation", Biochemical and Biophysical Research Communications 316(4), 1138-1142 (2004).
Brigelius-Flohe, R, et al., "Vitamin E: function and metabolism", FASEB J 13(10), 1145-1155 (1999).
Brown, R, et al., "Potential Antimalarials in the 4-Dialkylaminomethyl-2-Methyl-3-Pyridol Series", J Org Chem 11(4), 388-389 (1946).
Bulteau, et al., "Frataxin Acts as an Iron Chaperone Protein to Modulate Mitochondrial Aconitase Activity", Science 305(5681), 242-245 (2004).
Burton, G, et al., "Vitamin E: application of the principles of physical organic chemistry to the exploration of its structure and function", Acc Chem Res 19(7), 194-201 (1986).
Cadenas, E, et al., "Mitochondrial free radical generation, oxidative stress, and aging", Free Radic Biol Med 29(3-4), 222-230 (2000).
Cadenas, E, et al., "Mitochondrial free radical production and cell signaling", Mol Aspects Med 25(1-2), 17-26 (2004).
Cai, X, et al., "Simplified bicyclic pyridinol analogues protect mitochondrial function", Bioorganic & Medicinal Chemistry 20(11), 3584-3595 (2012).
Calabrese, V, et al., "Oxidative stress, mitochondrial dysfunction and cellular stress response in Friedreich's ataxia", J Neuro Sci 233(1-2), 145-162 (2005).
Calza, P, et al., "Light-induced transformations of fungicides on titanium dioxide: pathways and by-products evaluation using the LC-MS technique", Int J Environ Anal Chem 86(3-4), 265-275 (2006).
Campuzano, et al., "Frataxin is Reduced in Friedreich Ataxia Patients and is Associated with Mitochondrial Membranes", Hum. Mol. Genet. 6(11), 1771-1780 (1997).
Campuzano, et al., "Friedreich's ataxia: autosomal recessive disease caused by an intronic GAA triplet repeat axpansion", Science 271(5254), 1423-1427 (1996).
Castilho, R, et al., "Oxidative Damage of Mitochondria Induced by Fe(II)Citrate Is Potentiated by Ca2+ and Includes Lipid Peroxidation and Alterations in Membrane Proteins", Arch Biochem Biophys 308(1), 158-163 (1994).

(56) References Cited

OTHER PUBLICATIONS

Chevalier, A., et al., "Influence of substituent heteroatoms on the cytoprotective properties of pyrimidinol antioxidants", Bioorganic & Medicinal Chemistry 25(5), 1703-1716 (2017).

Chevalier, A., et al., "Optimization of pyrimidinol antioxidants as mitochondrial protective agents: ATP production and metabolic stability", Bioorganic & Medicinal Chemistry 24, 5206-5220 (2016).

Chua, Y., et al., "Oltipraz-induced phase 2 enzyme response conserved in cells lacking mitochondrial DNA", Biochem Biophys Res Commun 337(1), 375-381 (2005).

Chung, K., et al., "New 4-hydroxypyridine and 4-hydroxyquinoline derivatives as inhibitors of NADH-ubiquinone reductase in the respiratory chain", Z Naturforsch C 44(7-8), 609-616 (1989).

Corey, E., et al., "New and highly effective method for the oxidation of primary and secondary alcohols to carbonyl compounds", J Am Chem Soc 94(21), 7586-7587 (1972).

Corey, E., et al., "Pyridinium chlorochromate. An efficient reagent for oxidation of primary and secondary alcohols to carbonyl compounds", Tetrahedron Lett 16(31), 2647-2650 (1975).

Crompton, M., "The mitochondrial permeability transition pore and its role in cell death", Biochem J 341(2), 233-249 (1999).

D'Alessio, M., et al., "Apoptotic GSH extrusion is associated with free radical generation", Ann N Y Acad Sci 1010 (1), 449-452 (2003).

De Hingh, Y., et al., "Direct measurement of lipid peroxidation in submitochondrial particles", Biochemistry 34(39), 12755-12760 (1995).

Dimauro, et al., "Mitochondrial DNA mutations in human disease", Am. J. Med Genet. 106(1), 18-26 (2001).

Dimauro, S., et al., "Mitochondrial disorders in the nervous system", Annu Rev Neurosci 31, 91-123 (2008).

Di Prospero, N., et al., "Safety, Tolerability, and Pharmacokinetics of High-Dose Idebenone in Patients With Friedreich Ataxia", Archives of Neurology 64(6), 803-808 (2007).

Droge, W., "Free Radicals in the Physiological Control of Cell Function", Physiol Rev 82(1), 47-95 (2002).

\* cited by examiner

SUBSTITUTED PYRIMIDINE COMPOUNDS AS MULTIFUNCTIONAL RADICAL QUENCHERS AND THEIR USES

RELATED APPLICATIONS

This application claims priority to U.S. Provisional Application No. 62/379,658 that was filed on 25 Aug. 2016. The entire content of the applications referenced above are hereby incorporated by reference herein.

BACKGROUND OF THE INVENTION

The critical function of mitochondria in eukaryotic cells is now well defined (Henze, K., et al. *Nature* 2003, 426, 127; Saraste, M. W. *Science* 1999, 283, 1488; McBride, H. M., et al. *Curr. Biol.* 2006, 16, R551; Newmeyer, D. D., et al. Cell 2003, 112, 481; Graier, W. F. *Eur. J. Physiol.* 2007, 455, 375; Bras, M., et al. Biochemistry (Moscow) 2005, 70, 231; and Fiore, C., et al. *Biochimie* 1998, 80, 13). Their essential role in energy metabolism through the production of adenosine-5'-triphosphate (ATP) is one of the main points which can affect the fate of cells (Saraste, M. W. *Science* 1999, 283, 1488; and McBride, H. M., et al. *Curr. Biol.* 2006, 16, R551). This ATP production is the result of conversion of ADP in mitochondrial complex V. This process involves protons transported from the inner mitochondrial membrane to the intermembrane space which is coupled with an electron flow through mitochondrial complexes I-IV. This process is called oxidative phosphorylation (OXPHOS). The decline in mitochondrial function is connected to aging, neurodegenerative diseases and many complex mitochondrial diseases (Markesbery, W. R., et al. *Brain Pathol.* 1999, 9, 133; Calabrese, V., et al. *Neurol. Sci.* 2005, 233, 145; Lin, M. T., et al. *Nature* 2006, 443, 787; DiMauro, S., et al. *Annu. Rev. Neurosci.* 2008, 31, 91; and Armstrong, J. S., et al. *FASEB J.* 2010, 24, 2152). Currently there is a need for new compounds that protect mitochondrial function.

SUMMARY OF THE INVENTION

The invention provides compounds that protect the mitochondrial function. Accordingly the invention provides a compound of formula I:

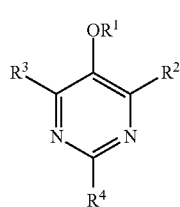

formula I wherein $R^1$ is hydrogen or $C_{1-6}$ alkyl;

$R^2$ is $C_{1-20}$ alkyl, $C_{2-20}$ alkenyl or $C_{2-20}$ alkynyl, wherein the $C_{1-20}$ alkyl, $C_{2-20}$ alkenyl and $C_{2-20}$ alkynyl are optionally substituted with one or more groups independently selected from —F, —Cl, —Br, —I, —OR$^a$, —SR$^a$, —N(R$^a$)$_2$, oxo, —NO$_2$ and —CN;

$R^3$ is —OR$^5$ or —NR$^6$R$^7$;

$R^4$ is —OR$^8$ or —NR$^9$R$^{10}$;

$R^5$ is $C_{3-10}$ cycloalkyl or $C_{1-8}$ alkyl; wherein $C_{3-10}$ cycloalkyl and $C_{1-8}$ alkyl are optionally substituted with one or more groups independently selected from $C_{1-4}$ alkyl, $C_{1-4}$ haloalkyl, —F, —Cl, —Br, —I, —OR$^b$, —SR$^b$, —N(R$^b$)$_2$, oxo, —NO$_2$ and —CN;

$R^6$ is $C_{1-6}$ alkyl, $C_{2-6}$ alkenyl or $C_{2-6}$ alkynyl, and wherein the $C_{1-6}$ alkyl, $C_{2-6}$ alkenyl and $C_{2-6}$ alkynyl are optionally substituted with one or more groups independently selected from —F, —Cl, —Br, —I, —OR$^c$, —SR$^c$, —N(R$^c$)$_2$, oxo, —NO$_2$ and —CN; $R^7$ is $C_{1-6}$ alkyl, $C_{2-6}$ alkenyl or $C_{2-6}$ alkynyl, and wherein the $C_{1-6}$ alkyl, $C_{2-6}$ alkenyl and $C_{2-6}$ alkynyl are optionally substituted with one or more groups independently selected from —F, —Cl, —Br, —I, —OR$^d$, —SR$^d$, —N(R$^d$)$_2$, oxo, —NO$_2$ and —CN; or $R^6$ and $R^7$ taken together with the nitrogen to which they are attached form a 3-10 membered heterocycle that is optionally substituted with one or more groups independently selected from $C_{1-4}$ alkyl, $C_{1-4}$ haloalkyl, —F, —Cl, —Br, —I, —OR$^e$, —SR$^e$, —N(R$^e$)$_2$, oxo, —NO$_2$ and —CN;

$R^8$ is $C_{3-10}$ cycloalkyl or $C_{1-8}$ alkyl; wherein $C_{3-10}$ cycloalkyl and $C_{1-8}$ alkyl are optionally substituted with one or more groups independently selected from $C_{1-4}$ alkyl, $C_{1-4}$ haloalkyl, —F, —Cl, —Br, —I, —OR$^f$, —SR$^f$, —N(R$^f$)$_2$, oxo, —NO$_2$ and —CN;

$R^9$ is $C_{1-6}$ alkyl, $C_{2-6}$ alkenyl or $C_{2-6}$ alkynyl, and wherein the $C_{1-6}$ alkyl, $C_{2-6}$ alkenyl and $C_{2-6}$ alkynyl are optionally substituted with one or more groups independently selected from —F, —Cl, —Br, —I, —OR$^g$, —SR$^g$, —N(R$^g$)$_2$, oxo, —NO$_2$ and —CN; $R^{10}$ is $C_{1-6}$ alkyl, $C_{2-6}$ alkenyl or $C_{2-6}$ alkynyl, and wherein the $C_{1-6}$ alkyl, $C_{2-6}$ alkenyl and $C_{2-6}$ alkynyl are optionally substituted with one or more groups independently selected from —F, —Cl, —Br, —I, —OR$^h$, —SR$^h$, —N(R$^h$)$_2$, oxo, —NO$_2$ and —CN; or $R^9$ and $R^{10}$ taken together with the nitrogen to which they are attached form a 3-10 membered heterocycle that is optionally substituted with one or more groups independently selected from $C_{1-4}$ alkyl, $C_{1-4}$ haloalkyl, —F, —Cl, —Br, —I, —OR$^i$, —SR$^i$, —N(R$^i$)$_2$, oxo, —NO$_2$ and —CN;

each $R^a$ is independently hydrogen or $C_{1-4}$ alkyl; or two $R^a$ taken together with the nitrogen to which they are attached form pyrrolidinyl, piperidinyl, piperazinyl or morpholinyl;

each $R^b$ is independently hydrogen or $C_{1-4}$ alkyl; or two $R^b$ taken together with the nitrogen to which they are attached form pyrrolidinyl, piperidinyl, piperazinyl or morpholinyl;

each $R^c$ is independently hydrogen or $C_{1-4}$ alkyl; or two $R^c$ taken together with the nitrogen to which they are attached form pyrrolidinyl, piperidinyl, piperazinyl or morpholinyl;

each $R^d$ is independently hydrogen or $C_{1-4}$ alkyl; or two $R^d$ taken together with the nitrogen to which they are attached form pyrrolidinyl, piperidinyl, piperazinyl or morpholinyl;

each $R^e$ is independently hydrogen or $C_{1-4}$ alkyl; or two $R^e$ taken together with the nitrogen to which they are attached form pyrrolidinyl, piperidinyl, piperazinyl or morpholinyl;

each $R^f$ is independently hydrogen or $C_{1-4}$ alkyl; or two $R^f$ taken together with the nitrogen to which they are attached form pyrrolidinyl, piperidinyl, piperazinyl or morpholinyl;

each $R^g$ is independently hydrogen or $C_{1-4}$ alkyl; or two $R^g$ taken together with the nitrogen to which they are attached form pyrrolidinyl, piperidinyl, piperazinyl or morpholinyl;

each $R^h$ is independently hydrogen or $C_{1-4}$ alkyl; or two $R^h$ taken together with the nitrogen to which they are attached form pyrrolidinyl, piperidinyl, piperazinyl or morpholinyl; and each $R^i$ is independently hydrogen or $C_{1-4}$ alkyl; or two $R^i$ taken together with the nitrogen to which they are attached form pyrrolidinyl, piperidinyl, piperazinyl or morpholinyl;

or a pharmaceutically acceptable salt thereof.

The invention also provides a pharmaceutical composition comprising a compound of formula I or a pharmaceutically acceptable salt thereof, and a pharmaceutically acceptable carrier.

The invention also provides a method for treating mitochondrial disease, neurodegenerative disease, cardiovascular disease, cancer or diabetes in an animal comprising administering a compound of formula I or a pharmaceutically acceptable salt thereof to the animal.

The invention also provides a compound of formula I or a pharmaceutically acceptable salt thereof for use in medical therapy.

The invention also provides a compound of formula I or a pharmaceutically acceptable salt thereof for the prophylactic or therapeutic treatment of mitochondrial disease, neurodegenerative disease, cardiovascular disease, cancer or diabetes.

The invention also provides the use of a compound of formula I or a pharmaceutically acceptable salt thereof to prepare a medicament for treating mitochondrial disease, neurodegenerative disease, cardiovascular disease, cancer or diabetes in an animal (e.g. a mammal such as a human).

The invention also provides processes and intermediates disclosed herein that are useful for preparing a compound of formula I or a salt thereof.

DETAILED DESCRIPTION

Figure 1:
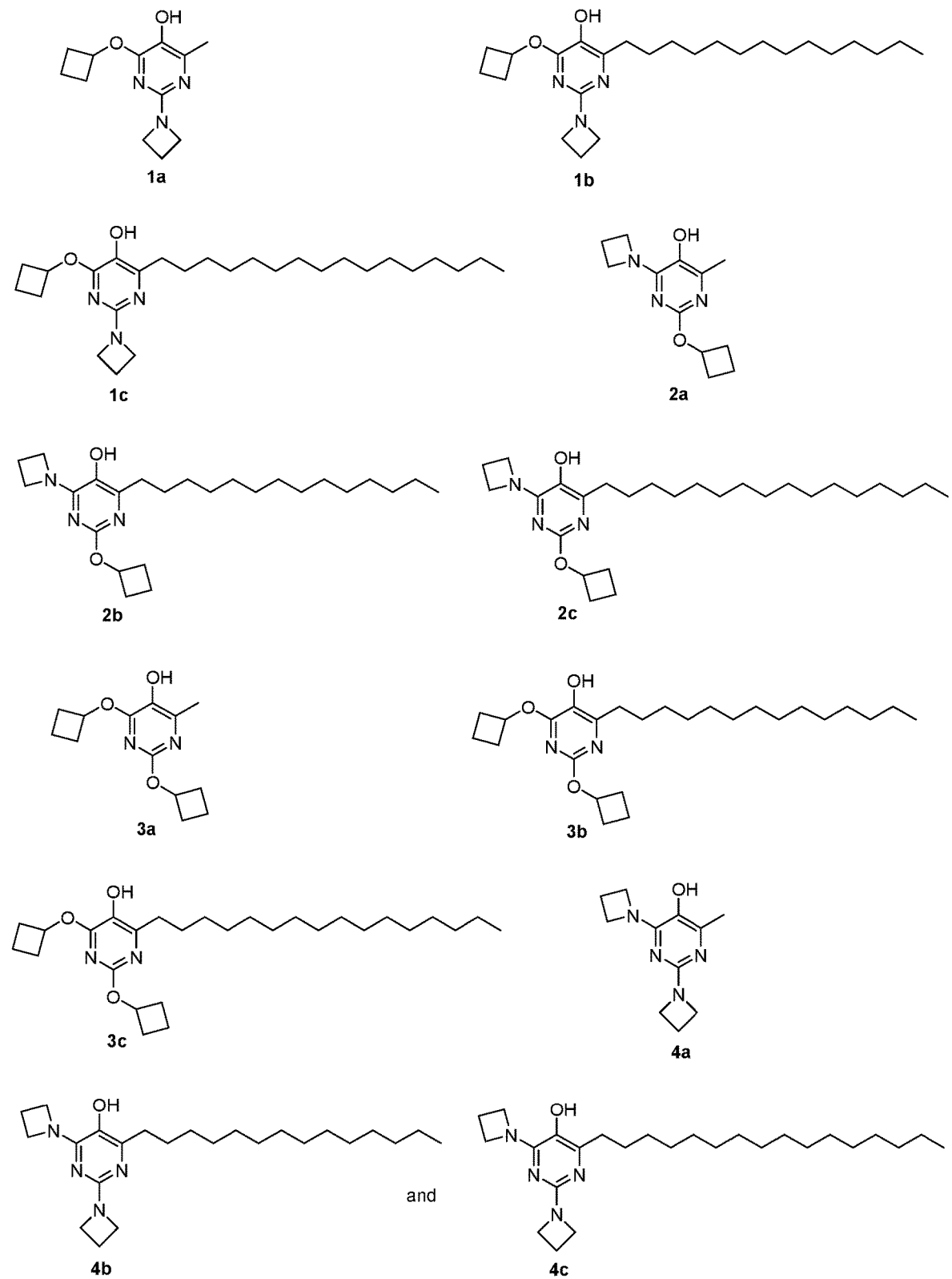
FIG. 1 illustrates the chemical structures of the representative compounds of formula I (compounds 1a-1c, 2a-2c, 3a-3c and 4a-4c).

The term "alkyl", by itself or as part of another substituent, means, unless otherwise stated, a straight or branched chain hydrocarbon radical, having the number of carbon atoms designated (i.e., $C_{1-6}$ means one to six carbons). Non limiting examples of "alkyl" include methyl, ethyl, propyl, isopropyl, butyl, iso-butyl, sec-butyl, pentyl, 3-pentyl, hexyl and decyl.

The term "alkenyl" refers to an unsaturated alkyl radical having one or more double bonds. Non limiting examples of "alkenyl" include vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 2,4-pentadienyl. Similarly, the term "alkynyl" refers to an unsaturated alkyl radical having one or more triple bonds.

The term "haloalkyl" means an alkyl that is optionally substituted with one or more halo. Non limiting examples of "haloalkyl" include iodomethyl, bromomethyl, chloromethyl, fluoromethyl, trifluoromethyl, 2-chloroethyl, 2-fluoroethyl, 2,2,2-trifluoroethyl 2,2-difluoroethyl and pentafluoroethyl.

The term "cycloalkyl" refers to a saturated or a partially unsaturated all carbon ring having 3 to 10 carbon atoms. As used herein, "cycloalkyl" is also meant to refer to bicyclic, polycyclic and spirocyclic hydrocarbon ring system, such as, for example, bicyclo[2.2.1]heptane, pinane, bicyclo[2.2.2] octane, adamantane, norborene, spirocyclic C5-12 alkane, etc.

The term "heterocycle" refers to a saturated or partially unsaturated ring system radical having the overall having from 3-10 ring atoms that contain from one to five heteroatoms selected from N, O, and S. Unless otherwise stated, a "heterocycle" ring can be a monocyclic, a bicyclic, spirocyclic or a polycylic ring system. Non limiting examples of "heterocycle" rings include pyrrolidine, piperidine, N-methylpiperidine, imidazolidine, pyrazolidine, butyrolactam, valerolactam, imidazolidinone, hydantoin, dioxolane, phthalimide and piperidine.

The terms "treat" and "treatment" refer to both therapeutic treatment and/or prophylactic treatment or preventative measures, wherein the object is to prevent or slow down (lessen) an undesired physiological change or disorder, such as, for example, the development or spread of cancer. For purposes of this invention, beneficial or desired clinical results include, but are not limited to, alleviation of symptoms, diminishment of extent of disease or disorder, stabilized (i.e., not worsening) state of disease or disorder, delay or slowing of disease progression, amelioration or palliation of the disease state or disorder, and remission (whether partial or total), whether detectable or undetectable. "Treatment" can also mean prolonging survival as compared to expected survival if not receiving treatment. Those in need of treatment include those already with the disease or disorder as well as those prone to have the disease or disorder or those in which the disease or disorder is to be prevented.

The phrase "effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. For cancer therapy, efficacy can, for example, be measured by assessing the time to disease progression (TTP) and/or determining the response rate (RR).

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

In one embodiment, $R^1$ is hydrogen.
In one embodiment, $R^2$ is $C_{1-20}$ alkyl.
In one embodiment, $R^2$ is $C_{10-20}$ alkyl.
In one embodiment, $R^2$ is methyl, tetradecyl or hexadecyl.
In one embodiment, $R^5$ is cyclobutyl.
In one embodiment, $R^6$ and $R^7$ taken together with the nitrogen to which they are attached form a 3-10 membered heterocycle that is optionally substituted with one or more groups independently selected from $C_{1-4}$ alkyl, $C_{1-4}$ haloalkyl, —F, —Cl, —Br, —I, —OR$^e$, —SR$^e$, —N(R$^e$)$_2$, oxo, —NO$_2$ and —CN.

In one embodiment, $R^6$ and $R^7$ taken together with the nitrogen to which they are attached form

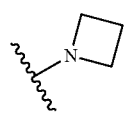

In one embodiment, $R^9$ and $R^{10}$ taken together with the nitrogen to which they are attached form a 3-10 membered heterocycle that is optionally substituted with one or more groups independently selected from $C_{1-4}$ alkyl, $C_{1-4}$haloalkyl, —F, —Cl, —Br, —I, —OR$^i$, —SR$^i$, —N(R$^i$)$_2$, oxo, —NO$_2$ and —CN.

In one embodiment, $R^9$ and $R^{10}$ taken together with the nitrogen to which they are attached form

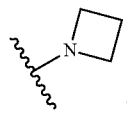

In one embodiment, $R^3$ is —OR$^5$ and $R^4$ is —NR$^9$R$^{10}$ or $R^3$ is —NR$^6$R$^7$ and $R^4$ is —OR$^8$.

In one embodiment, the compound is a compound of formula Ia:

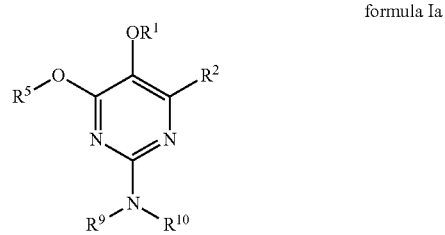

formula Ia or a pharmaceutically acceptable salt thereof.

In one embodiment, $R^2$ in the compound of formula Ia is $C_{10-20}$ alkyl.

In one embodiment, $R^9$ and $R^{10}$ in the compound of formula Ia taken together with the nitrogen to which they are attached form a 3-10 membered heterocycle that is optionally substituted with one or more groups independently selected from $C_{1-4}$ alkyl, $C_{1-4}$ haloalkyl, —F, —Cl, —Br, —I, —OR$^i$, —SR$^i$, —N(R$^i$)$_2$, oxo, —NO$_2$ and —CN.

In one embodiment, the compound is a compound of formula Ib:

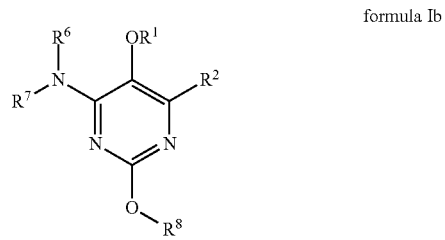

formula Ib or a pharmaceutically acceptable salt thereof.

In one embodiment, $R^2$ in the compound of formula Ia is $C_{10-20}$ alkyl.

In one embodiment, $R^6$ and $R^7$ in the compound of formula Ia taken together with the nitrogen to which they are attached form a 3-10 membered heterocycle that is optionally substituted with one or more groups independently selected from $C_{1-4}$ alkyl, $C_{1-4}$ haloalkyl, —F, —Cl, —Br, —I, —OR$^i$, —SR$^i$, —N(R$^i$)$_2$, oxo, —NO$_2$ and —CN.

In one embodiment, R³ is
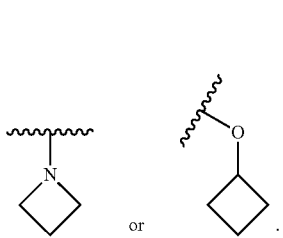 [SMILES: *N1CCC1 ; *OC1CCC1] or 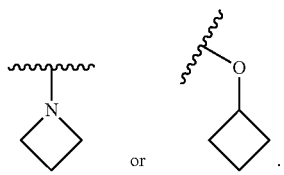 [SMILES: *N1CCC1 ; *OC1CCC1]
In one embodiment, R⁴ is
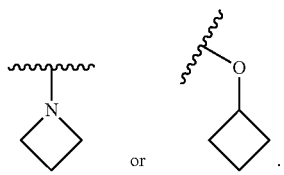 [SMILES: *N1CCC1 ; *OC1CCC1] or
In one embodiment, the compound is selected from the group consisting of:
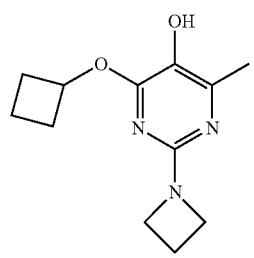
1a
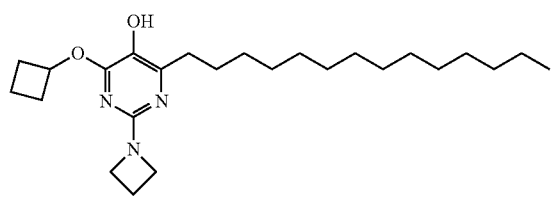
1b
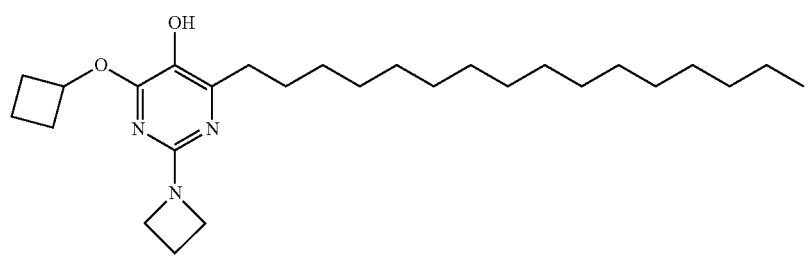
1c
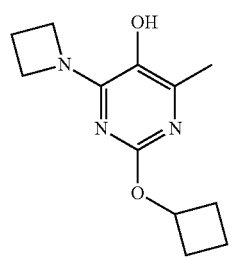
2a
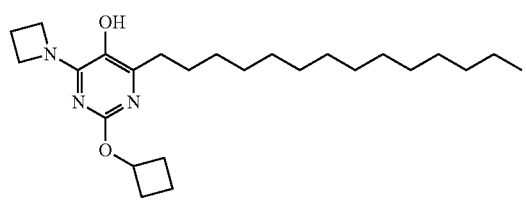
2b
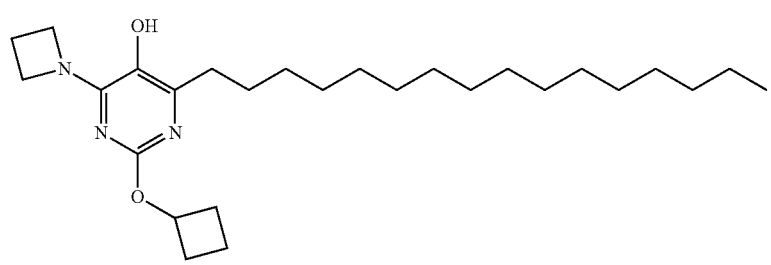
2c
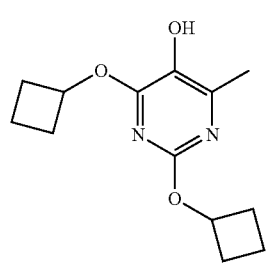
3a
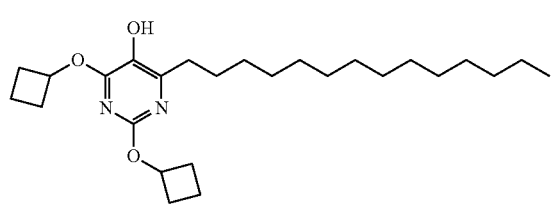
3b

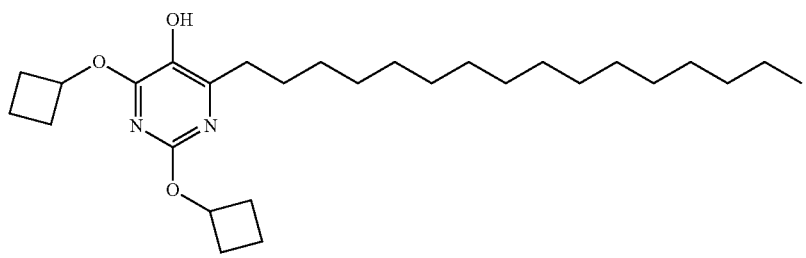

3c

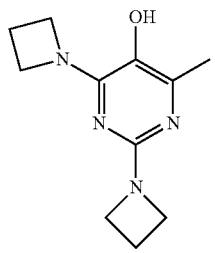

4a

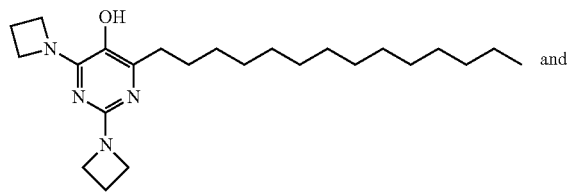

4b and

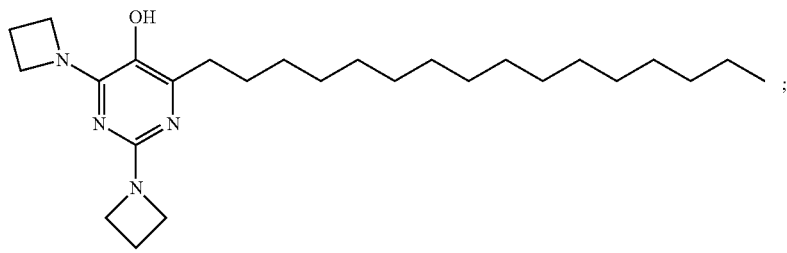

4c

;

and pharmaceutically acceptable salts thereof.

In one embodiment, the neurodegenerative disease is amyotrophic lateral sclerosis (ALS), Alzheimer's disease (AD), Parkinson's disease (PD) or Friedreich's ataxia (FRDA).

In one embodiment, the invention provides a method of quenching lipid peroxidation and/or suppress reactive oxygen species (ROS) and/or preserving mitochondrial membrane potential and/or augmenting ATP production in an animal comprising administering to the animal an effective amount of compound of formula (I) or a pharmaceutically acceptable salt thereof.

In one embodiment, the invention also provides a method of quenching lipid peroxidation and/or suppress reactive oxygen species (ROS) and/or preserving mitochondrial membrane potential and/or augmenting ATP production in a cell in vitro comprising contacting the cell with an effective amount of compound of formula (I) or a pharmaceutically acceptable salt thereof.

In one embodiment, the invention provides a compound of formula (I) or a pharmaceutically acceptable salt thereof for use in quenching lipid peroxidation and/or suppress reactive oxygen species (ROS) and/or preserving mitochondrial membrane potential and/or augmenting ATP production.

In one embodiment, the invention provides the use of a compound of formula (I) or a pharmaceutically acceptable salt thereof for the manufacture of a medicament for quenching lipid peroxidation and/or suppress reactive oxygen species (ROS) and/or preserving mitochondrial membrane potential and/or augmenting ATP production.

Processes and intermediates useful for preparing compounds of formula I are provided as further embodiments of the invention and are illustrated by the following procedures in which the meanings of the generic radicals are as given above unless otherwise qualified.

Compounds of formula (I) may be prepared by the process illustrated in Schemes 1-3. Representative compounds of formula (I) are compounds 1a-c, 2a-c, 3a-c and 4a-c (FIG. 1).

The synthesis began with an aromatic nucleophilic substitution reaction of 2,4-dichloro-6-methylpyrimidine and cyclobutanol. Two regioisomers (5a and 5b) in an almost equimolar ratio were afforded, resulting respective yields of 35 and 34%. The use of the 2-(azetidin-1-yl)-4-cyclobutoxy-6-methylpyrimidine (5a) gave access to a first family of regioisomers. First by bromination or the pyrimidinol ring in position 5, the resulting aryl bromide 6 was hydroxylated via a sequence of boronylation-oxydation to obtain the redox core 1a of this family of regioisomers. An alkylation beforehand of the compound 5a to incorporate the 14 and 16 carbons side chains led to the compounds 7a and 7b with respectively 76 and 84% yields. The bromination followed by the hydroxylation step gave the quenchers 1b and 1c to complete a set of 3 quenchers for a first regioisomer family structurally similar to the MRQ previously reported by our team. The same sequence was applied to the compound 5b and the preparation of 3 new analogues was achieved as the results of what the Redox core 2a and the 14 and 16 carbons analogues 2b and 2b were obtained with respectively 55, 56 and 56% overall yields starting from the compound 5b. This completed a set of 6 quenchers in which the two isomers of alkoxy-aminyl pyrimidinols were presented in 3 different forms (1, 14 and 16 carbons).

Scheme 1. Synthesis of compounds 1a-c and 2a-c
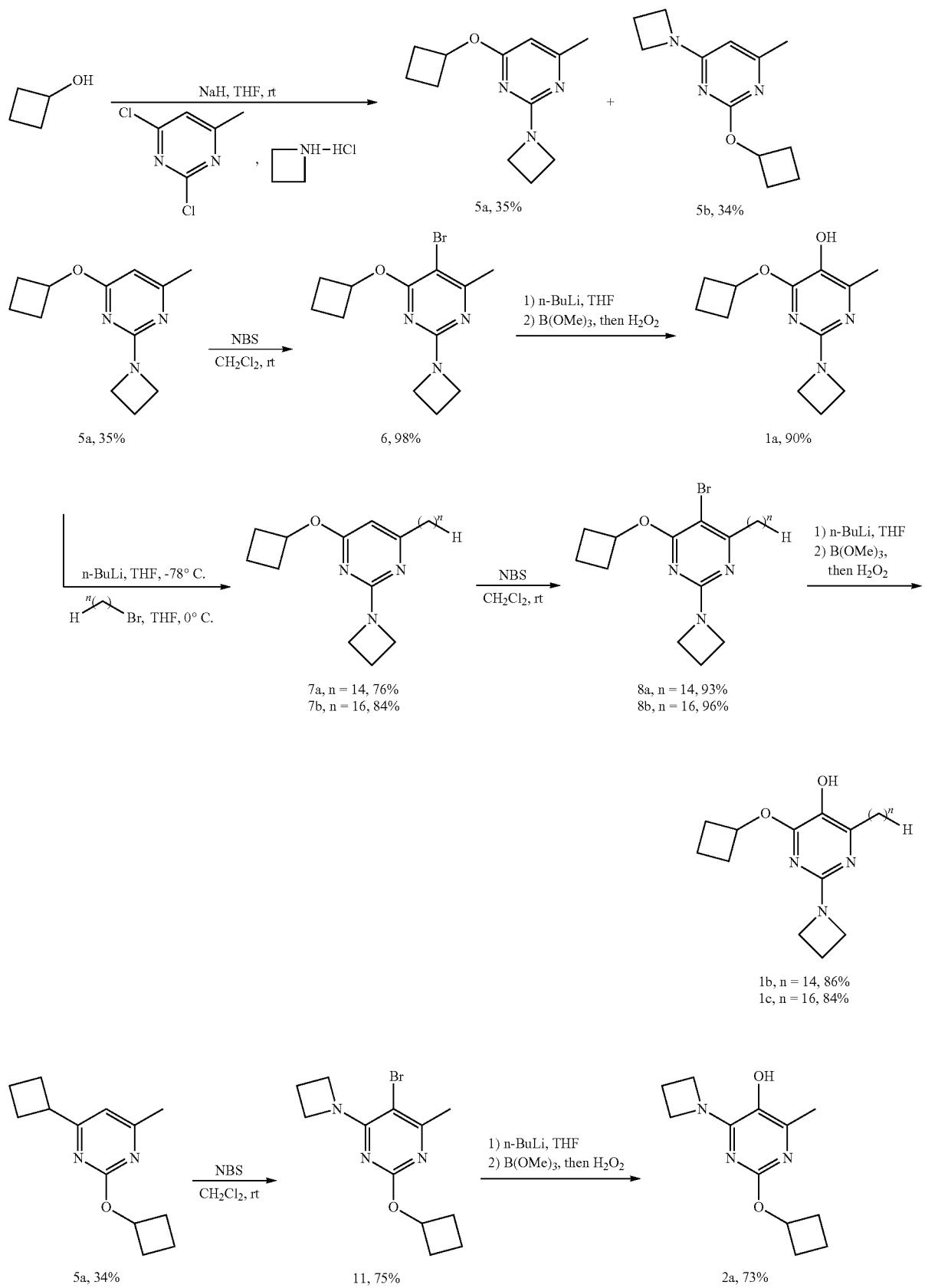

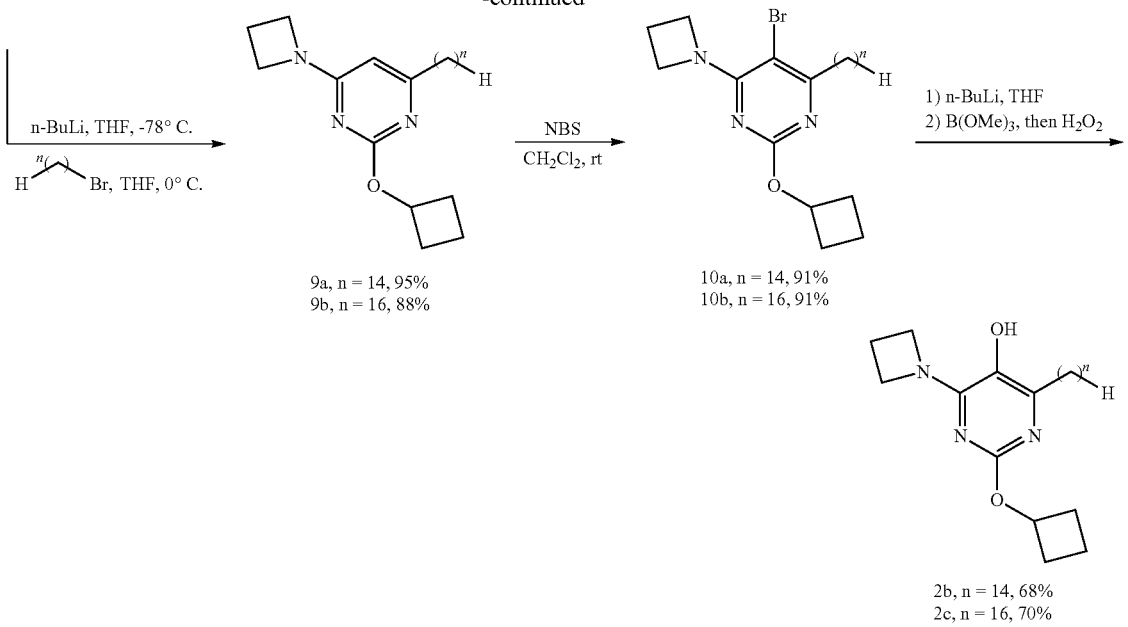

In Scheme 2, the use of an excess of cyclobutanol during the first step enabled the synthesis of the di-cyclobutoxy-6-methylpyrimidine (12) in 91% yield which has been used for the preparation of three new compounds following the same synthetic strategy. Redox core 3a was then obtained in 58% overall yield starting from the 2,4-dichloro-6-methylpyrimidine. After alkylation of the compound 12 followed by the bromination and hydroxylation steps, the 14 and 16 carbon analogues of the di-alkoxypyrimidinol family (3b and 3c) were obtained in 33 and 41% overall yields, respectively.

Scheme 2. Synthesis of compounds 3a-c

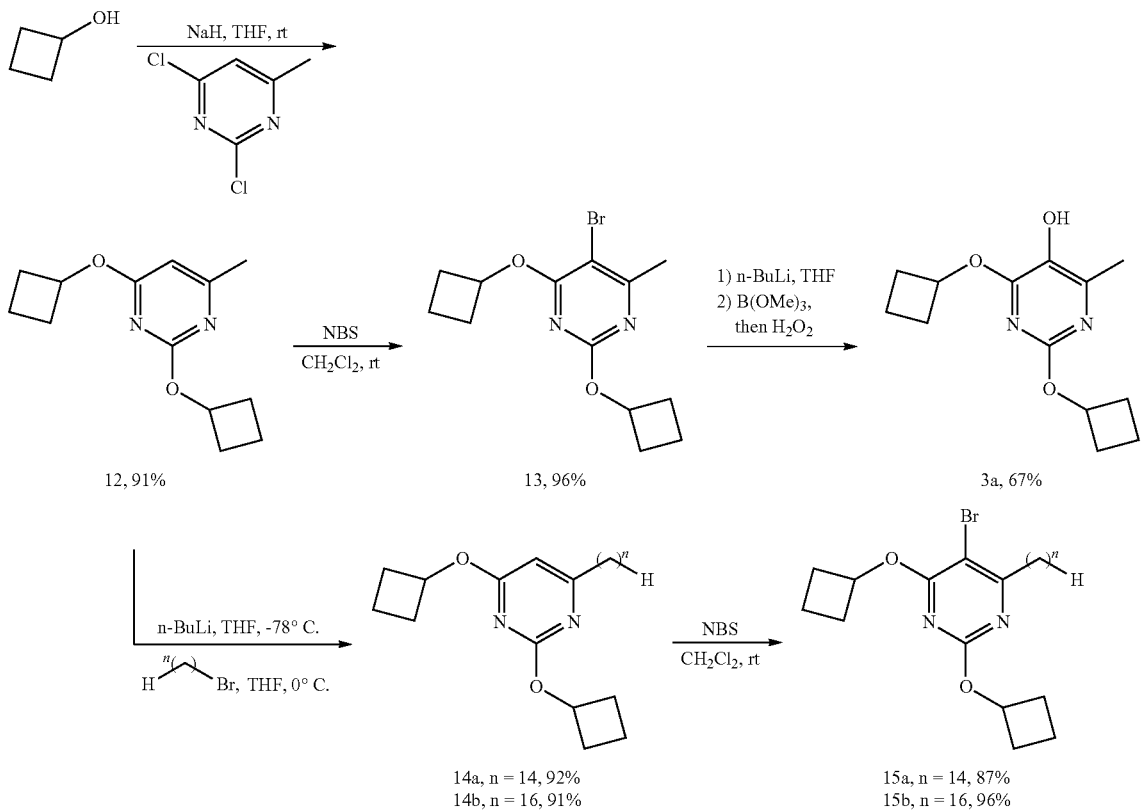

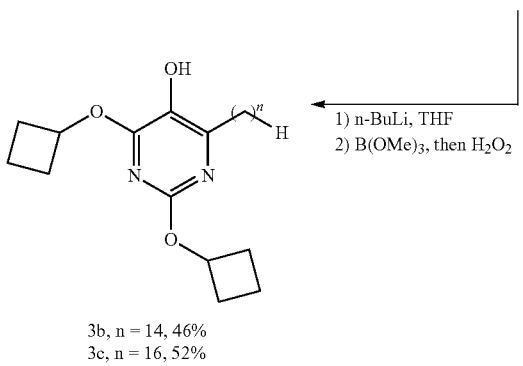

3b, n = 14, 46%
3c, n = 16, 52%

In Scheme 3, the preparation of the (2,4)-di-azetidinyl-6-methylpyrimidine (16) was achieved using a copper catalyzed nucleophilic substitution of both chlorine atoms of the 2,4-dichloro-6-methylpyrimidine with an excess of azetidine. The resulting compound 16, isolated in 78% yield, was then brominated to obtain the arylbromide 17 which was hydroxylated to obtain the redox core 4a in 66% yield. The 14 and 16 carbon analogues of 4a were prepared using the previously described sequence of alkylation, bromination and hydroxylation. The quenchers 4b and 4c were then recovered in 40 and 38% overall yields, respectively, starting from 2,4-dichloro-6-methylpyrimidine.

Scheme 3. Synthesis of compounds 4a-c

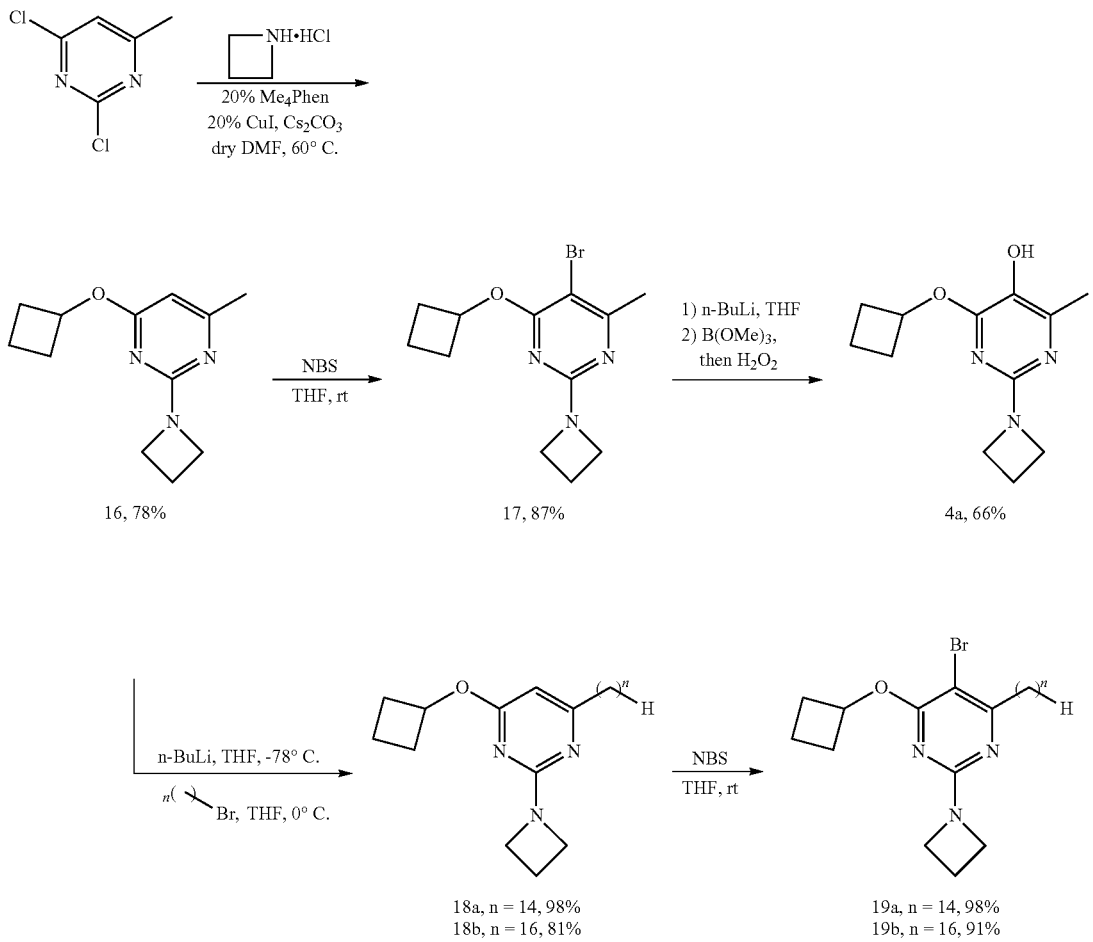

-continued

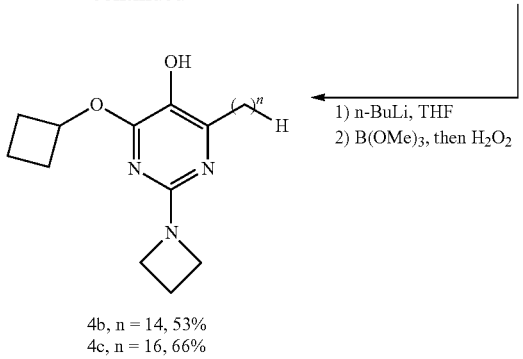

4b, n = 14, 53%
4c, n = 16, 66%

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The invention will now be illustrated by the following non-limiting Examples.

EXAMPLES

Chemistry

Anhydrous grade solvents were purchased from Sigma-Aldrich Inc. (St. Louis, Mo.) and from Fisher Scientific. Most of the chemical reagents were purchased from Sigma-Aldrich and used without further purification. ImPrPh$_2$HCl, morpholine and iodine were purchased from TCI America. Azetidine hydrochloride was purchased from Combi-Blocks. All glassware and needles were pre-dried in an oven at 120° C. prior to use. Tetrahydrofuran was distilled from sodium/benzophenone. All reactions were performed under a stream of argon. Flash column chromatography was carried out using silica gel (Silicycle R10030B, 60 Å particle size, 230-400 mesh), applying a low pressure stream of nitrogen. Analytical thin layer chromatographic separations were carried out on silica gel (60 Å particle size, 250 lm thickness, F-254, Silicycle) coated glass plates. Spots were visualized with UV light, or developed by using iodine vapor, or by immersing the plates in 2.0% anisaldehyde in ethanol/sulfuric acid/acetic acid, followed by heating with a heat gun. The NMR spectra were recorded using a 400 MHz Varian Inova instrument. Chemical shifts were reported in parts per million (ppm, d) relative to the residual 1 H resonance of the solvent CDCl$_3$ or CD$_3$OD at 7.26 ppm or 3.31 ppm, respectively. $^{13}$C NMR chemical shifts were reported relative to the central line of CDCl$_3$ or CD$_3$OD at 77.16 ppm or 49.00 ppm, respectively. Splitting patterns were designated as follows: s, singlet; br s, broad singlet; d, doublet; t, triplet; m, multiplet; quint, quintet. High resolution mass spectra were obtained at the Arizona State University CLAS High Resolution Mass Spectrometry Laboratory.

Example 1. Synthesis of 2-(Azetidin-1-yl)-4-cyclobutanoxy-6-methylpyrimidin-5-ol (1a)

Step 1. Synthesis of 2-(Azetidin-1-yl-4-cyclobutoxy-6-methylpyrimidine (5a)

To a stirred solution of 1.40 g (19.4 mmol) of cyclobutanol in 100 mL of freshly distilled THF under argon was slowly added 1.55 g (38.8 mmol) of NaH (60% in paraffin) and the reaction mixture was stirred at room temperature for 30 min. The cooled (0° C.) reaction mixture was treated dropwise with 3.00 g (18.5 mmol) of the 2,4-dichloro-6-methylpyrimidine in solution in 10 mL of distilled THF. The reaction mixture was allowed to warm to room temperature and was maintained under argon for 4 h. After the reaction was complete, as judged by silica gel TLC, the reaction mixture was poured slowly into 100 mL of deionized water. The aqueous layer was extracted with three 100-mL portions of ethyl acetate. The combined organic phase was dried over MgSO$_4$ and concentrated to dryness under diminished pressure. The crude product was recovered as a yellowish oil and was used directly for the next step. To 1.00 g (5 mmol) of the crude mixture was added 3.25 g (10.0 mmol) of Cs$_2$CO$_3$ and 936 mg (10.0 mmol) of azetidine hydrochloride in 30 mL of dry, degassed DMF. The suspension was stirred under argon at room temperature for 10 min and 118 mg (0.50 mmol) of 3,4,7,8-tetramethyl-1, 10-phenanthroline and 95.0 mg (0.50 mmol) of copper (I) iodide were added successively to the reaction mixture. The reaction mixture was then warmed to 50° C. and maintained under argon for 12 h. After the reaction was completed as judged by silica gel TLC, the reaction mixture was diluted in 30 mL of ethyl acetate and filtered through Celite. The filtrate was concentrated to dryness. The crude residue was purified by flash chromatography on a silica gel column (15×4 cm). Elution with 9:1 hexane/EtOAc afforded 5a as a colorless solid:yield 390 mg (35%); mp 60-61° C.; silica gel TLC R$_f$ 0.22 (4:1 hexane/EtOAc); $^1$H NMR (CDCl$_3$) δ 1.58-1.70 (m, 1H), 1.76-1.84 (m, 1H), 2.05-2.17 (m, 2H), 2.24 (s, 3H), 2.29 (qt, 2H, J=7.4

Hz), 2.38 (m, 2H), 4.08 (t, 4H, J=7.5 Hz), 5.04 (qt, 1H, J=7.4 Hz) and 5.77 (s, 1H); $^{13}$C NMR (CDCl$_3$) δ 13.6, 16.3, 24.2, 30.8, 50.2, 70.1, 95.0, 163.2, 168.2 and 169.6; mass spectrum (APCI), m/z 220.1445 (M+H)$^+$ (C$_{12}$H$_{18}$N$_3$O requires m/z 220.1450).

Step 2, Synthesis of 2-(Azetidin-1-yl)-5-bromo-4-cyclobutanoxy-6-methylpyrimidine (6)

To a stirred solution containing 112 mg (0.50 mmol) of 5a in 7 mL of freshly distilled CH$_2$Cl$_2$ at room temperature in the dark was added 178 mg (0.52 mmol) of recrystallized N-bromosuccinimide. The reaction mixture was stirred under argon for 1 hour at room temperature. The solvent was removed under diminished pressure and the resulting residue was purified by flash chromatography on a silica gel column (15×3 cm). Elution with 99:1 to 98:2 hexane/EtOAc afforded compound 6 as a colorless solid: yield 150 mg (98%); mp 84° C.; silica gel TLC R$_f$ 0.25 (9:1 hexane/EtOAc); $^3$H NMR (CDCl$_3$) δ 1.62 (m, 1H), 1.80 (m, 1H), 2.16 (m, 2H), 2.27 (qt, 2H, J=7.4 Hz), 2.36-2.40 (m, 5H), 4.03 (t, 4H, J=7.5 Hz) and 5.10 (qt, 1H, J=7.4 Hz); $^{13}$C NMR (CDCl$_3$) δ 13.6, 16.1, 24.4, 30.7, 50.2, 71.3, 92.8, 166.0, 164.5 and 160.8; mass spectrum (APCI), m/z 298.0552 (M+H)$^+$ (C$_{12}$H$_{17}$$^{79}$BrN$_3$O requires m/z 298.0555) and m/z 300.0529 (M+H)$^+$ (C$_{12}$H$_{17}$$^{81}$BrN$_3$O requires m/z 300.0535).

Step 3, Synthesis of 2-(Azetidin-1-yl)-4-cyclobutanoxy-6-methylpyrimidin-5-ol (1a)

A stirred solution containing 141 mg (0.49 mmol) of 6 in 5 mL of freshly distilled THF was cooled to −78° C. and maintained under argon for 10 min. To the resulting suspension was added 321 µL (0.51 mmol) of a 1.6 M solution of n-BuLi in hexane and the resulting reaction mixture was stirred at −78° C. for 1 h, resulting in a clear, yellowish solution. Then 110 µL (0.98 mmol) of trimethyl borate was added slowly and the reaction mixture was maintained at 0° C. for 1 additional hour. A solution of 300 µL of H$_2$O$_2$ (30% v/v) was then added and the reaction mixture was allowed to warm to room temperature and stirred for 30 min. The reaction mixture was diluted by the addition of 50 mL of satd aq NH$_4$Cl and extracted with two 30-mL portions of CH$_2$Cl$_2$. The combined organic phase was dried over MgSO$_4$ and concentrated under diminished pressure. The residue was purified by flash chromatography on a silica gel column (15×1 cm). Elution with 9:1 to 2:1 hexane/EtOAc afforded compound 1a as a colorless solid: yield 98 mg (90%); mp 198° C.; silica gel TLC R$_f$ 0.4 (2:1 hexane/EtOAc); $^1$H NMR (CDCl$_3$) δ 1.57 (m, 1H), 1.70 (m, 1H), 2.00 (m, 2H), 2.07 (s, 3H), 2.13 (qt, 2H, J=7.4 Hz), 2.29 (q, 2H, J=7.4 Hz), 3.80 (t, 4H, J=7.4 Hz), 4.98 (qt, 1H, J=7.4 Hz) and 7.82 (s, 1H); $^{13}$C NMR (DMSO-d6) δ 13.1, 15.6, 18.2, 30.4, 50.3, 69.7, 128.0, 153.0, 156.6 and 158.5; mass spectrum (APCI), m/z 236.1398 (M+H)$^+$ (C$_{12}$H$_{18}$N$_3$O$_2$ requires m/z 236.1399).

Example 2. Synthesis of 2-(Azetidin-1-yl)-4-cyclobutanoxy-6-tetradecylpyrimidin-5-ol (1b)

Step 1. Synthesis of 2-(Azetidin-1-yl)-4-cyclobutanoxy-6-tetradecylpyrimidine (7a)

A stirred solution containing 112 mg (0.50 mmol) of 5a in 3 mL of freshly distilled THF was cooled under argon at −78° C. and maintained under argon for 15 min. A solution containing 273 µL (0.54 mmol) of 1.6 M n-BuLi in hexane was added dropwise and the resulting reaction mixture was stirred at −78° C. for 1 h. A solution of 131 mg (0.50 mmol) of 1-bromotridecane in 200 µL of distilled THF was then added dropwise and the reaction mixture was allowed to warm to 0° C. and was stirred for 1 h. The reaction was quenched by the addition of 20 mL of satd aq NH$_4$Cl, and then extracted with two 15-mL portions of CH$_2$Cl$_2$. The combined organic phase was dried over MgSO$_4$ and concentrated under diminished pressure. The residue was purified by flash chromatography on a silica gel column (15×2 cm). Elution with 98:2 to 95:5 hexane/EtOAc to afford compound 7a as a colorless solid: yield 154 mg (76%); mp 43-44° C.; silica gel TLC R$_f$ 0.5 (9:1 hexane/EtOAc); $^1$H NMR (CDCl$_3$) δ 0.87 (t, 3H, J=6.6 Hz), 1.12-1.35 (m, 22H), 1.55-1.70 (m, 3H), 1.80 (m, 1H), 2.07-2.18 (m, 2H), 2.25-2.32 (m, 2H), 2.34-2.44 (m, 2H), 2.47 (t, 2H, J=7.6 Hz), 4.09 (t, 4H, J=7.5 Hz), 5.06 (qt, 1H, J=7.4 Hz) and 5.78 (s, 1H); $^{13}$C NMR (CDCl$_3$) δ 13.7, 14.2 16.3, 22.8, 28.8, 29.5, 29.5, 29.6, 29.7, 29.8, 29.82, 29.83, 30.85, 32.1, 38.0, 50.2, 70.1, 94.3, 163.4, 169.6 and 172.5; mass spectrum (APCI), m/z 402.3490 (M+H)$^+$ (C$_{25}$H$_{44}$N$_3$O requires m/z 402.3484).

Step 2, Synthesis of 2-(Azetidin-1-yl)-5-bromo-4-cyclobutanoxy-6-tetradecylpyrimidine (8a)

To a stirred solution containing 135 mg (0.36 mmol) of 7a in 5 mL of freshly distilled CH$_2$Cl$_2$ at room temperature in the dark was added 63 mg (0.38 mmol) of recrystallized N-bromosuccinimide. The reaction mixture was stirred under argon for 1 h at room temperature. The solvent was concentrated under diminished pressure and the resulting residue was purified by flash chromatography on a silica gel column (15×2 cm). Elution with 98:2 hexane/EtOAc afforded compound 8a as a colorless solid: yield 150 mg (93%); mp 71-72° C.; silica gel TLC R$_f$ 0.5 (9:1 hexane/AcOEt); $^1$H NMR (CDCl$_3$) δ 0.88 (t, 3H, J=6.6 Hz), 1.20-1.35 (m, 22H), 1.58-1.70 (m, 3H), 1.78-1.86 (m, 1H), 2.13-2.22 (m, 2H), 2.25-2.33 (m, 2H), 2.39-2.46 (m, 2H), 2.67-2.71 (m, 2H), 4.06 (t, 4H, J=7.5 Hz) and 5.13 (qt, 1H, J=7.4 Hz); $^{13}$C NMR (CDCl$_3$) δ 13.7, 14.2, 16.2, 22.8, 29.5, 29.6, 29.7, 29.8, 29.82, 29.83, 30.8, 32.1, 37.0, 50.3, 71.3, 92.7, 161.1, 164.7 and 169.5; mass spectrum (APCI), m/z 480.2561 (M+H)$^+$ (C$_{25}$H$_{43}$$^{79}$BrN$_3$O requires m/z 480.2589) and m/z 482.2560 (M+H)$^+$ (C$_{25}$H$_{43}$$^{81}$BrN$_3$O requires m/z 482.2569).

Step 3, Synthesis of 2-(Azetidin-1-yl)-4-cyclobutanoxy-6-tetradecylpyrimidin-5-ol (1b)

A stirred solution containing 150 mg (0.31 mmol) of 8b in 2 mL of freshly distilled THF was cooled to −78° C. and maintained under argon for 10 min. To the resulting suspension was added 234 µL (0.33 mmol) of 1.6 M n-BuLi in hexane and the resulting reaction mixture was stirred at −78° C. for 1 h, resulting in a clear, yellowish solution. Then 60 µL (0.62 mmol) of trimethyl borate was added slowly and the reaction was maintained at 0° C. for 1 additional hour. A solution of 400 µL of H$_2$O$_2$ (30% v/v) was then added and the reaction mixture was allowed to warm to room temperature and stirred for 30 min. The reaction mixture was diluted by addition of 50 mL of satd aq NH$_4$Cl and extracted with two 20-mL portions of CH$_2$Cl$_2$. The combined organic phase was dried over MgSO$_4$ and concentrated under diminished pressure. The residue was purified by flash chromatography on a silica gel column (15×1 cm). Elution with 98:2 to 9:1 hexane/EtOAc afforded compound 1b as a colorless solid: yield 112 mg (86%); mp 100° C.; silica gel TLC R$_f$ 0.2 (9:1 hexane/EtOAc); $^1$H NMR (CDCl$_3$) δ 0.88 (t, 3H, J=6.6 Hz), 1.20-1.35 (m, 22H), 1.55-1.70 (m, 3H), 1.83 (m, 1H), 2.06-2.16 (m, 2H), 2.26 (qt, 2H, J=7.2 Hz), 2.37-2.45 (m, 2H), 2.61 (m, 2H), 4.01 (t, 4H, J=7.2 Hz), 4.76 (br s, 1H) and 5.17 (qt, 1H, J=7.4 Hz); $^{13}$C NMR (CDCl$_3$) δ 13.6, 14.3, 16.3, 22.8, 28.2, 29.5, 29.71, 29.73, 29.8, 29.81, 29.86, 29.9, 30.9, 31.5, 32.1, 50.9, 70.8, 128.1, 155.2, 157.6, 157.8; mass spectrum (APCI), m/z 418.3417 (M+H)$^+$ (C$_{25}$H$_{44}$N$_3$O$_2$ requires m/z 418.3434).

Example 3. Synthesis of 2-(Azetidin-1-yl)-4-cyclobutoxy-6-hexadecylpyrimidin-5-ol (1c)

Step 1. Synthesis of 2-(Azetidin-1-yl-4-cyclobutoxy-6-hexadecylpyrimidine (7b)

A stirred solution containing 242 mg (1.07 mmol) of 5a in 10 mL of freshly distilled THF was cooled under argon at −78° C. and maintained under argon for 15 min. A solution of 739 μL (1.18 mmol) of 1.6 M n-BuLi in hexane was added dropwise and the resulting reaction mixture was stirred at −78° C. for 1 h. A solution of 319 mg (1.07 mmol) of 1-bromopentadecane in 500 μL of distilled THF was then added dropwise and the reaction mixture was allowed to warm to 0° C. and was stirred for 1 h. The reaction was quenched by the addition of 30 mL of satd aq NH$_4$Cl, and extracted with two 25-mL portions of CH$_2$Cl$_2$. The combined organic phase was dried over MgSO$_4$ and concentrated under diminished pressure. The residue was purified by flash chromatography on a silica gel column (15×2 cm). Elution with 98:2 to 95:5 hexane/EtOAc afforded compound 7b as a colorless solid: yield 389 mg (84%); mp 39-40° C.; silica gel TLC R$_f$ 0.5 (9:1 hexane/EtOAc); $^3$H NMR (CDCl$_3$) δ 0.87 (t, 3H, J=6.6 Hz), 1.20-1.35 (m, 26H), 1.58-1.70 (m, 3H), 1.76-1.85 (m, 1H), 2.07-2.18 (m, 2H), 2.25-2.32 (m, 2H), 2.35-2.45 (m, 2H), 2.70 (t, 2H, J=7.6 Hz), 4.08 (t, 4H, J=7.5 Hz), 5.06 (qt, 1H, J=7.4 Hz) and 5.78 (s, 1H); $^{13}$C NMR (CDCl$_3$) δ 13.7, 14.2 16.3, 22.8, 28.8, 29.5, 29.5, 29.6, 29.7, 29.8, 29.8, 29.8, 30.8, 32.1, 38.0, 50.2, 70.1, 94.3, 163.4, 169.6 and 172.5; mass spectrum (FAB), m/z 430.3786 (M+H)$^+$ (C$_{25}$H$_{48}$N$_3$O requires m/z 430.3797).

Step 2, Synthesis of 2-(Azetidin-1-yl-5-bromo-4-cyclobutoxy-6-hexadecylpyrimidine (8b)

To a stirred solution containing 340 mg (0.79 mmol) of 7b in 8 mL of freshly distilled CH$_2$Cl$_2$ at room temperature in the dark was added 147 mg (0.83 mmol) of recrystallized N-bromosuccinimide. The reaction mixture was stirred under argon for 1 h at room temperature. The solvent was removed under diminished pressure and the residue was purified by flash chromatography on a silica gel column (15×2 cm). Elution with 99:1 to 98:2 hexane/EtOAc afforded compound 8b as a colorless solid:yield 389 mg (96%); mp 84° C. silica gel TLC R$_f$ 0.25 (9:1 hexane/EtOAc); mp 71-73° C. silica gel TLC R$_f$ 0.5 (95:5 hexane/EtOAc); $^1$H NMR (CDCl$_3$) 0.88 (t, 3H, J=6.6 Hz), 1.2-1.35 (m, 26H), 1.58-1.70 (m, 3H), 1.78-1.86 (m, 1H), 2.13-2.22 (m, 2H), 2.25-2.33 (m, 2H), 2.39-2.46 (m, 2H), 2.67-2.71 (m, 2H), 4.06 (t, 4H, J=7.5 Hz) and 5.13 (qt, 1H, J=7.4 Hz); $^{13}$C NMR (CDCl$_3$) δ 13.7, 14.2, 16.2, 22.8, 28.0, 29.5, 29.6, 29.7, 29.8, 29.8, 29.81, 29.9, 30.8, 32.1, 37.0, 50.3, 71.3, 92.7, 161.1, 164.7 and 169.5; mass spectrum (FAB), m/z 508.2897 (M+H)$^+$ (C$_{25}$H$_{47}$BrN$_3$O requires m/z508.2902).

Step 3, Synthesis of 2-(Azetidin-1-yl)-4-cyclobutoxy-6-hexadecylpyrimidin-5-ol (1c)

A stirred solution containing 340 mg (0.67 mmol) of 5a in 7 mL of freshly distilled THF was cooled to −78° C. and maintained under argon for 10 min. To the resulting suspension was added 458 μL (0.73 mmol) of 1.6 M n-BuLi in hexane and the reaction mixture was stirred at −78° C. for 1 h resulting in a clear, yellowish solution. Then 120 μL (1.34 mmol) of trimethyl borate was added slowly and the reaction was maintained at 0° C. for 1 additional hour. A solution of 300 μL of H$_2$O$_2$ (30% v/v) was then added and the reaction mixture was allowed to warm to room temperature and stirred for 30 min. The reaction mixture was diluted by the addition of 50 mL of satd aq NH$_4$Cl and extracted with two 30-mL portions of CH$_2$Cl$_2$. The combined organic phase was dried over MgSO$_4$ and concentrated under diminished pressure. The residue was purified by flash chromatography on a silica gel column (15×1 cm). Elution with 98:2 to 9:1 hexane/EtOAc to afford compound 1c as a colorless solid: yield 248 mg (84%); mp 95-97° C.; silica gel TLC R$_f$ 0.42 (4:1 hexane/EtOAc); $^3$H NMR (CDCl$_3$) δ 0.88 (t, 3H, J=6.6 Hz), 1.2-1.35 (m, 26H), 1.55-1.70 (m, 3H), 1.83 (m, 1H), 2.06-2.16 (m, 2H), 2.26 (quint, 2H, J=7.2 Hz), 2.37-2.45 (m, 2H), 2.61 (m, 2H), 4.01 (t, 4H, J=7.2 Hz), 4.76 (br s, 1H) and 5.17 (qt, 1H, J=7.4 Hz); $^{13}$C NMR (CDCl$_3$) δ 13.6, 14.3, 16.3, 22.8, 28.2, 29.5, 29.71, 29.73, 29.8, 29.81, 29.86, 29.9, 30.9, 31.5, 32.1, 50.9, 70.8, 128.1, 155.2, 157.6 and 157.8; mass spectrum (FAB), m/z 446.3742 (M+H)$^+$ (C$_{25}$H$_{48}$N$_3$O$_2$ requires m/z446.3747).

Example 4. Synthesis of 4-(Azetidin-1-yl)-2-cyclobutanoxy-6-methylpyrimidin-5-ol (2a)

Step 1. Synthesis of 4-(Azetidin-1-yl)-2-cyclobutanoxy-6-methylpyrimidine (5b)

This compound was isolated as a side product from the reaction employed for the preparation of compound 5a after purification by flash chromatography on a silica gel column (15×4 cm). Elution with 2:1 hexane/EtOAc afforded 5b as a yellowish oil, yield 385 mg (34%); silica gel TLC R$_f$ 25 (2:1 hexane/EtOAc); $^1$H NMR (CDCl$_3$) δ 1.54-1.66 (m, 1H), 1.73-1.82 (m, 1H), 2.12-2.22 (m, 2H), 2.24 (s, 3H), 2.34-2.42 (m, 4H), 4.05 (t, 4H, J=7.4 Hz), 5.12 (qt, 1H, J=7.4 Hz) and 5.64 (s, 1H); $^{13}$C NMR (CDCl$_3$) δ 13.6, 16.7, 23.9, 30.8, 49.9, 70.4, 94.3, 164.2, 165.0 and 166.2; mass spectrum (APCI), m/z 220.1453 (M+H)$^+$ (C$_{12}$H$_{18}$N$_3$O requires m/z 220.1450).

Step 2, Synthesis of 4-(Azetidin-1-yl-5-bromo-2-cyclobutanoxy-6-methylpyrimidine (11)

To a stirred solution containing 280 mg (1.28 mmol) of 5b in 12 mL of freshly distilled CH$_2$Cl$_2$ at room temperature in the dark was added 236 mg (1.3 mmol) of recrystallized N-bromosuccinimide. The reaction mixture was stirred under argon for 1 h. The solvent was removed under diminished pressure and the resulting residue was purified by flash chromatography on a silica gel column (15×2 cm). Elution with 95:5 to 9:1 hexane/EtOAc to afford compound 11 as a colorless solid: yield 360 mg (95%); mp 55° C. silica gel TLC R$_f$ 0.2 (9:1 hexane/EtOAc); $^1$H NMR (CDCl$_3$) δ 1.48-1.60 (m, 1H), 1.68-1.78 (m, 1H), 2.05-2.14 (m, 2H), 2.22 (qt, 2H, J=7.8 Hz), 2.27-2.37 (m, 2H), 2.31 (s, 3H), 4.30 (t, 4H, J=7.4 Hz) and 4.97 (qt, 1H, J=7.4 Hz); $^{13}$C NMR (CDCl$_3$)δ 13.4, 16.1, 24.5, 30.6, 52.9, 70.7, 93.6, 160.6, 162.1 and 165.9; mass spectrum (APCI), m/z 298.0547 (M+H)$^+$ (C$_{12}$H$_{17}^{79}$BrN$_3$O requires m/z 298.0555), m/z 300.0525 (M+H)$^+$ (C$_{12}$H$_{17}^{81}$BrN$_3$O requires m/z 300.0535).

Step 3, Synthesis of 4-(Azetidin-1-yl-2-cyclobutan-oxy-6-methylpyrimidin-5-ol (2a)

A stirred solution containing 150 mg (0.51 mmol) of 11 in 7 mL of freshly distilled THF was cooled to −78° C. and maintained under argon for 10 min. To the resulting suspension was added 330 µL of 1.6 M BuLi in hexane (0.53 mmol) and the resulting reaction mixture was stirred at −78° C. for 1 h, resulting in a clear yellowish solution. A solution containing 117 µL (1.06 mmol) of trimethyl borate was added slowly and the reaction was maintained at 0° C. for 1 additional hour. A solution of 400 µL of $H_2O_2$ (30% v/v) was then added and the reaction mixture was allowed to warm to room temperature and was then stirred for 30 min. The reaction mixture was diluted by addition of 50 mL of satd aq $NH_4Cl$ and extracted with two 30-mL portions of $CH_2Cl_2$. The combined organic phase was combined, dried over $MgSO_4$ and concentrated under diminished pressure. The residue was purified by flash chromatography on a silica gel column (15×1 cm). Elution with 9:1 to 1:1 hexane/EtOAc to afford compound 2a as a colorless solid: yield 88 mg (73%); mp 59° C.; silica gel TLC $R_f$ 0.15 (1:1 hexane/EtOAc); $^1$H NMR (DMSO-$d_6$) δ 1.56 (m, 1H, 7=8.7 Hz), 1.70 (q, 1H, 7=9.8 Hz), 1.94 (qt, 2H, J=10.6 Hz), 2.09 (s, 3H), 2.18-2.35 (m, 4H), 4.11 (t, 4H, J=7.4 Hz), 4.90 (qt, 1H, J=7.3 Hz) and 7.74 (s, 1H); $^{13}$C NMR (CDCl$_3$) δ 13.0, 26.6, 18.2, 30.3, 51.7, 69.1, 130.4, 151.5, 156.8 and 157.3; mass spectrum (APCI), m/z 236.1403 (M+H)$^+$ ($C_{12}H_{18}N_3O_2$ requires m/z 236.1399).

Example 5. Synthesis of 4-(Azetidin-1-yl)-2-cyclobutanoxy-6-tetradecylpyrimidin-5-ol (2b)

Step 1. Synthesis of 4-(Azetidin-1-yl-2-cyclobutan-oxy-6-tetradecylpyrimidine (9a)

A stirred solution containing 342 mg (1.56 mmol) of 5b in 10 mL of freshly distilled THF was cooled under argon at −78° C. and maintained under argon for 15 min. A solution containing 1.00 mL (1.60 mmol) of 1.6 M n-BuLi in hexane was added dropwise and the resulting reaction mixture was stirred at −78° C. for 1 h. A solution of 420 mg (1.60 mmol) of 1-bromotridecane in solution in 1 mL of distilled THF was then added dropwise and the reaction mixture was allowed to warm to 0° C. and stirred for 1 h. The reaction was quenched by adding 40 mL of satd aq $NH_4Cl$ and then extracted with two 35-mL portions of $CH_2Cl_2$. The combined organic phase was dried over $MgSO_4$ and concentrated under diminished pressure. The residue was purified by flash chromatography on a silica gel column (15×2 cm). Elution with 98:2 to 95:5 hexane/EtOAc afforded compound 9a as a colorless solid: yield 583 mg (95%); mp 182° C.; silica gel TLC $R_f$ 0.15 (9:1 hexane/EtOAc); $^3$H NMR (CDCl$_3$) δ 0.86 (t, 3H, J=6.6 Hz), 1.2-1.35 (m, 22H), 1.53-1.68 (m, 3H), 1.73-1.81 (m, 1H), 2.12-2.22 (m, 2H), 2.33-2.46 (m, 4H), 2.45 (m, 2H), 4.04 (t, 4H, 7=7.5 Hz), 5.11 (qt, 1H, 7=7.4 Hz) and 5.61 (s, 1H); $^{13}$C NMR (CDCl$_3$) δ 13.6, 14.2, 16.7, 22.8, 28.6, 29.5, 29.6, 29.7, 29.77, 29.79, 29.8, 29.82, 30.8, 32.0, 37.9, 49.9, 70.3, 93.8, 164.5, 165.1 and 170.7; mass spectrum (APCI), m/z 402.3496 (M+H)$^+$ ($C_{25}H_{44}N_3O$ requires m/z 402.3484).

Step 2, Synthesis of 4-(Azetidin-1-yl)-5-bromo-2-cyclobutanoxy-6-tetradecylpyrimidine (10a)

To a stirred solution containing 536 mg (1.12 mmol) of 9a in 20 mL of freshly distilled $CH_2Cl_2$ at room temperature in the dark was added 204 mg (1.15 mmol) of recrystallized N-bromosuccinimide. The reaction mixture was stirred under argon for 1 h at room temperature. The solvent was concentrated under diminished pressure and the resulting residue was purified by flash chromatography on a silica gel column (15×2 cm). Elution with 98:2 hexane/EtOAc to afford compound 10a as a colorless solid: yield 582 mg (91%); mp 52° C.; silica gel TLC $R_f$ 0.5 (9:1 hexane/EtOAc); $^1$H NMR (CDCl$_3$) δ 0.87 (t, 3H, J=6.6 Hz), 1.18-1.38 (m, 22H), 1.55-1.68 (m, 3H), 1.73-1.82 (m, 1H), 2.12-2.22 (m, 2H), 2.22-2.30 (m, 2H), 2.33-2.42 (m, 2H), 2.66 (m, 2H), 4.37 (t, 4H, J=7.5 Hz) and 5.03 (qt, 1H, J=7.4 Hz); $^{13}$C NMR (CDCl$_3$) δ 13.6, 14.3, 16.3, 22.8, 27.8, 29.5, 29.58 29.61, 29.7, 29.80, 29.82, 29.84, 30.7, 32.1, 37.9, 53.1, 71.0, 93.8, 161.1, 162.4 and 169.4; mass spectrum (APCI), m/z 480.2580 (M+H)$^+$ ($C_{25}H_{43}^{79}BrN_3O$ requires m/z 480.2589), m/z 482.2570 (M+H)$^+$ ($C_{25}H_{43}^{81}BrN_3O$ requires m/z 482.2569).

Step 3, Synthesis of 4-(Azetidin-1-yl-2-cyclobutan-oxy-6-tetradecylpyrimidin-5-ol (2b)

A stirred solution containing 200 mg (0.41 mmol) of 10a in 4 mL of freshly distilled THF was cooled to −78° C. and maintained under argon for 10 min. To the resulting suspension was added 274 µL of 1.6 M n-BuLi in hexane (0.44 mmol) and the resulting reaction mixture was stirred at −78° C. for 1 h, resulting in a clear yellowish solution. A sample of 50 µL (0.82 mmol) of trimethyl borate was added slowly and the reaction was maintained at 0° C. for 1 additional hour. A solution of 500 µL of $H_2O_2$ (30% v/v) was then added and the reaction mixture was allowed to warm to room temperature and stirred for 30 min. The reaction mixture was diluted by the addition of 50 mL of satd aq $NH_4Cl$ and was then extracted with two 30-mL portions of $CH_2Cl_2$. The combined organic phase was dried over $MgSO_4$ and concentrated under diminished pressure. The residue was purified by flash chromatography on a silica gel column (15×1 cm). Elution with 98:2 to 9:1 hexane/EtOAc afforded compound 2b as a colorless solid: yield 116 mg (68%); mp 84° C.; silica gel TLC $R_f$ 0.45 (2:1 hexane/EtOAc); $^1$H NMR (CDCl$_3$) δ 0.88 (t, 3H, J=6.6 Hz), 1.20-1.36 (m, 22H), 1.54-1.68 (m, 3H), 1.71-1.81 (m, 1H), 2.09-2.20 (m, 2H), 2.26-2.40 (m, 4H), 2.49 (m, 2H), 4.26 (t, 4H, J=7.5 Hz) and 5.02 (qt, 1H, J=7.5 Hz); $^{13}$C NMR (CDCl$_3$) δ 13.6, 14.3, 17.4, 22.8, 27.9, 29.52, 29.70, 29.74, 29.83, 31.1, 32.1, 52.3, 70.5, 130.1, 154.8, 156.8 and 158.4; HRMS (APCI), m/z 418.3443 (M+H)$^+$ ($C_{25}H_{44}N_3O_2$ requires m/z 418.3434).

Example 6. Synthesis of 4-(Azetidin-1-yl)-2-cyclobutanoxy-6-hexadecylpyrimidin-5-ol (2c)

Step 1. Synthesis of 4-(Azetidin-1-yl-2-cyclobutan-oxy-6-hexadecylpyrimidine (9b)

A stirred solution containing 215 mg (0.96 mmol) of 5b in 10 mL of freshly distilled THF was cooled under argon at −78° C. and maintained under argon for 15 min. A solution containing 631 µL (1.01 mmol) of 1.6 M n-BuLi in hexane was added dropwise and the resulting reaction mixture was stirred at −78° C. for 1 h. A solution of 278 mg (0.96 mmol) of 1-bromopentadecane in 500 µL of distilled THF was then added dropwise and the reaction was then allowed to warm to 0° C. and stirred for 1 h. The reaction was quenched by the addition of 40 mL of satd aq $NH_4Cl$ and extracted with two 35-mL portions of $CH_2Cl_2$. The combined organic phase was dried over MgSO$_4$ and concentrated under diminished pressure. The residue was purified by flash chromatography on a silica gel column (15×2 cm). Elution with 9:1 to 1:1 hexane/EtOAc afforded compound 9b as a colorless solid: yield 362 mg (88%); mp 179° C.; silica gel TLC R$_f$ 0.15 (9:1 hexane/EtOAc); $^1$H NMR (CDCl$_3$) δ 0.85 (t, 3H, J=6.6 Hz), 1.18-1.34 (m, 26H), 1.53-1.65 (m, 3H), 1.75 (qt, 1H, J=9.9 Hz), 2.16 (qt, 2H, J=9.9 Hz), 2.30-2.39 (m, 4H), 2.43 (t, 2H, J=8.1 Hz), 4.02 (t, 4H, J=7.5 Hz), 5.09 (qt, 1H, J=7.4 Hz) and 5.60 (s, 1H); $^{13}$C NMR (CDCl$_3$) δ 13.6, 14.2, 16.7, 22.8, 28.6, 29.4, 29.6, 29.7, 29.75, 29.8, 30.8, 32.0, 37.9, 49.8, 70.3, 93.7, 164.5, 165.1 and 170.7; HRMS (APCI), m/z 430.3795 (M+H)$^+$ (C$_{27}$H$_{48}$N$_3$O requires m/z 430.3797).

Step 2, Synthesis of 4-(Azetidin-1-yl-5-bromo-2-cyclobutanoxy-6-hexadecylpyrimidine (10b)

To a stirred solution containing 208 mg (0.48 mmol) of 9b dissolved in 5 mL of freshly distilled CH$_2$Cl$_2$ at room temperature in the dark was added 90.0 mg (0.50 mmol) of recrystallized A-bromosuccinimide. The reaction mixture was stirred under argon for 1 h at room temperature. The solvent was concentrated under diminished pressure and the resulting residue was purified by flash chromatography on a silica gel column (15×2 cm). Elution with 98:2 to 95:5 hexane/EtOAc afforded compound 10b as a colorless solid: yield 231 mg (91%); mp 56° C.; silica gel TLC R$_f$ 0.5 (9:1 hexane/EtOAc); $^1$H NMR (CDCl$_3$) δ 0.87 (t, 3H, J=6.6 Hz), 1.12-1.35 (m, 26H), 1.55-1.68 (m, 3H), 1.77-1.81 (m, 1H), 2.06-2.28 (m, 4H), 2.28-2.38 (m, 2H), 2.66 (t, 2H, J=7.5 Hz), 4.37 (t, 4H, J=7.5 Hz) and 5.03 (qt, 1H, J=7.4 Hz); $^{13}$C NMR (CDCl$_3$) δ 13.5, 14.2, 16.2, 22.8, 27.7, 29.4, 29.5, 29.55, 29.6, 29.7, 29.8, 30.7, 32.0, 53.0, 70.9, 93.7, 161.0, 162.3 and 169.3; mass spectrum (APCI), m/z 508.2904 (M+H)$^+$ (C$_{27}$H$_{47}$$^{79}$BrN$_3$O requires m/z 508.2902), m/z 510.3906 (M+H)$^+$ (C$_{27}$H$_{47}$$^{81}$BrN$_3$O requires m/z 510.3916).

Step 3. Synthesis of 4-(Azetidin-1-yl-2-cyclobutanoxy-6-hexadecylpyrimidin-5-ol (2c)

A stirred solution containing 200 mg (0.39 mmol) of 10b in 4 mL of freshly distilled THF was cooled to −78° C. and maintained under argon for 10 min. To the resulting suspension was added 259 μL of 1.6 M n-BuLi in hexane (0.41 mmol) and the resulting reaction mixture was stirred at −78° C. for 1 h, resulting in a clear yellowish solution. A sample of 86 μL (0.78 mmol) of trimethyl borate was added slowly and the reaction mixture was maintained at 0° C. for 1 additional hour. A solution of 500 μL of H$_2$O$_2$ (30% v/v) was then added and the reaction was allowed to warm to room temperature and stirred for 30 min. The reaction mixture was diluted by the addition of 50 mL of satd NH$_4$Cl and extracted with two 30-mL portions of CH$_2$Cl$_2$. The combined organic phase was dried over MgSO$_4$ and concentrated under diminished pressure. The residue was purified by flash chromatography on a silica gel column (15×1 cm). Elution with 9:1 to 8:2 hexane/EtOAc afforded compound 2c as a colorless solid: yield 122 mg (70%); mp 85° C.; silica gel TLC R$_f$ 0.5 (2:1 hexane/EtOAc); $^1$H NMR (CDCl$_3$) δ 0.86 (t, 3H, J=6.6 Hz), 1.18-1.35 (m, 26H), 1.49-1.60 (m, 3H), 1.68-1.75 (m, 1H), 2.09-2.20 (m, 2H), 2.20-2.35 (m, 4H), 2.43 (t, 2H, J=7.5 Hz), 4.24 (t, 4H, J=7.4 Hz), 4.95 (qt, 1H, J=7.4 Hz) and 6.36 (br s, 1H); $^{13}$C NMR (CDCl$_3$) δ 13.5, 14.2, 17.3, 21.1, 22.8, 28.2, 29.79, 29.84, 29.86, 29.88, 30.7, 31.0, 32.0, 52.1, 70.3, 130.1, 156.0, 157.5 and 158.0; mass spectrum (APCI), m/z 446.3739 (M+H)$^+$ (C$_{27}$H$_{48}$N$_3$O$_2$ requires m/z 446.3747).

Example 7. Synthesis of 2,4-Dicyclobutanoxy-6-methylpyrimidin-5-ol (3a)

Step 1. Synthesis of 2,4-Dicyclobutanoxy-6-methylpyrimidine (12)

To a solution containing 1.66 g (23.0 mmol) of cyclobutanol in 60 mL of freshly distilled THF under argon was added slowly 1.84 g (46.0 mmol) of NaH (60% in paraffin) and the reaction mixture was stirred at room temperature for 20 min. The resulting suspension was cooled to 0° C. and 1.50 g (9.20 mmol) of 2,4-dichloro-6-methylpyrimidine was added in portions; the resulting yellow reaction mixture was stirred at room temperature overnight. After the reaction was completed, as judged by silica gel TLC analysis, the reaction mixture was poured slowly into 100 mL of water. The aqueous layer was extracted with two 50-mL portions of CH$_2$Cl$_2$. The combined organic phase washed with 50 mL of brine and dried over MgSO$_4$. The resulting solution was concentrated under diminished pressure. The crude mixture was purified by flash chromatography on a silica gel column (15×4 cm). Elution with 95:5 to 9:1 hexane/EtOAc afforded compound 12 as a colorless oil: yield 1.95 mg (91%); silica gel TLC IF 0.2 (95:5 hexane/EtOAc); $^1$H NMR (CDCl$_3$) δ 1.55-1.67 (m, 2H), 1.72-1.83 (m, 2H), 2.04-2.20 (m, 4H), 2.27 (s, 3H), 2.32-2.44 (m, 4H), 5.09 (qt, 1H, J=7.5 Hz), 5.15 (qt, 1H, J=7.5 Hz) and 6.08 (s, 1H); $^{13}$C NMR (CDCl$_3$) δ 13.49, 13.51, 23.9, 30.57, 30.63, 70.3, 70.9, 99.9, 164.1, 169.4 and 170.7; mass spectrum (APCI), m/z 235.1441 (M+H)$^+$ (C$_{11}$H$_{19}$N$_2$O$_2$ requires m/z 235.1447).

Step 2, Synthesis of 2,4-Dicyclobutoxy-5-bromo-6-methylpyrimidine (13)

To a stirred solution containing 280 mg (1.20 mmol) of 12 in 6 mL of freshly distilled CH$_2$Cl$_2$ at room temperature in the dark was added 425 mg (2.40 mmol) of recrystallized N-bromosuccinimide. The reaction mixture was stirred under argon for 72 h. The solvent was concentrated under diminished pressure and the resulting residue was purified by flash chromatography on a silica gel column (15×3 cm). Elution with 98:2 to 95:5 hexane/EtOAc afforded compound 13 as a colorless oil: yield 360 mg (96%); silica gel TLC R$_f$ 0.5 (9:1 hexane/EtOAc); $^1$H NMR (CDCl$_3$) δ 1.59-1.70 (m, 2H), 1.76-1.88 (m, 2H), 2.11-2.25 (m, 4H), 2.34-2.5 (m, 7H), 5.05 (qt, 1H, J=7.4 Hz) and 5.20 (qt, 1H, J=7.4 Hz); $^{13}$C NMR (CDCl$_3$) δ 13.49, 13.51, 24.4, 30.5, 30.6, 71.4, 71.8, 97.8, 162.1, 165.9 and 167.7; mass spectrum (APCI), m/z 313.0548 (M+H)$^+$ (C$_{13}$H$_{18}$$^{79}$BrN$_2$O$_2$ requires m/z 313.0552). m/z 315.0532 (M+H)$^+$ (C$_{13}$H$_{18}$$^{81}$BrN$_2$O$_2$ requires m/z 315.0531).

Step 3, Synthesis of 2,4-Dicyclobutanoxy-6-methylpyrimidin-5-ol (3a)

A stirred solution containing 200 mg (0.64 mmol) of 13 in 8 mL of freshly distilled THF was cooled to −78° C. and maintained under argon for 10 min. To the resulting suspension was added 400 μL (0.64 mmol) of 1.6 M n-BuLi in hexane and the resulting reaction mixture was stirred at −78° C. for 1 h leading to a clear yellowish solution. Then 141 μL (1.27 mmol) of trimethyl borate was added slowly and the reaction mixture was maintained at 0° C. for an additional hour. A solution of 500 μL of H$_2$O$_2$ (30% v/v) was then added and the reaction mixture was allowed to warm to room temperature and stirred for 30 min. The reaction mixture was diluted by the addition of 50 mL of satd aq NH$_4$Cl and extracted with two 30-mL portions of CH$_2$Cl$_2$. The combined organic phase was dried over MgSO$_4$ and concentrated under diminished pressure. The residue was purified by flash chromatography on a silica gel column (15×1 cm). Elution with 95:5 to 9:1 hexane/EtOAc afforded compound 3a as a colorless solid: yield 105 mg (67%); mp 122° C.; silica gel TLC R$_f$ 0.15 (9:1 hexane/EtOAc); $^3$H NMR (CDCl$_3$) δ 1.55-1.68 (m, 2H), 1.70-1.85 (m, 2H), 2.05-2.17 (m, 4H), 2.31 (s, 3H), 2.32-2.48 (m, 4H), 5.00 (qt, 1H, J=7.4 Hz), 5.21 (qt, 1H, J=7.4 Hz) and 5.38 (br s, 1H); $^{13}$C NMR (CDCl$_3$) δ 13.49, 13.51, 24.4, 30.5, 30.6, 71.4, 71.8, 97.8, 162.1, 165.9 and 167.7; mass spectrum (APCI), m/z 251.1390 (M+H)$^+$ (C$_{13}$H$_{19}$N$_2$O$_3$ requires m/z 251.1396).

Example 8. Synthesis of
2,4-Dicyclobutanoxy-6-tetradecylpyrimidin-5-ol
(3b)

Step 1. Synthesis of
2,4-Dicyclobutanoxy-6-tetradecylpyrimidine (14a)

A stirred solution containing 270 mg (1.15 mmol) of 12 in 5 mL of freshly distilled THF was cooled to −78° C. and maintained under argon. After 15 min, 790 μL (1.60 mmol) of 1.6 M n-BuLi in hexane was added dropwise and the resulting reaction mixture was stirred at −78° C. for 1 h. A solution containing 304 mg (1.15 mmol) of 1-bromotridecane in 1 mL of distilled THF was then added dropwise and the reaction mixture was allowed to warm to 0° C. and then stirred for 1 h. The reaction was quenched by the addition of 40 mL of satd aq NH$_4$Cl and extracted with two 35-mL portions of CH$_2$Cl$_2$. The combined organic phase was dried over MgSO$_4$ and concentrated under diminished pressure. The residue was purified by flash chromatography on a silica gel column (15×2 cm). Elution with 98:2 to 95:5 hexane/EtOAc afforded compound 14a as a colorless oil: yield 440 mg (92%); silica gel TLC R$_f$ 0.4 (95:5 hexane/EtOAc); $^1$H NMR (CDCl$_3$) δ 0.86 (t, 3H, 6.5 Hz), 1.16-1.34 (m, 22H), 1.60-1.68 (m, 4H), 1.75-1.85 (m, 2H), 2.07-2.16 (m, 2H), 2.17-2.23 (m, 2H), 2.35-2.45 (m, 4H), 2.52 (m, 2H), 5.11 (qt, 1H, J=7.4 Hz), 5.18 (qt, 1H, 7.5 Hz) and 6.10 (s, 1H); $^{13}$C NMR (CDCl$_3$) δ 13.6, 14.2, 22.8, 27.5, 28.6, 29.4, 29.48, 29.55, 29.6, 29.8, 30.6, 30.7, 32.0, 34.8, 37.7, 70.3, 70.4, 70.9, 71.0, 99.4, 99.5, 164.3, 170.7 and 173.6; mass spectrum (APCI), m/z 417.3475 (M+H)$^+$ (C$_{26}$H$_{45}$N$_2$O$_2$ requires m/z 417.3481).

Step 2, Synthesis of
5-Bromo-2,4-dicyclobutoxy-6-tetradecylpyrimidine
(15a)

To a stirred solution containing 300 mg (0.72 mmol) of 14a in 5 mL of freshly distilled CH$_2$Cl$_2$ at room temperature in the dark was added 256 mg (1.44 mmol) of recrystallized N-bromosuccinimide. The reaction mixture was stirred under argon for 72 h. The solvent was concentrated under diminished pressure and the resulting residue was purified by flash chromatography on a silica gel column (15×3 cm). Elution with 98:2 hexane/EtOAc afforded compound 15a as a colorless oil: yield 311 mg (87%); silica gel TLC R$_f$ 0.45 (95:5 hexane/EtOAc); $^1$H NMR (CDCl$_3$) δ 0.88 (t, 3H, J=6.5 Hz), 1.20-1.40 (m, 22H), 1.61-1.700 (m, 4H), 1.79-1.90 (m, 2H), 2.15-2.27 (m, 4H), 2.37-2.51 (m, 4H), 2.76 (m, 2H), 5.08 (qt, 1H, J=7.5 Hz) and 5.23 (qt, 1H, J=7.6 Hz); $^{13}$C NMR (CDCl$_3$) δ 13.6, 14.3, 22.8, 27.8, 29.5, 29.55, 29.7, 29.81, 29.82, 29.84, 30.6, 30.7, 32.1, 37.0, 71.5, 71.9, 97.7, 162.4, 166.1 and 171.1; mass spectrum (APCI), m/z 495.2591 (M+H)$^+$ (C$_{26}$H$_{44}$$^{79}$BrN$_2$O$_2$ requires m/z 495.2586) and m/z 497.2575 (M+H)$^+$ (C$_{26}$H$_{44}$$^{81}$BrN$_2$O$_2$ requires m/z 497.2566).

Step 3, Synthesis of
2,4-Dicyclobutanoxy-6-tetradecylpyrimidin-5-ol
(3b)

A stirred solution containing 180 mg (0.36 mmol) of 15a in 5 mL of freshly distilled THF was cooled to −78° C. and maintained under argon for 10 min. To the resulting suspension was added slowly 225 μL (0.36 mmol) of 1.6 M n-BuLi in hexane and the resulting reaction mixture was stirred at −78° C. for 1 h leading to a clear yellowish solution. Then 80.0 μL (0.73 mmol) of trimethyl borate was added slowly and the reaction mixture was maintained at 0° C. for an additional hour. A solution of 200 μL of H$_2$O$_2$ (30% v/v) was then added and the reaction mixture was allowed to warm to room temperature and was stirred for 30 min. The reaction mixture was diluted by the addition of 20 mL of satd aq NH$_4$Cl and extracted with two 15-mL portions of CH$_2$Cl$_2$. The combined organic phase was dried over MgSO$_4$ and concentrated under diminished pressure. The residue was purified by flash chromatography on a silica gel column (15×1 cm). Elution with 98:2 to 9:1 hexane/EtOAc afforded compound 3b as a colorless solid: yield 72 mg (46%); mp 60° C.; silica gel TLC R$_f$ 0.40 (9:1 hexane/EtOAc); $^3$H NMR (CDCl$_3$) δ 0.87 (t, 3H, 6.5 Hz), 1.15-1.38 (m, 22H), 1.58-1.72 (m, 4H), 1.76-1.88 (m, 2H), 2.08-2.22 (m, 4H), 2.35-2.51 (m, 4H), 2.64 (m, 2H), 4.80 (s, 1H), 5.02 (qt, 1H, J=7.5 Hz) and 5.25 (qt, 1H, J=7.5 Hz); $^{13}$C NMR (CDCl$_3$) δ 13.5, 13.6, 14.2, 22.8, 27.7, 29.5, 29.60, 29.72, 29.81, 29.83, 29.84, 30.7, 30.9, 31.3, 32.1, 70.9, 71.2, 130.9, 155.8, 156.4 and 158.2; mass spectrum (APCI), m/z 433.3434 (M+H)$^+$ (C$_{26}$H$_{45}$N$_2$O$_3$ requires m/z 433.3430).

Example 9. Synthesis of
2,4-Dicyclobutanoxy-6-hexadecylpyrimidin-5-ol
(3c)

Step 1. Synthesis of
2,4-Dicyclobutanoxy-6-hexadecylpyrimidine (14b)

A stirred solution containing 300 mg (1.28 mmol) of 12 in 5 mL of freshly distilled THF was cooled to −78° C. and maintained under argon. After 15 min, 800 μL (1.28 mmol) of 1.6 M n-BuLi in hexane was added dropwise and the reaction mixture was stirred at −78° C. for 1 h. A solution containing 372 mg (1.28 mmol) of 1-bromopentadecane in 1 mL of distilled THF was then added dropwise and the reaction mixture was allowed to warm to 0° C. and was stirred for 1 h. The reaction was quenched by the addition of 40 mL of satd aq NH$_4$Cl and was extracted with two 35-mL portions of CH$_2$Cl$_2$. The combined organic phase was dried over MgSO$_4$ and concentrated under diminished pressure. The residue was purified by flash chromatography on a silica gel column (15×2 cm). Elution with 98:2 hexane/EtOAc afforded compound 14b as a colorless oil: yield 520 mg (91%); silica gel TLC R$_f$ 0.4 (95:5 hexane/EtOAc); $^1$H NMR (CDCl$_3$) δ 0.85 (t, 3H, J=6.4 Hz), 1.16-1.32 (m, 26H), 1.58-1.65 (m, 4H), 1.75-1.85 (m, 2H), 2.06-2.15 (m, 2H), 2.15-2.24 (m, 2H), 2.35-2.45 (m, 4H), 2.52 (m, 2H), 5.10 (qt, 1H, J=7.5 Hz), 5.17 (qt, 1H, J=7.5 Hz) and 6.08 (s, 1H); $^{13}$C NMR (CDCl$_3$) δ 13.6, 14.2, 22.8, 27.8, 28.5, 29.4, 29.5, 29.52, 29.6, 29.74, 29.76, 29.78, 29.79, 30.6, 30.7, 32.0, 37.7, 70.3, 70.9, 99.4, 164.3, 170.7 and 173.5; mass spectrum (APCI), m/z 445.3792 (M+H)$^+$ (C$_{28}$H$_{49}$N$_2$O$_2$ requires m/z 445.3794).

Step 2, Synthesis of 2,4-Dicyclobutoxy-5-bromo-6-hexadecylpyrimidine (15b)

To a stirred solution containing 200 mg (0.45 mmol) of 14b in 2 mL of freshly distilled CH$_2$Cl$_2$ at room temperature in the dark was added 160 mg (0.90 mmol) of recrystallized N-bromosuccinimide. The reaction mixture was stirred under argon for 72 h. The solvent was concentrated under diminished pressure and the resulting residue was purified by flash chromatography on a silica gel column (15×3 cm). Elution with 98:2 hexane/EtOAc afforded compound 15b as a colorless oil: yield 227 mg (96%); silica gel TLC R$_f$ 0.45 (95:5 hexane/EtOAc); $^1$H NMR (CDCl$_3$) δ 0.87 (t, 3H, J=6.6 Hz), 1.18-1.40 (m, 26H), 1.60-1.73 (m, 4H), 1.78-1.88 (m, 2H), 2.15-2.27 (m, 4H), 2.36-2.50 (m, 4H), 2.76 (m, 2H), 5.07 (qt, 1H, J=7.4 Hz) and 5.23 (qt, 1H, J=7.6 Hz); $^{13}$C NMR (CDCl$_3$) δ 13.5, 14.2, 22.8, 27.7, 29.5, 29.53, 29.67, 29.78, 29.79, 29.81, 29.83, 30.6, 30.7, 32.1, 37.0, 71.5, 71.8, 97.6, 162.4, 166.1 and 171.1; mass spectrum (APCI), m/z 523.2901 (M+H)$^+$ (C$_{28}$H$_{48}$$^{79}$BrN$_2$O$_2$ requires m/z 523.2899). m/z 525.2896 (M+H)$^+$ (C$_{28}$H$_{48}$$^{81}$BrN$_2$O$_2$ requires m/z 525.2879).

Step 3, Synthesis of 2,4-Dicyclobutanoxy-6-hexadecylpyrimidin-5-ol (3c)

A stirred solution containing 200 mg (0.38 mmol) of 15b in 5 mL of freshly distilled THF was cooled to −78° C. and kept under argon for 10 min. To the resulting suspension was added 240 μL (0.38 mmol) of 1.6 M n-BuLi in hexane and the resulting reaction mixture was stirred at −78° C. for 1 h resulting in a clear yellowish solution. Then 84.0 μL (0.76 mmol) of trimethyl borate was added slowly and the reaction mixture was maintained at 0° C. for 1 additional hour. A solution of 300 μL of H$_2$O$_2$ (30% v/v) was then added and the reaction mixture was allowed to warm to room temperature and stirred for 30 min. The reaction mixture was diluted by the addition of 30 mL of satd aq NH$_4$Cl and extracted with two 20-mL portions of CH$_2$Cl$_2$. The combined organic phase was dried over MgSO$_4$ and concentrated under diminished pressure. The residue was purified by flash chromatography on a silica gel column (15×1 cm). Elution with 98:2 to 95:5 hexane/EtOAc afforded compound 3c as a colorless solid: yield 88 mg (52%); mp 67° C.; silica gel TLC R$_f$ 0.45 (9:1 hexane/EtOAc); $^1$H NMR (CDCl$_3$) δ 0.86 (t, 3H, J=6.7 Hz), 1.13-1.38 (m, 26H), 1.56-1.72 (m, 4H), 1.74-1.87 (m, 2H), 2.06-2.20 (m, 4H), 2.34-2.49 (m, 4H), 2.64 (m, 2H), 4.92 (br s, 1H), 5.02 (qt, 1H, J=7.5 Hz) and 5.24 (qt, 1H, J=7.6 Hz); $^{13}$C NMR (CDCl$_3$) δ 13.46, 13.54, 14.2, 22.8, 27.7, 29.5, 29.59, 29.60, 29.7, 29.78, 29.80, 29.83, 30.7, 30.8, 31.2, 32.0, 70.9, 71.2, 130.9, 155.9, 156.4 and 158.2; mass spectrum (APCI), m/z 461.3738 (M+H)$^+$ (C$_{28}$H$_{49}$N$_2$O$_3$ requires m/z 461.3743).

Example 10. Synthesis of 2,4-Di-(azetidin-1-yl)-6-methylpyrimidin-5-ol (4a)

Step 1. Synthesis of 2,4-Di-(azetidin-1-yl-6-methylpyrimidine (16)

To a suspension containing 1.00 g (6.13 mmol) of 2,4-dichloro-6-methylpyrimidine and 10.7 g (30.6 mmol) of Cs$_2$CO$_3$ in 25 mL of dry, degassed DMF was added 2.29 g (24.5 mmol) of azetidine hydrochloride and a positive pressure of argon was applied. To the reaction mixture was added 144 mg (0.61 mmol) of 3,4,7,8-tetramethyl-1,10-phenanthroline and 116 mg (0.61 mmol) of copper (I) iodide, and the reaction mixture was stirred at 60° C. under argon for 48 h. After the reaction was complete as judged by silica gel TLC analysis, the reaction mixture was diluted in 30 mL of ethyl acetate and filtered through Celite. The filtrate was concentrated to dryness and the crude residue was purified by flash chromatography on a silica gel column (15×4 cm). Elution with 9:1, 1:1, and then 1:3 hexane/EtOAc afforded 16 as a yellowish solid: yield 986 mg (78%); mp 78-79° C.; silica gel TLC R$_f$ 0.2 (1:3 hexane/EtOAc); $^1$H NMR (CDCl$_3$) δ 2.20 (s, 3H), 2.26 (qt, 2H, J=7.6 Hz), 2.33 (qt, 2H, J=7.6 Hz), 3.99 (t, 4H, J=7.6 Hz), 4.07 (t, 4H, J=7.6 Hz) and 5.41 (s, 1H); $^{13}$C NMR (CDCl$_3$) δ 16.2, 16.7, 24.2, 49.7, 50.2, 90.8, 163.5, 164.4 and 165.1; mass spectrum (APCI), m/z 205.1451 (M+H)$^+$ (C$_{11}$H$_{17}$N$_4$ requires m/z 205.1453).

Step 2. Synthesis of 2,4-Di-(azetidin-1-yl-5-bromo-6-methylpyrimidine (17)

To a stirred solution containing 205 mg (1.00 mmol) of 16 in 7 mL of dry THF at room temperature in the dark was added 180 mg (1.05 mmol) of recrystallized A-bromosuccinimide. The reaction mixture was stirred under argon for 1 h at room temperature. The solvent was concentrated under diminished pressure and the resulting residue was purified by flash chromatography on a silica gel column (15×2 cm). Elution with 95:1 to 8:2 hexane/EtOAc afforded compound 17 as a colorless solid: yield 249 mg (87%); mp 90° C.; silica gel TLC R$_f$ 0.15 (9:1 hexane/EtOAc); $^1$H NMR (CDCl$_3$) δ 2.10-2.24 (m, 4H), 2.28 (s, 3H), 3.97 (t, 4H, J=7.5 Hz), 4.22 (t, 4H, J=7.5 Hz); $^{13}$C NMR (CDCl$_3$) δ 16.0, 16.8, 24.6, 50.2, 52.6, 90.5, 160.1, 161.0 and 164.2; mass spectrum (APCI), m/z 283.0562 (M+H)$^+$ (C$_{11}$H$_{16}$$^{79}$BrN$_4$ requires m/z 283.0558) and m/z 285.0548 (M+H)$^+$ (C$_{11}$H$_{16}$$^{81}$BrN$_4$ requires m/z 2853.0538).

Step 3, Synthesis of 2,4-Di-(azetidin-1-yl)-6-methylpyrimidin-5-ol (4a)

A stirred solution containing 100 mg (0.35 mmol) of 17 in 4 mL of freshly distilled THF was cooled to −78° C. under argon for 10 min. To the resulting suspension was added 240 μL (0.38 mmol) of 1.6 M n-BuLi in hexane and the reaction mixture was stirred at −78° C. for 1 h. Then 75.0 μL (0.70 mmol) of trimethyl borate was added slowly and the reaction mixture was maintained at 0° C. for an additional hour. A solution of 200 μL of H$_2$O$_2$ (30% v/v) was then added and the reaction was allowed to warm to room temperature and stirred for 30 min. The reaction mixture was diluted by the addition of 30 mL of satd aq NH$_4$Cl and extracted with two 15-mL portions of CH$_2$Cl$_2$. The combined organic phase was dried over MgSO$_4$ and concentrated under diminished pressure. The residue was purified by flash chromatography on a silica gel column (15×1 cm). Elution with 100% CH$_2$Cl$_2$ to 9:1, and then 1:1 CH$_2$Cl$_2$/EtOAc afforded compound 4a as a colorless solid: yield 51 mg (66%); mp 147° C.; silica gel TLC R$_f$ 0.15 (1:1 CH$_2$Cl$_2$/EtOAc); $^1$H NMR (DMSO-d$_6$) δ 2.05 (s, 3H), 2.10-2.24 (m, 4H), 3.81 (t, 4H, J=7.5 Hz), 4.06 (t, 4H, J=7.5 Hz) and 7.30 (s, 1H); $^{13}$C NMR (CDCl$_3$) δ 15.6, 16.7, 18.2, 50.3, 51.6, 127.9, 151.8, 156.9 and 158.0; mass spectrum (APCI), m/z 221.1406 (M+H)⁺ ($C_{11}H_{17}N_4O$ requires m/z 221.1402).

Example 11. Synthesis of 2,4-Di-(azetidin-1-yl)-6-tetradecylpyrimidin-5-ol (4b)

Step 1. Synthesis of 2,4-Di-(azetidin-1-yl-6-tetradecylpyrimidine (18a)

A stirred solution containing 204 mg (1.00 mmol) of 16 in 10 mL of freshly distilled THF was cooled to −78° C. and maintained under argon. After 15 min, 625 µL (1.00 mmol) of 1.6 M n-BuLi in hexane was added dropwise and the reaction mixture was stirred at −78° C. for 1 h. A solution of 276 mg (0.69 mmol) of 1-bromotridecane in 500 µL of distilled THF was then added dropwise and the reaction mixture was stirred at 0° C. for 1 h. The reaction was quenched by the addition of 50 mL of satd aq $NH_4Cl$ and extracted with two 30-mL portions of $CH_2Cl_2$. The combined organic phase was dried over $MgSO_4$ and concentrated under diminished pressure. The residue was purified by flash chromatography on a silica gel column (15×3 cm). Elution with 9:1 to 1:1 hexane/EtOAc afforded compound 18a as a colorless solid: yield 378 mg (98%); mp 64° C.; silica gel TLC $R_f$ 0.2 (2:1 hexane/EtOAc); ¹H NMR (CDCl₃) δ 0.87 (t, 3H, J=6.9 Hz), 1.12-1.35 (m, 22H), 1.65 (qt, 2H, J=7.6 Hz), 2.24 (qt, 2H, J=7.6 Hz), 2.32 (qt, 2H, J=7.6 Hz), 2.41 (m, 2H), 3.98 (t, 4H, J=7.6 Hz), 4.05 (t, 4H, J=7.6 Hz) and 5.39 (s, 1H); ¹³C NMR (CDCl₃) δ 14.2, 16.3, 16.8, 22.8, 28.9, 29.5, 29.55, 29.64, 29.7, 29.76, 29.79, 32.0, 38.1, 49.8, 50.3, 90.06, 90.11, 163.7, 164.6 and 169.4; mass spectrum (APCI), m/z 387.3485 (M+H)⁺ ($C_{24}H_{43}N_4$ requires m/z 387.3488).

Step 2, Synthesis of 2,4-Di-(azetidin-1-yl-5-bromo-6-tetradecylpyrimidine (19a)

To a stirred solution containing 195 mg (0.50 mmol) of 18a in 7 mL of dry THF at room temperature in the dark was added 91.0 mg (0.52 mmol) of recrystallized N-bromosuccinimide. The reaction mixture was stirred under argon for 1 h at room temperature. The solvent was concentrated under diminished pressure and the resulting residue was purified by flash chromatography on a silica gel column (15×2 cm). Elution with 99:1 to 95:5 hexane/EtOAc afforded compound 19a as a colorless solid: yield 232 mg (98%); mp 58° C.; silica gel TLC $R_f$ 0.45 (9:1 hexane/EtOAc); ¹H NMR (CDCl₃) δ 0.88 (t, 3H, J=6.9 Hz), 1.19-1.39 (m, 22H), 1.62 (qt, 2H, J=7.5 Hz), 2.15-2.30 (m, 4H), 2.62 (m, 2H), 4.02 (t, 4H, J=7.5 Hz) and 4.28 (t, 4H, J=7.5 Hz); ¹³C NMR (CDCl₃) δ 14.2, 16.22, 16.26, 22.8, 28.1, 29.5, 29.62, 29.64, 29.72, 29.80, 29.82, 32.1, 37.1, 50.4, 52.9, 90.6, 160.7, 161.5 and 168.0; mass spectrum (APCI), m/z 465.2584 (M+H)⁺ ($C_{24}H_{42}{}^{79}BrN_4$ requires m/z 465.2593) and m/z 467.2568 (M+H)⁺ ($C_{24}H_{42}{}^{81}BrN_4$ requires m/z 467.2572).

Step 3. Synthesis of 2,4-Di-(azetidin-1-yl)-6-tetradecylpyrimidin-5-ol (4b)

A stirred solution containing 150 mg (0.32 mmol) of 19a in 4 mL of freshly distilled THF was cooled to −78° C. under argon for 10 min. To the resulting suspension was added 210 µL (0.33 mmol) of 1.6 M n-BuLi in hexane and the resulting reaction mixture was stirred at −78° C. for 1 h. Then 71.0 µL (0.64 mmol) of trimethyl borate was added slowly and the reaction mixture was stirred at 0° C. for an additional hour. A solution of 400 µL of $H_2O_2$ (30% v/v) was then added and the reaction mixture was allowed to warm to room temperature and was stirred for 30 min. The reaction mixture was diluted by the addition of 50 mL of satd aq $NH_4Cl$ and extracted with two 20-mL portions of $CH_2Cl_2$. The combined organic phase was dried over $MgSO_4$ and concentrated under diminished pressure. The residue was purified by flash chromatography on a silica gel column (15×1 cm). Elution with 95:5 to 9:1, and then 1:2 hexane/EtOAc afforded compound 4b as a colorless solid: yield 89 mg (53%); mp 65° C.; silica gel TLC $R_f$ 0.15 (1:1 hexane/EtOAc); ¹H NMR (3:1 $CD_3CN/CD_2Cl_2$) δ 0.76 (s, 3H), 1.00-1.25 (m, 22H), 1.42-1.52 (br s, 2H), 2.02-2.18 (m, 4H), 2.39 (br s, 2H), 3.79 (br s, 4H), 4.02 (br s, 4H) and 6.18 (br s, 1H); ¹³C NMR (3:1 $CD_3CN/CD_2Cl_2$) δ 14.3, 16.5, 17.7, 23.2, 25.5, 28.5, 28.7, 29.9, 30.2, 30.26, 30.29, 30.36, 30.44, 31.6, 32.5, 43.9, 51.1, 51.4, 52.5, 128.5, 150.9, 158.1 and 159.6; mass spectrum (APCI), m/z 403.3435 (M+H)⁺ ($C_{24}H_{43}N_4O$ requires m/z 403.3437).

Example 12. Synthesis of 2,4-Di-(Azetidin-1-yl)-6-hexadecylpyrimidin-5-ol (4c)

Step 1. Synthesis of 2,4-Di-(azetidin-1-yl-6-hexadecylpyrimidine (18b)

A stirred solution containing 205 mg (1.00 mmol) of 16 in 10 mL of freshly distilled THF was cooled to −78° C. under argon. After 15 min, 625 µL (1.00 mmol) of 1.6 M n-BuLi in hexane was added dropwise and the resulting reaction mixture was stirred at −78° C. for 1 h. A solution of 305 mg (1.05 mmol) of 1-bromopentadecane in 500 µL of distilled THF was then added dropwise and the reaction was stirred at 0° C. for 1 h. The reaction was quenched by adding 50 mL of satd aq $NH_4Cl$ and extracted with two 30-mL portions of $CH_2Cl_2$. The combined organic phase was dried over $MgSO_4$ and concentrated under diminished pressure. The residue was purified by flash chromatography on a silica gel column (15×3 cm). Elution with 9:1 to 1:1 hexane/EtOAc afforded compound 18b as a colorless solid: yield 337 mg (81%); mp 63° C.; silica gel TLC $R_f$ 0.2 (2:1 hexane/EtOAc); ¹H NMR (CDCl₃) δ 0.86 (t, 3H, J=6.9 Hz), 1.15-1.35 (m, 26H), 1.60 (qt, 2H, J=7.6 Hz), 2.22 (qt, 2H, J=7.5 Hz), 2.30 (qt, 2H, J=7.5 Hz), 2.40 (m, 2H), 3.97 (t, 4H, J=7.5 Hz), 4.04 (t, 4H, J=7.5 Hz) and 5.38 (s, 1H); ¹³C NMR (CDCl₃) δ 14.1, 16.2, 16.7, 22.7, 28.8, 29.4, 29.5, 29.6, 29.64, 29.71, 29.73, 29.75, 32.0, 38.0, 49.7, 50.2, 90.0, 163.7, 164.5 and 169.4; mass spectrum (APCI), m/z 415.3807 (M+H)⁺ ($C_{26}H_{47}N_4$ requires m/z 415.3801).

Step 2, Synthesis of 2,4-Di-(azetidin-1-yl-5-bromo-6-hexadecylpyrimidine (19b)

To a stirred solution containing 267 mg (0.64 mmol) of 18b in 7 mL of dry THF at room temperature in the dark was added 120 mg (0.67 mmol) of recrystallized A-Bromosuccinimide. The reaction mixture was stirred under argon for 1 h at room temperature. The solvent was removed under reduced pressure and the resulting residue was purified by flash chromatography on a silica gel column (15×2 cm). Elution with 99:1 to 95:5 hexane/EtOAc to afford compound 19b as a colorless solid: yield 289 mg (91%); mp 56° C.; silica gel TLC $R_f$ 0.45 (9:1 hexane/EtOAc); ¹H NMR (CDCl₃) δ 0.88 (t, 3H, J=7.0 Hz), 1.16-1.37 (m, 26H), 1.62 (qt, 2H, J=7.6 Hz), 2.16-2.29 (m, 4H), 2.62 (m, 2H), 4.02 (t, 4H, J=7.6 Hz) and 4.28 (t, 4H, J=7.6 Hz); 15 ¹³C NMR (CDCl₃) δ 14.2, 16.22, 16.26, 22.8, 28.1, 29.5, 29.62, 29.64, 29.73, 29.80, 29.84, 32.1, 37.1, 50.4, 52.9, 90.6, 160.7, 161.5 and 168.0; HRMS (APCI+), m/z 493.2916 (M+H)$^+$ ($C_{26}H_{46}^{79}BrN_4$ requires m/z 493.2906), m/z 495.2871 (M+H)$^+$ ($C_{26}H_{46}^{81}BrN_4$ requires m/z 495.2885).

Step 3, Synthesis of 2,4-Di-(Azetidin-1-yl-6-hexadecylpyrimidin-5-ol (4c)

A stirred solution containing 215 mg (0.43 mmol) of 19b in 5 mL of freshly distilled THF was cooled to −78° C. under argon for 10 min. To the resulting suspension was added 280 µL (0.45 mmol) of 1.6 M n-BuLi in hexane and the resulting reaction mixture was stirred at −78° C. for 1 h. Then 100 µL (0.90 mmol) of trimethyl borate was added slowly and the reaction mixture was stirred at 0° C. for an additional hour. A solution of 400 µL of $H_2O_2$ (30% v/v) was then added and the reaction mixture was allowed to warm to room temperature and stirred for 30 min. The reaction mixture was diluted by the addition of 50 mL satd aq $NH_4Cl$ and then extracted with two 20-mL portions of $CH_2Cl_2$. The combined organic phase was dried over $MgSO_4$ and concentrated under diminished pressure. The residue was purified by flash chromatography on a silica gel column (15×1 cm). Elution with 95:5 to 9:1, and then 1:2 hexane/EtOAc afforded compound 4c as a colorless solid: yield 124 mg (66%); mp 65° C.; silica gel TLC $R_f$ 0.15 (1:1 hexane/EtOAc); $^1$H NMR (3:1 $CD_3CN/CD_2Cl_2$) δ 0.76 (s, 3H), 1.00-1.25 (m, 26H), 1.42-1.52 (br s, 2H), 2.00-2.18 (m, 4H), 2.39 (br s, 2H), 3.79 (br s, 4H), 4.02 (br s, 4H) and 6.00 (br s, 1H); mass spectrum (APCI), m/z 431.3741 (M+H)$^+$ ($C_{26}H_{47}N_4O$ requires m/z 431.3750). Due to poor solubility of the product, no $^{13}$C NMR spectrum of reasonable quality could be obtained.

Biochemical and Biological Evaluation
Cell Lines and Culture Conditions

Human Mitochondrial Disease Cell Lines, Friedreich's Ataxia Lymphocytes (GM15850), and Leigh's syndrome lymphocytes (GM13740) were obtained from Coriell Cell Repositories (Camden, N.J.). Lymphocytes were cultured in RPMI-1640 medium (Gibco, Life Technologies, Grand Island, N.Y.) with 15% fetal calf serum, 2 mM glutamine (HyClone, South Logan, Utah) and 1% penicillin-streptomycin antibiotic supplement (Cellgro, Manassas, Va.). Cells were passaged every other day to maintain them in log phase growth and kept at a nominal concentration of 5-10×10$^5$ cell/mL. A CoQ$_{10}$ deficient lymphocyte cell line (GM17932) was obtained from Coriell Cell Repositories. A nutrient sensitized screening strategy to identify CoQ$_{10}$ analogues that function within the mitochondrial respiratory chain was used by growing the CoQ$_{10}$-deficient lymphocyte in galactose containing media to force energy production predominantly through oxidative phosphorylation rather than glycolysis (Goldschmidt, R., et al. *Bioorg. Med Chem.* 2013, 27, 969; Khdour, O. M., et al. *ACS Med Chem. Lett.* 2013, 4, 724; Ehrenberg, B., et al. *Biophys. J.* 1988, 53, 785; Aguer, C., et al. *PLoS One* 2011, 6, 28536; and Arce, P. M., et al. *Bioorg. Med. Chem.* 2012, 20, 5188). The lymphocytes were cultured in RPMI 1640 glucose free medium (Gibco, Grand Island, N.Y.) supplemented with 25 mM galactose, 2 mM glutamine and 1% penicillin-streptomycin, and 10% dialyzed fetal bovine serum (FBS) (<0.5 µg/mL) (Gemini Bio-Product, West Sacramento, Calif.).

Example 13. NADH Oxidase Activity

A small scale preparation of bovine heart mitochondria is prepared as described by Smith (Smith, A. L. *Methods Enzymol.* 1967, 10, 81). Bovine heart submitochondrial particles (SMPs) are prepared as described by Matsuno-Yagi and stored in a buffer containing 0.25 M sucrose and 10 mM Tris-HCl, pH 7.4, at −80° C. (Matsuno-Yagi, A., et al. *J. Biol. Chem.* 1985, 260, 11424). SMPs are diluted to 0.5 mg/mL. Mitochondrial complexes I, III, and IV activity are assayed at 30° C. and monitored spectrophotometrically using a Beckman Coulter DU-530 (340 nm, ε=6.22 mM$^{-1}$ cm$^{-1}$). NADH oxidase activity is determined in 50 mM Hepes buffer containing 5 mM MgCl$_2$, pH 7.5, in a total volume of 2.5 mL. The final mitochondrial protein concentration was 30 µg/mL. The initial rates of NADH oxidation were calculated from the linear portion of the traces. Data are reported as the mean of three independent experiments each run in triplicate.

Example 14. Lipid Peroxidation Assay

Lipid peroxidation was measured by a quantitative FACS assay using the oxidation-sensitive fatty acid probe $C_{11}$-BODIPY$^{581/591}$ (Molecular Probe) as described in art (Goldschmidt, R., et al. *Bioorg. Med Chem.* 2013, 27, 969; Khdour, O. M., et al. *ACS Med Chem. Lett.* 2013, 4, 724; and Arce, P. M., et al. *Bioorg. Med Chem.* 2012, 20, 5188). The degree of probe oxidation was followed using flow cytometry. Briefly, FRDA lymphocytes (5×10$^5$ cell/mL) were plated (1 mL in 24-well plates), treated with the test compounds and incubated at 37° C. for 16 h in a humidified atmosphere containing 5% CO$_2$ in air. The following day, cells were treated with 1 µM of $C_{11}$-BODIPY$^{581/591}$ probe in phenol red-free media and incubated at 37° C. in the dark for 30 min. Oxidative stress was induced with 5 mM DEM in phenol red-free RPMI-1640 media for 120 min. Cells were collected by centrifugation at 300×g for 3 min and then washed with phosphate buffered saline (PBS). Cells were resuspended in phosphate buffered saline and were analyzed immediately by FACS (C6 Accuri, BD Biosciences, San Jose, Calif.), using a 488 nm excitation laser and the FL1-H channel 530±15 nm emission filter. The generation of lipid peroxide was detected as a result of the oxidation of the polyunsaturated butadienyl portion of the dye, resulting in a shift of the fluorescence emission peak from red to green. In each analysis, 10,000 events were recorded after cell debris were electronically gated out. Data are reported as means±S.E.M. (n=3). Results were expressed as a percentage of the median mean fluorescence intensity of $C_{11}$-BODIPY-green relative to the treated control (DEM).

Figure 2:
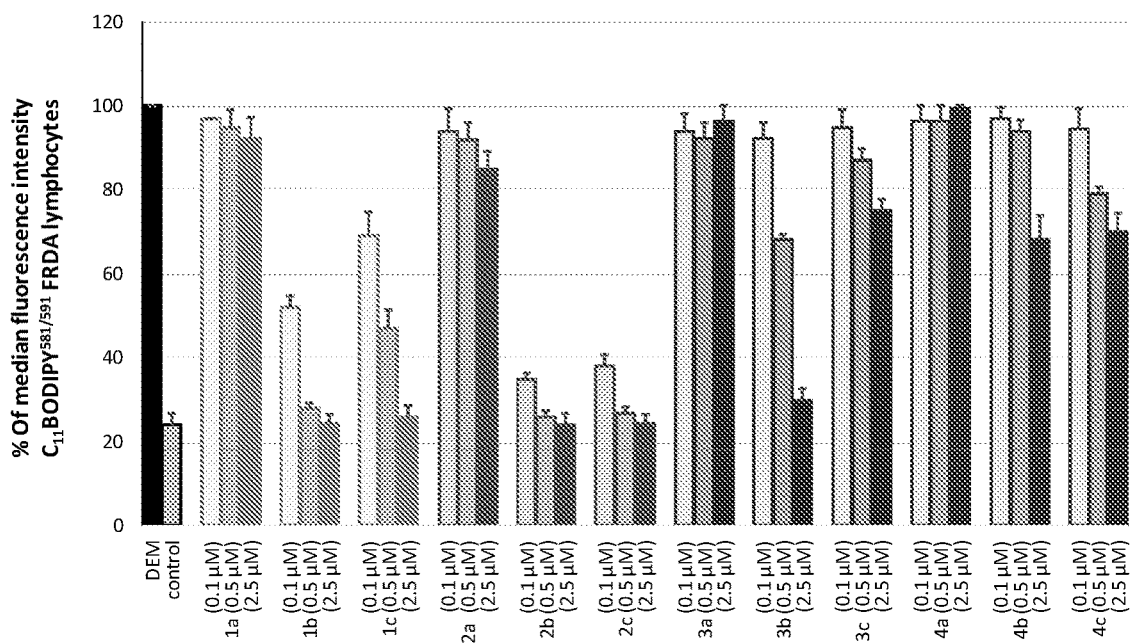
FIG. 2 shows Lipid peroxidation in FRDA lymphocytes cells depleted of glutathione by utilizing the oxidation-sensitive fatty acid probe $C_{11}$-BODIPY$^{581/591}$ and fluorescence activated cell sorting (FACS). The bar graph represents the percentage of the median mean fluorescence intensity of $C_{11}$-BODIPY-green fluorescence relative to a treated control is shown. Data are expressed as the mean±SEM (n=3).

The lipophilic fluorophore changes its fluorescence from red to green when it interacts with peroxyradicals and a measurement using FACS of intracellular lipid peroxidation, was determined by increasing the median mean fluorescence intensity of $C_{11}$-BODIPY-green relative to the untreated control. The results presented in the FIG. 2 show several important findings. First it appears that the combination of an alkoxy and an alkylamino moiety is necessary to afford good suppression of lipid peroxidation, considering that none of the dialkoxy (3a-c) or the dialkylamino (4a-c) compounds afforded good suppression. One might consider compound 3b as slightly efficient, but this was only observed at high concentration. On the contrary, compounds 1b-c and 2b-c efficiently suppressed lipid peroxidation, especially at high concentration, and there was differentiation between the two regioisomers at low concentration, as 2b was significantly more efficient than 1b at 0.1 µM concentration, just as 2c was better than 1c. The localization of the alkoxy moiety in position 2 looks more efficient in this case. Finally, the presence of a hydrophobic side chain is confirmed to be essential as no activity was observed for any redox core (1a-4a).

Example 15. Reactive Oxygen Species (ROS) Assay

Quantitative analysis of intracellular ROS levels in FRDA lymphocytes, challenged with 5 mM diethyl maleate (DEM) in presence or absence of the test compounds, was obtained by FACS analysis using a dichlorodihydrofluorescein diacetate probe (DCFH-DA), as described in art (Goldschmidt, R., et al. *Bioorg. Med Chem.* 2013, 27, 969; Arce, P. M., et al. *Bioorg. Med Chem.* 2012, 20, 5188; Arce, P. M., et al. *ACS Med Chem. Lett.* 2011, 2, 608; Khdour, O. M., et al. *Pharm. Res.* 2011, 28, 2896; Lu, J., et al. *Bioorg. Med. Chem.* 2010, 18, 7628; and Cai, X., et al. *Bioorg. Med. Chem.* 2012, 20, 3584). Briefly, 1 mL of FRDA lymphocytes ($5 \times 10^5$ cells) was plated in a 24-well plate, treated with the test compounds and incubated at 37° C. for 16 hours in a humidified atmosphere containing 5% $CO_2$ in air. Cells were treated with 5 mM diethyl maleate (DEM) for 80 minutes, collected by centrifugation at 300×g for 3 minutes and then washed with phosphate buffered saline (Life Technologies). Cells were resuspended in PBS containing 20 mM glucose and incubated at 37° C. in the dark for 25 minutes with 10 µM DCFH-DA. Cells were collected by centrifugation at 300 g for 3 minutes and then washed with PBS. The samples were analyzed immediately by flow cytometry (C6 Accuri, BD Biosciences, San Jose, Calif.), using a 488 nm excitation laser and the FL1-H channel 530±15 nm emission filter. The generation of ROS, mainly peroxides, was detected as a result of the oxidation of DCFH. In each analysis, 10,000 events were recorded after cell debris was electronically gated out. Results obtained were verified by running duplicates and repeating experiments in three independent runs. Results were expressed as a percentage of ROS scavenging activity. Results were expressed as a percentage of the median mean fluorescence intensity of DCF relative to the treated control.

Figure 3:
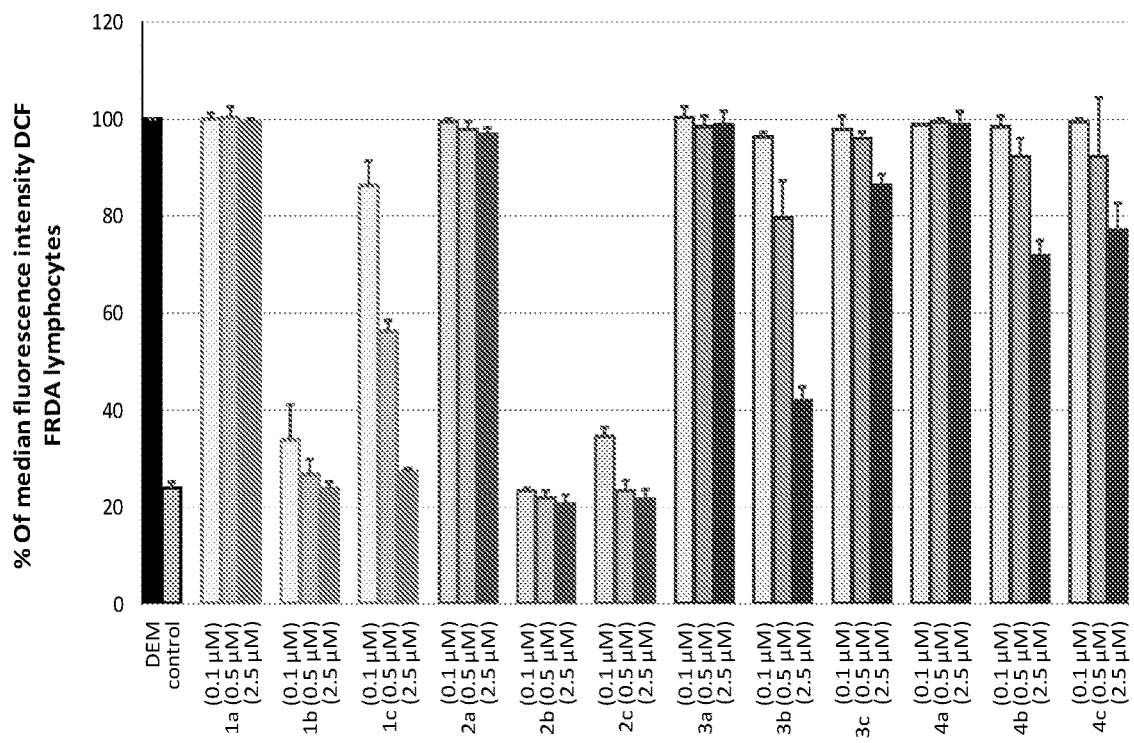
FIG. 3 shows flow cytometric analysis of ROS in FRDA lymphocyte cells pre-treated with compounds 1a-c, 2a-c, 3a-c and 4a-c at 0.1 µM, 0.5 µM and 2.5 µM concentrations for 16 hours, and then treated with diethyl maleate (DEM) for 80 minutes to induce the production of ROS. The cells were stained with 2, 7-dichlorodihydrofluorescein diacetate (DCFH-DA) for 15 minutes prior to analysis. The samples were analyzed immediately by flow cytometry (C6 Accuri, BD Biosciences, San Jose, Calif.). The bar graph represents the percentage of the median mean fluorescence intensity of DCF fluorescence relative to a DEM-treated control. Data shown represent the mean±SEM of two different experiments run as duplicates.

FIG. 3 presents the results obtained in FRDA lymphocyte cells for all the quenchers tested including the redox cores. The behaviors observed in this case are similar to the results observed for lipid peroxidation. While compound 3b appeared to be efficient at high concentration, as soon as the concentration was decreased to 0.5 µM, the protection given by the dialkoxy analogues (3a-c) or dialkylamino analogues (4a-c) was minimal. Also, the association of an alkylamino and an alkoxy groups was obviously a determinant of good efficiency for all the compounds at high concentration even if a difference in favor of the compounds 2b-c was observed at low concentration. This confirms the importance of having an alkoxy and an alkylamino moiety on the pyrimidinol scaffold bearing a hydrophobic side chain. The trend in which the isomer with the alkylamino group in position 6 looks more efficient that in position 2 is also confirmed by this test.

Example 16. Preservation of Mitochondrial Membrane Potential ($\Delta\psi_m$)

Figure 4:
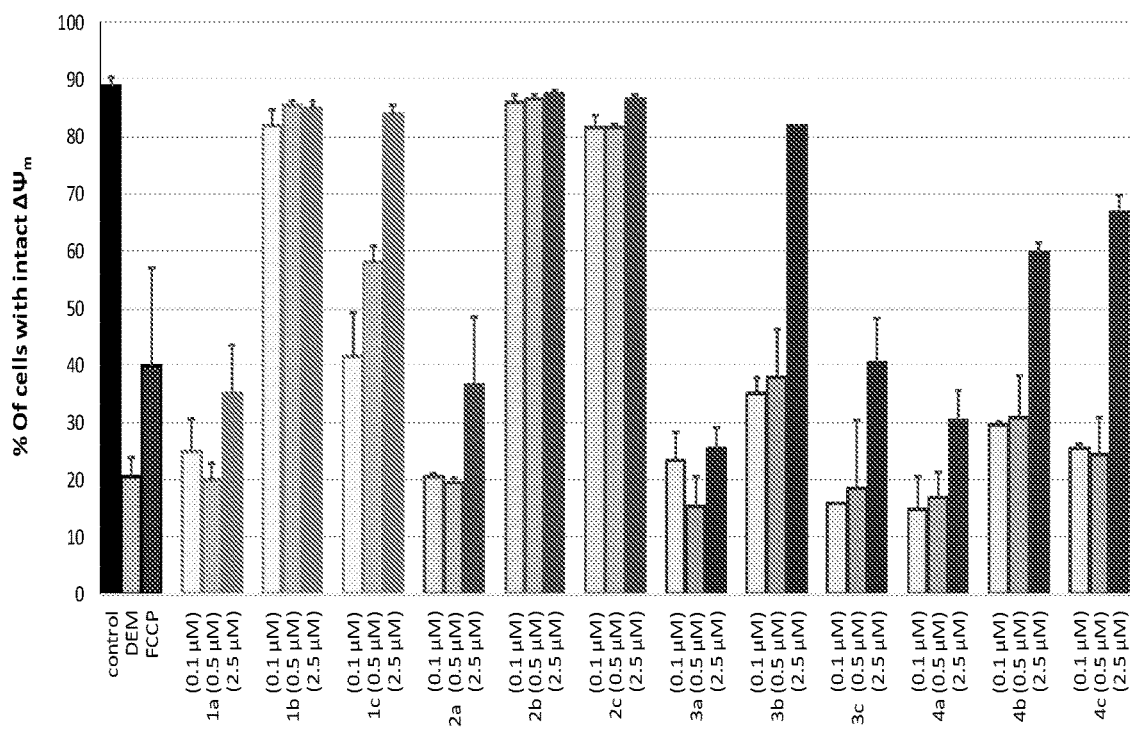
FIG. 4 shows representative flow cytometric two-dimensional color density dot plot analyses of the ability of compounds 1a-c, 2a-c, 3a-c and 4a-c to maintain mitochondrial membrane potential ($\Delta\psi_m$) in DEM-treated FRDA lymphocytes cells stained with 250 nM TMRM and analyzed using the FL2-H channel as described in the Example. A total of 10,000 events were recorded for each sample and analyzed using C6 Accuri software (BD Biosciences). The bar graph represents the percentage of the cells with intact $\Delta \psi_m$. Data are expressed as means±S.E.M. of two independent experiments run in duplicate.

Mitochondrial membrane potential of FRDA lymphocytes was assessed using the fluorescence probe Mitotracker TMRM (tetramethylrhodamine methyl ester; Molecular Probes, Portland, Oreg.) as described in art (Goldschmidt, R., et al. *Bioorg. Med Chem.* 2013, 27, 969; Khdour, O. M., et al. *ACS Med Chem. Lett.* 2013, 4, 724; Arce, P. M., et al. *Bioorg. Med. Chem.* 2012, 20, 5188; Lu, J., et al. *Bioorg. Med. Chem.* 2010, 18, 7628; and Cai, X., et al. *Bioorg. Med. Chem.* 2012, 20, 3584). TMRM is a lipophilic potentiometric dye which partitions between the mitochondria and cytosol in proportion to the negative membrane potential across the inner mitochondrial membrane, in accordance with the Nernst equation (Ehrenberg, B., et al. *Biophys. J.* 1988, 53, 785). Therefore, the accumulation of dye in the mitochondria and the intensity of the signal is a direct function of mitochondrial membrane potential. Mitochondrial depolarization then causes the redistribution of dye from mitochondria into the cytosol, causing a change in signal intensity. The detection of mitochondrial depolarization using TMRM was accomplished by flow cytometry as described in art (Goldschmidt, R., et al. *Bioorg. Med. Chem.* 2013, 21, 969; Khdour, O. M., et al. *ACS Med. Chem. Lett.* 2013, 4, 724; and Arce, P. M., et al. *Bioorg. Med. Chem.* 2012, 20, 5188). Briefly, FRDA lymphocytes cells ($5 \times 10^5$ cells) were pre-treated with or without the test compounds for 16 hours. The cells were treated with 5 mM DEM for 120 minutes, collected by centrifugation at 300×g for 3 minutes and washed with phosphate buffered saline. The cells were resuspended in PBS containing 20 mM glucose and incubated at 37° C. in the dark for 15 minutes with 250 nM TMRM. Cells were collected by centrifugation at 300×g for 3 minutes and washed with phosphate buffered saline. Cells were resuspended in phosphate buffered saline supplemented with 20 mM glucose and were analyzed immediately by FACS (C6 Accuri, BD Biosciences, San Jose, Calif.), using a 488 nm excitation laser and the FL2-H channel. For each analysis 10,000 events were recorded and the percentage of cells exhibiting a high level of TMRM uptake, which reflects normal mitochondrial membrane potential, was determined and analyzed using C6 Accuri software (BD Biosciences). The results obtained were verified in three independent experiments. FCCP (carbonyl cyanide p-trifluoromethoxyphenylhydrazone), a mitochondrial uncoupler, was used to produce a negative control. The results were verified by repeating the experiments in duplicate (FIG. 4).

Example 17. Cytoprotection (FACS Analysis Live/Dead® Viability/Cytotoxicity Assay)

The cytoprotection conferred by the representative compounds was determined in FRDA lymphocytes by using a simultaneous staining with a two-color fluorescence FACS assay, the Live/Dead® Viability/Cytotoxicity Kit (Molecular Probes). This assay is used to measure two recognized parameters of cell viability, intracellular esterase activity and plasma integrity. The membrane-impermeant DNA dye ethidium homodimer-1 (EthD-1) was used to identify dead cells whose plasma membrane integrity was disrupted. The membrane-permeant dye calcein-AM was used to label live cells. It penetrates into the cells, where it is metabolized by cytoplasmic esterases and becomes a fluorescent but membrane-impermeant probe which is retained in viable cells. Briefly, FRDA lymphocyte cells were seeded at a density of $5 \times 10^5$ cells/mL and treated with different concentrations of the test compounds. Cells were incubated at 37° C. in a humidified atmosphere of 5% $CO_2$ in air for 16 hours. Oxidative stress was then induced by incubation with 5 mM DEM for 6 hours, followed by evaluation of cytoprotection. Cells were collected by centrifugation at 300×g for 3 minutes and washed with phosphate buffered saline. Cells were resuspended in phosphate buffered saline containing 25 mM galactose. The cell suspension was stained with 0.1 µM calcein AM and 0.1 µM EthD-1 and incubated in the dark at 37° C. for 15 minutes. Cells were collected by centrifugation at 300×g for 3 minutes and then washed with PBS. The samples were analyzed immediately by flow cytometry (C6 Accuri, BD Biosciences, San Jose, Calif.), using a 488 nm excitation laser and the FL1-H channel 530±15 nm emission filter and the FL2-H channel 585±15 nm. For each analysis 10,000 events were recorded and analyzed using C6 Accuri software (BD Biosciences). Cytoprotection by the test compounds was assessed with respect to the untreated controls. Cells not treated with DEM had >90% cell viability whereas DEM treatment reduced cell viability to <20%. The cell viability was expressed relative to the vehicle control (DMSO only) group (n=3).

Figure 5:
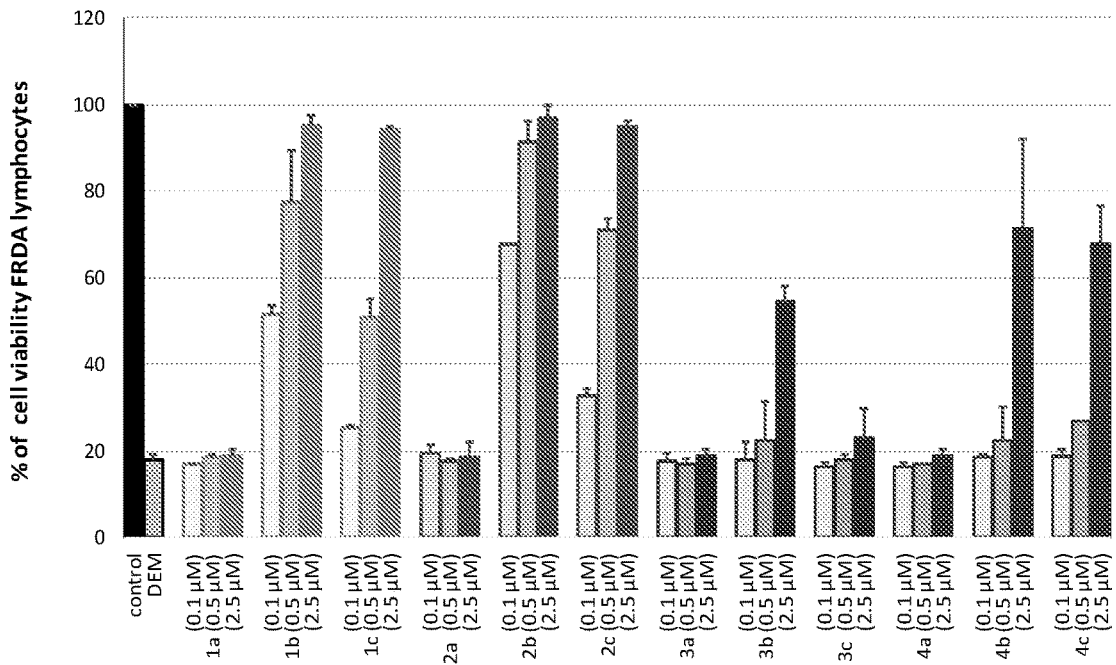
FIG. 5 shows cell viability of Friedreich's ataxia lymphocytes following pretreatment with the test compounds for 16 hours and then treatment with DEM (5 mM) for 6 hours to induce oxidative stress. Flow cytometric determination of cell viability by fluorescence labeling was used employing calcein acetoxy-methyl-ester and ethidium homodimer-1 (EthD-1) as live and dead cell stains. Cell viability was expressed as the percentage of cells relative to control. Results are an average of two independents trials run in duplicate.

The trend described in Examples 14-16 was found to be general as the same results were obtained by analyzing the capability of these molecules to preserve mitochondrial membrane potential (FIG. 4) or during the experiments to evaluate the cytoprotective effect of these quenchers (FIG. 5). All of these experiments lead to the same conclusion: the association of an alkoxy and an alkylamino moiety is essential to confer good cytoprotection, protection against lipid peroxidation or ROS over expression, and to preserve mitochondrial membrane potential. The additional information given by these tests is that the specific regioisomer is also important as the alkoxy group localized at position 2 looks much more efficient and enables the use of these MRQs at lower concentration while maintaining their biological properties.

Example 18. Cellular ATP Concentration Assay $CoQ_{10}$ deficient lymphocytes ($2\times10^5$ cell/mL) were plated (1 mL in 24-well plates) in glucose-free media supplemented with galactose and treated with the test compounds at final concentrations of 5, 10 and 25 µM, and then incubated at 37° C. for 48 h in a humidified atmosphere containing 5% $CO_2$ in air. Wells were mixed and cells in each well were transferred (100 µL) to 96-well microtiter black-walled cell culture plates (Costar, Corning, N.Y.). The total intracellular ATP level was measured in a luminator (Clarity™ luminescence microplate reader) using an ATP Bioluminescence Assay Kit (ViaLight-Plus ATP monitoring reagent kit, Lonza, Walkersville, Md.) following the manufacturer's protocol. The total ATP level was expressed as a percentage of untreated control. Data are reported as the mean of at least three independent runs.

In the present study, analogues 1a-c, 2a-c, 3a-c and 4a-c were evaluated for their ability to enhance ATP levels. Table 1 presents the results obtained during this experiment and leads to a different conclusion. First, when the dialkoxy compounds (3a-c) were not efficient in the previous assays, they support ATP production even at high concentration (20 µM), at which inhibition usually starts to be observed. Unfortunately, this time again, the combination of two alkylamino moieties as in the compounds 4a-c is obviously harmful, resulting in complete inhibition at 20 µM concentration and around 50% inhibition for compounds 4b-c at 5 µM concentration. It may be noted that this effect seems less obvious with the redox core 4a. All of the other compounds support ATP production except compound 2b but only at high concentration. We also note that the difference between the compounds 1a-c and 2a-c is less obvious in this case, with comparable efficiencies obtained at low concentration.

TABLE 1

Total ATP concentration in FRDA lymphocytes following incubation with compounds 1a-c, 2a-c, 3a-c and 4a-c for 48 h[a]

| Compound | Total ATP level (% control) FRDA lymphocytes | | |
|---|---|---|---|
|  | 1 µM | 5 µM | 20 µM |
| Untreated control | 100 | 100 | 100 |
| 1a | 100 ± 1 | 98 ± 1 | 96 ± 2 |
| 1b | 105 ± 3 | 102 ± 1 | 94 ± 2 |
| 1c | 100 ± 1 | 114 ± 3 | 103 ± 2 |
| 2a | 101 ± 1 | 99 ± 3 | 96 ± 3 |
| 2b | 109 ± 3 | 105 ± 2 | 54 ± 6 |
| 2c | 102 ± 2 | 110 ± 4 | 99 ± 2 |
| 3a | 101 ± 1 | 99 ± 2 | 97 ± 3 |
| 3b | 99 ± 1 | 98 ± 2 | 94 ± 2 |
| 3c | 98 ± 2 | 102 ± 2 | 96 ± 2 |
| 4a | 101 ± 2 | 101 ± 2 | 85 ± 9 |
| 4b | 86 ± 3 | 46 ± 7 | 1 ± 0 |
| 4c | 92 ± 1 | 61 ± 9 | 1 ± 2 |

[a]Determined from intracellular ATP levels using the luciferin-luciferase reaction.

Example 19. Microsomal Stability Assay

Liver tissues were diced into small pieces and then washed with isotonic sucrose buffer (0.25 M sucrose, 10 mM Tris-HCl, 0.5 mM EDTA, pH 7.8). The diced tissue was passed through a precooled meat grinder and mixed with three-fold ice cold sucrose buffer supplemented with a mixture of protease inhibitors. The suspension was homogenized in a Waring blender for 25 s at high speed. At this stage, the pH of the suspension was adjusted to 7.4 with 1 M Tris base. The homogenate was centrifuged for 20 min at 1200×g to remove cell debris. The supernatant suspension was homogenized in a tight fitting Teflon-glass Potter-Elvehjem homogenizer and then centrifuged twice at 10,000×g for 20 min, collecting the supernatant each time to remove mitochondria. The floating fat layer was carefully removed by filtering the supernatant through layers of cheesecloth. The supernatant was centrifuged at 150,000×g for 30 min (Beckman-Coulter ultracentrifuge, XL-100K-01, SW 55 Ti rotor). The pellet (microsomal fraction) was suspended in 0.25 M sucrose buffer containing 10 mM Tris-HCl, pH 7.4, with 20% (v/v) glycerol, and centrifuged once more at 150,000×g. The pellet was resuspended in sucrose buffer with 20% (v/v) glycerol. The protein concentration after resuspension was approximately 20 mg/mL, as determined by BCA protein assay (Pierce Chemical) using bovine serum albumin as a standard. Aliquots of microsomal suspensions were stored at −80° C.

In vitro metabolic stability was determined in bovine liver microsomes at a protein concentration of 1 mg/mL in 50 mM phosphate buffer mixture, pH 7.4, containing 5 mM $MgCl_2$ in a final incubation volume of 0.5 mL. Each test compound was added to a final concentration of 25 µM. This mixture was pre-warmed to 37° C. prior to starting the reaction by the addition of β-NADPH to 1 mM final concentration. After incubation for 30 min at 37° C., the reaction was quenched by the addition of 1 mL of propanol, vortexed for 2 min and centrifuged at 15,000×g for 10 min to pellet the precipitated protein. The resulting supernatant was pipetted out and then concentrated under diminished pressure. A parallel incubation of the test compound with deactivated microsomes (quenched immediately with propanol) lacking β-NADPH served as a control and was run for each test agent to detect microsome-independent degradation. The sample was reconstituted in 130 µL MeOH and centrifuged again at 15,000×g for 3 min. The supernatant was removed and 4 µM fluorene was added as an internal standard before HPLC analysis. HPLC analyses were performed on a Zorbax SB-Phenyl reversed phase analytical (150×4.6 mm, 5 μm) HPLC column using a mobile phase consisting of MeOH/H$_2$O. A linear gradient of (50:50 MeOH/H$_2$O→100:0 MeOH/H$_2$O) was employed over a period of 14 min at a flow rate of 1 mL/min. Metabolic stability was expressed as percent of control remaining. The experiments were carried out in duplicate to verify the results.

After reversed HPLC quantification, the results were represented in Table 2. The results show a similar stability, around 60-65% for all the compounds, leading to the conclusion that even if the biological properties of these compounds can differ from on analogue to another, the stability remains essentially the same. Only for compound 2b was a significantly better stability observed (77% recovery) but it is clear that the viability of these compounds as MRQs can't be differentiated by their microsome stability, considering the similarity of all these values.

TABLE 2

In vitro microsomal stability of the prepared compounds 1b-c, 2b-c, 3b-c and 4b-c following incubation with bovine liver microsomes. Results expressed as % of compound recovered after reaction with activated microsomes. Microsomal stability values represent means ± SD.

| Compound | Recovery (%) |
|---|---|
| 1b | 63 ± 8 |
| 1c | 65 ± 8 |
| 2b | 77 ± 3 |
| 2c | 63 ± 9 |
| 3b | 72 ± 3 |
| 3c | 60 ± 5 |
| 4b | 63 ± 5 |
| 4c | 62 ± 3 |

Example 20. The Following Illustrate Representative Pharmaceutical Dosage Forms, Containing a Compound of Formula I (Compound X), for Therapeutic or Prophylactic Use in Humans

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:
1. A compound of formula Ib:

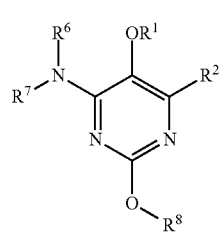

formula Ib wherein R$^1$ is hydrogen or C$_{1-6}$ alkyl;
R$^2$ is C$_{1-20}$ alkyl, C$_{2-20}$ alkenyl or C$_{2-20}$ alkynyl, and wherein the C$_{1-20}$ alkyl, C$_{2-20}$ alkenyl and C$_{2-20}$ alkynyl are optionally substituted with one or more groups independently selected from —F, —Cl, —Br, —I, —OR$^a$, —SR$^a$, —N(R$^a$)$_2$, oxo, —NO$_2$ and —CN;

R$^6$ is C$_{1-6}$ alkyl, C$_{2-6}$ alkenyl or C$_{2-6}$ alkynyl, and wherein the C$_{1-6}$ alkyl, C$_{2-6}$ alkenyl and C$_{2-6}$ alkynyl are optionally substituted with one or more groups independently selected from —F, —Cl, —Br, —I, —OR$^e$, SR$^e$, —N(R$^e$)$_2$, oxo, —NO$_2$ and —CN; R$^7$ is C$_{1-6}$ alkyl, C$_{2-6}$ alkenyl or C$_{2-6}$ alkynyl, and wherein the C$_{1-6}$ alkyl, C$_{2-6}$ alkenyl and C$_{2-6}$ alkynyl are optionally substituted with one or more groups independently selected from —F, —Cl, —Br, —I, —OR$^d$, —SR$^d$, —N(R$^d$)$_2$, oxo, —NO$_2$ and —CN; or R$^6$ and R$^7$ taken together with the nitrogen to which they are attached form a 3-10 membered heterocycle that is optionally substituted with one or more groups independently selected from C$_{1-4}$ alkyl, C$_{1-4}$ haloalkyl, —F, —Cl, —Br, —I, —OR$^e$, —N(R$^e$)$_2$, oxo, —NO$_2$ and —CN;

R$^8$ is C$_{3-10}$ cycloalkyl or C$_{1-8}$ alkyl; wherein C$_{3-10}$ cycloalkyl and C$_{1-8}$ alkyl are optionally substituted with one or more groups independently selected from C$_{1-4}$ alkyl, C$_{1-4}$ haloalkyl, —F, —Cl, —Br, —I, —OR$^f$, —SR$^f$, —N(R$^f$)$_2$, oxo, —NO$_2$ and —CN;

each R$^a$ is independently hydrogen or C$_{1-4}$ alkyl; or two R$^a$ taken together with the nitrogen to which they are attached form pyrrolidinyl, piperidinyl, piperazinyl or morpholinyl;

each R$^c$ is independently hydrogen or C$_{1-4}$ alkyl; or two R$^c$ taken together with the nitrogen to which they are attached form pyrrolidinyl, piperidinyl, piperazinyl or morpholinyl;

each R$^d$ is independently hydrogen or C$_{1-4}$ alkyl; or two R$^d$ taken together with the nitrogen to which they are attached form pyrrolidinyl, piperidinyl, piperazinyl or morpholinyl;

each R$^e$ is independently hydrogen or C$_{1-4}$ alkyl; or two R$^e$ taken together with the nitrogen to which they are attached form pyrrolidinyl, piperidinyl, piperazinyl or morpholinyl;

each R$^f$ is independently hydrogen or C$_{1-4}$ alkyl; or two R$^f$ taken together with the nitrogen to which they are attached form pyrrolidinyl, piperidinyl, piperazinyl or morpholinyl; and each R$^g$ is independently hydrogen or C$_{1-4}$ alkyl; or two R$^g$ taken together with the nitrogen to which they are attached form pyrrolidinyl, piperidinyl, piperazinyl or morpholinyl; or a pharmaceutically acceptable salt thereof.

2. The compound of claim 1, wherein R$^2$ is C$_{10-20}$ alkyl.

3. The compound of claim 1, wherein R$^2$ is methyl, tetradecyl or hexadecyl.

4. The compound of claim 1, wherein R$^6$ and R$^7$ taken together with the nitrogen to which they are attached form a 3-10 membered heterocycle that is optionally substituted with one or more groups independently selected from C$_{1-4}$ alkyl, C$_{1-4}$ haloalkyl, —F, —Cl, —Br, —I, —OR$^e$, —SR$^e$, —N(R$^e$)$_2$, oxo, —NO$_2$ and —CN.

5. The compound of claim 1, wherein R$^2$ is C$_{10-20}$ alkyl; and R$^6$ and R$^7$ taken together with the nitrogen to which they are attached form a 3-10 membered heterocycle that is optionally substituted with one or more groups independently selected from C$_{1-4}$ alkyl, C$_{1-4}$ haloalkyl, —F, —Cl, —Br, —I, —OR$^i$, —SR$^i$, —N(R$^i$)$_2$, oxo, —NO$_2$ and —CN.

6. The compound of claim 1, wherein —NR$^6$R$^7$ is:

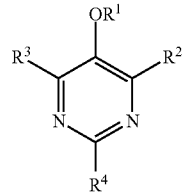

formula I

7. The compound of claim 1, wherein —OR$^8$ is

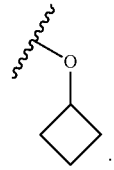 [SMILES: *OC1CCC1]

8. A compound that is selected from the group consisting of:

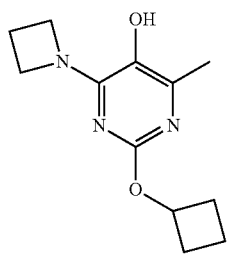

2a

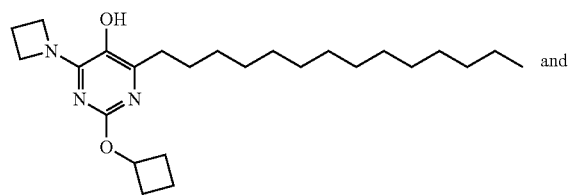

2b and

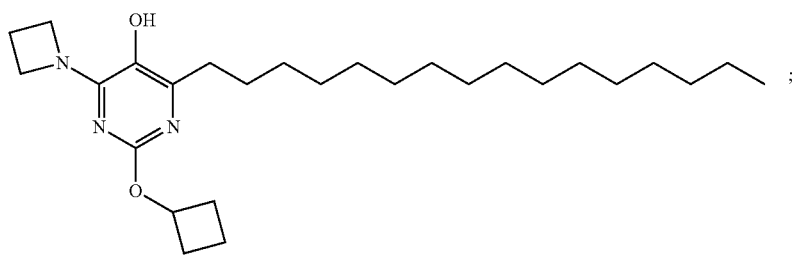

2c

;

and pharmaceutically acceptable salts thereof.

9. The compound or pharmaceutically acceptable salt of claim 8, which is:
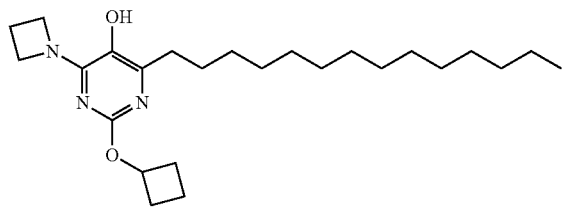
2b
or a pharmaceutically acceptable salt thereof.
10. A pharmaceutical composition comprising a compound of formula Ib as described in claim 1, or a pharmaceutically acceptable salt thereof, and a pharmaceutically acceptable carrier.
* * * * *